US008764794B2

(12) United States Patent
Argenta et al.

(10) Patent No.: US 8,764,794 B2
(45) Date of Patent: Jul. 1, 2014

(54) DEVICE AND METHOD FOR TREATING CENTRAL NERVOUS SYSTEM PATHOLOGY

(71) Applicant: Wake Forest University Health Sciences, Winston-Salem, NC (US)

(72) Inventors: Louis C Argenta, Winston-Salem, NC (US); David L Carroll, Winston-Salem, NC (US); Nicole H Levi, Winston-Salem, NC (US); Michael J Morykwas, Winston-Salem, NC (US); Stephen B Tatter, Winston-Salem, NC (US); William D Wagner, Clemmons, NC (US); Jie Liu, Woodbury, MN (US)

(73) Assignee: Wake Forest University Health Sciences, Winston-Salem, NC (US)

(*) Notice: Subject to any disclaimer, the term of this patent is extended or adjusted under 35 U.S.C. 154(b) by 0 days.

(21) Appl. No.: 13/622,009

(22) Filed: Sep. 18, 2012

(65) Prior Publication Data

US 2013/0072827 A1    Mar. 21, 2013

Related U.S. Application Data

(63) Continuation of application No. 12/351,331, filed on Jan. 9, 2009, now Pat. No. 8,267,960.

(60) Provisional application No. 61/081,997, filed on Jul. 18, 2008, provisional application No. 61/019,968, filed on Jan. 9, 2008.

(51) Int. Cl.
*A61B 17/08* (2006.01)

(52) U.S. Cl.
USPC .......................................... 606/215

(58) Field of Classification Search
CPC ...... A61M 1/00; A61M 1/0023; A61M 1/008; A61M 1/0088
USPC .................... 606/213, 215; 424/423
See application file for complete search history.

(56) References Cited

U.S. PATENT DOCUMENTS

| 765,746 A | 7/1904 | Miner |
| 774,529 A | 11/1904 | Nieschang |
| 843,674 A | 2/1907 | Funk |
| 1,000,001 A | 8/1911 | Holz |
| 1,355,679 A | 10/1920 | McConnell |

(Continued)

FOREIGN PATENT DOCUMENTS

| AU | 2003231870 | 4/2009 |
| DE | 372727 | 3/1923 |

(Continued)

OTHER PUBLICATIONS

Moues, C.M., et al., "An economic evaluation of the use of TNP on full-thickness wounds", J. Wound Care, 14 (5):224-7 (May 2005).

(Continued)

*Primary Examiner* — Gregory Anderson
(74) *Attorney, Agent, or Firm* — Niels Haun; Dann Dorfman Herrell & Skillman, PC

(57) ABSTRACT

The present invention relates generally to a device and method for treating tissues of the central nervous system and more particularly, but not exclusively, to a device and method for treating the brain tissue.

25 Claims, 18 Drawing Sheets

(56) References Cited

U.S. PATENT DOCUMENTS

| | | |
|---|---|---|
| 1,355,846 A | 10/1920 | Rannells |
| 1,385,346 A | 7/1921 | Taylor |
| 1,936,129 A | 11/1933 | Fisk |
| 2,025,492 A | 12/1935 | Aird |
| 2,122,121 A | 6/1938 | Tillotson |
| 2,195,771 A | 4/1940 | Estler |
| 2,221,758 A | 11/1940 | Elmquist |
| 2,232,254 A | 2/1941 | Morgan |
| 2,280,915 A | 4/1942 | Johnson |
| 2,338,339 A | 1/1944 | LaMere |
| 2,443,481 A | 6/1948 | Sene |
| 2,547,758 A | 4/1951 | Keeling |
| 2,573,791 A | 11/1951 | Howells |
| 2,577,945 A | 12/1951 | Atherton |
| 2,632,443 A | 3/1953 | Lesher |
| 2,682,873 A | 7/1954 | Evans |
| 2,910,763 A | 11/1959 | Lauterbach |
| 2,969,057 A | 1/1961 | Simmons |
| 3,026,874 A | 3/1962 | Stevens |
| 3,042,041 A | 7/1962 | Jascalevich |
| 3,115,138 A | 12/1963 | McElvenny |
| 3,315,665 A | 4/1967 | MacLeod |
| 3,324,855 A | 6/1967 | Heimlich |
| 3,367,332 A | 2/1968 | Groves |
| 3,382,867 A | 5/1968 | Reaves |
| 3,429,313 A | 2/1969 | Romanelli |
| 3,486,504 A | 12/1969 | Austin, Jr. |
| 3,520,300 A | 7/1970 | Flower et al. |
| 3,528,416 A | 9/1970 | Chamberlain |
| 3,568,675 A | 3/1971 | Harvey |
| 3,572,340 A | 3/1971 | Lloyd et al. |
| 3,610,238 A | 10/1971 | Rich, Jr. |
| 3,648,692 A | 3/1972 | Wheeler |
| 3,682,180 A | 8/1972 | McFarlane |
| 3,713,622 A | 1/1973 | Dinger |
| 3,753,439 A | 8/1973 | Brugarolas et al. |
| 3,782,377 A | 1/1974 | Rychlik |
| 3,782,387 A | 1/1974 | Falabella |
| 3,812,972 A | 5/1974 | Rosenblum |
| 3,814,095 A | 6/1974 | Lubens |
| 3,826,254 A | 7/1974 | Mellor |
| 3,874,387 A | 4/1975 | Barbieri |
| 3,896,810 A | 7/1975 | Akiyama |
| 3,903,882 A | 9/1975 | Augurt |
| 3,908,664 A | 9/1975 | Loseff |
| 3,935,863 A | 2/1976 | Kliger |
| 3,938,540 A | 2/1976 | Holbrook et al. |
| 3,954,105 A | 5/1976 | Nordby et al. |
| 3,975,567 A | 8/1976 | Lock |
| 3,978,855 A | 9/1976 | McRae et al. |
| 3,992,725 A | 11/1976 | Homsy |
| 3,993,080 A | 11/1976 | Loseff |
| 3,998,227 A | 12/1976 | Holbrook et al. |
| RE29,319 E | 7/1977 | Nordby et al. |
| 4,080,970 A | 3/1978 | Miller |
| 4,112,947 A | 9/1978 | Nehring |
| 4,139,004 A | 2/1979 | Gonzalez, Jr. |
| 4,149,541 A | 4/1979 | Gammons et al. |
| 4,156,066 A | 5/1979 | Gould |
| 4,169,563 A | 10/1979 | Leu |
| 4,184,510 A | 1/1980 | Murry et al. |
| 4,187,852 A | 2/1980 | Urry et al. |
| 4,191,204 A | 3/1980 | Nehring |
| 4,221,215 A | 9/1980 | Mandelbaum |
| 4,224,941 A | 9/1980 | Stivala |
| 4,224,945 A | 9/1980 | Cohen |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,297,995 A | 11/1981 | Golub |
| 4,341,209 A | 7/1982 | Schaar |
| 4,373,519 A | 2/1983 | Errede et al. |
| 4,382,441 A | 5/1983 | Svedman |
| 4,392,853 A | 7/1983 | Muto |
| 4,399,816 A | 8/1983 | Spangler |
| 4,419,097 A | 12/1983 | Rowland |
| 4,452,845 A | 6/1984 | Lloyd et al. |
| 4,457,755 A | 7/1984 | Wilson |
| 4,459,139 A | 7/1984 | vonReis et al. |
| 4,465,062 A | 8/1984 | Versaggi et al. |
| 4,465,485 A | 8/1984 | Kashmer et al. |
| 4,475,909 A | 10/1984 | Eisenberg |
| 4,480,638 A | 11/1984 | Schmid |
| 4,499,896 A | 2/1985 | Heinecke |
| RE31,887 E | 5/1985 | Hodgson |
| 4,525,166 A | 6/1985 | Leclerc |
| 4,533,352 A | 8/1985 | Van Beek |
| 4,540,412 A | 9/1985 | Van Overloop |
| 4,543,100 A | 9/1985 | Brodsky |
| 4,553,967 A | 11/1985 | Ferguson |
| 4,569,674 A | 2/1986 | Phillips et al. |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielsen |
| 4,624,656 A | 11/1986 | Clark et al. |
| 4,627,427 A | 12/1986 | Arco |
| 4,633,863 A | 1/1987 | Filips |
| 4,637,819 A | 1/1987 | Ouellette |
| 4,640,688 A | 2/1987 | Hauser |
| 4,641,643 A | 2/1987 | Greer |
| 4,655,754 A | 4/1987 | Richmond et al. |
| 4,661,093 A | 4/1987 | Beck et al. |
| 4,664,652 A | 5/1987 | Weilbacher |
| 4,664,662 A | 5/1987 | Webster |
| 4,667,666 A | 5/1987 | Fryslie |
| 4,679,590 A | 7/1987 | Hergenroeder |
| 4,710,165 A | 12/1987 | McNeil et al. |
| 4,713,052 A | 12/1987 | Beck |
| 4,717,382 A | 1/1988 | Clemens et al. |
| 4,733,659 A | 3/1988 | Edenbaum |
| 4,743,232 A | 5/1988 | Kruger |
| 4,747,166 A | 5/1988 | Kuntz |
| 4,753,231 A | 6/1988 | Lang et al. |
| 4,753,232 A | 6/1988 | Ward |
| 4,759,354 A | 7/1988 | Quarfoot |
| 4,764,167 A | 8/1988 | Tu |
| 4,773,409 A | 9/1988 | Cilento |
| 4,778,446 A | 10/1988 | Jensen |
| 4,778,456 A | 10/1988 | Lokken |
| 4,820,265 A | 4/1989 | DeSatnick et al. |
| 4,820,284 A | 4/1989 | Hauri |
| 4,822,278 A | 4/1989 | Oliva |
| 4,834,110 A | 5/1989 | Richard |
| 4,836,192 A | 6/1989 | Abbate |
| 4,838,883 A | 6/1989 | Matsuura |
| 4,840,187 A | 6/1989 | Brazier |
| 4,841,962 A * | 6/1989 | Berg et al. ................ 602/50 |
| 4,851,545 A | 7/1989 | Song et al. |
| 4,860,737 A | 8/1989 | Lang et al. |
| 4,863,449 A | 9/1989 | Therriault |
| 4,872,450 A | 10/1989 | Austad |
| 4,875,473 A | 10/1989 | Alvarez |
| 4,878,901 A | 11/1989 | Sachse |
| 4,890,608 A | 1/1990 | Steer |
| 4,897,081 A | 1/1990 | Poirier |
| 4,906,233 A | 3/1990 | Moriuchi et al. |
| 4,906,240 A | 3/1990 | Reed |
| 4,917,112 A | 4/1990 | Kalt |
| 4,921,492 A | 5/1990 | Schultz et al. |
| 4,925,447 A | 5/1990 | Rosenblatt |
| 4,931,519 A | 6/1990 | Song et al. |
| 4,941,882 A | 7/1990 | Ward et al. |
| 4,953,565 A | 9/1990 | Tachibana et al. |
| 4,969,880 A | 11/1990 | Zamierowski |
| 4,969,881 A | 11/1990 | Viesturs |
| 4,988,336 A | 1/1991 | Kohn |
| 4,990,144 A | 2/1991 | Blott |
| 4,991,574 A | 2/1991 | Pocknell |
| 4,997,425 A | 3/1991 | Shioya |
| 5,002,528 A | 3/1991 | Palestrant |
| 5,002,529 A | 3/1991 | Cunningham |
| 5,003,971 A | 4/1991 | Buckley |

(56) References Cited

U.S. PATENT DOCUMENTS

| | | | |
|---|---|---|---|
| 5,014,389 A | 5/1991 | Ogilvie |
| 5,019,086 A | 5/1991 | Neward |
| 5,024,841 A | 6/1991 | Chu et al. |
| 5,034,006 A | 7/1991 | Hosoda |
| 5,035,884 A | 7/1991 | Song et al. |
| 5,042,978 A | 8/1991 | Quenin |
| 5,060,662 A | 10/1991 | Farnswoth, III |
| 5,071,403 A | 12/1991 | Larsson |
| 5,073,172 A | 12/1991 | Fell |
| 5,086,763 A | 2/1992 | Hathman |
| 5,086,764 A | 2/1992 | Gilman |
| 5,100,396 A | 3/1992 | Zamierowski |
| 5,101,808 A | 4/1992 | Kobayashi |
| 5,106,362 A | 4/1992 | Gilman |
| 5,106,629 A | 4/1992 | Cartmell |
| 5,113,871 A | 5/1992 | Viljanto |
| 5,135,518 A | 8/1992 | Vera |
| 5,147,338 A | 9/1992 | Lang |
| 5,149,331 A | 9/1992 | Ferdman et al. |
| 5,152,757 A | 10/1992 | Eriksson |
| 5,160,322 A | 11/1992 | Scheremet |
| 5,167,613 A | 12/1992 | Karami |
| 5,170,781 A | 12/1992 | Loomis |
| 5,176,663 A | 1/1993 | Svedman |
| 5,176,667 A | 1/1993 | DeBring |
| 5,192,282 A | 3/1993 | Draenert |
| 5,215,539 A | 6/1993 | Schoolman |
| 5,224,947 A | 7/1993 | Cooper |
| 5,230,350 A | 7/1993 | Fentress |
| 5,261,893 A | 11/1993 | Zamierowski |
| 5,263,922 A | 11/1993 | Sova |
| 5,298,015 A | 3/1994 | Komatsuzaki |
| 5,330,452 A | 7/1994 | Zook |
| 5,344,415 A | 9/1994 | DeBusk |
| 5,349,965 A | 9/1994 | McCarver |
| 5,358,494 A | 10/1994 | Svedman |
| 5,376,252 A | 12/1994 | Ekstrom |
| 5,395,315 A | 3/1995 | Griep |
| 5,419,768 A | 5/1995 | Kayser |
| 5,431,662 A | 7/1995 | Nicholas |
| 5,437,651 A | 8/1995 | Todd |
| 5,445,604 A | 8/1995 | Lang |
| 5,447,492 A | 9/1995 | Cartmell et al. |
| 5,451,215 A | 9/1995 | Wolter |
| 5,456,267 A | 10/1995 | Stark |
| 5,478,333 A | 12/1995 | Asherman, Jr. |
| 5,484,399 A | 1/1996 | DiResta et al. |
| 5,484,427 A | 1/1996 | Gibbons |
| 5,487,889 A | 1/1996 | Eckert |
| 5,490,962 A * | 2/1996 | Cima et al. .................. 264/401 |
| 5,496,262 A | 3/1996 | Johnson, Jr. |
| 5,520,652 A | 5/1996 | Peterson |
| 5,522,901 A | 6/1996 | Thomas et al. |
| 5,527,293 A | 6/1996 | Zamierowski |
| 5,531,670 A | 7/1996 | Westby |
| 5,542,918 A | 8/1996 | Atkinson |
| 5,549,584 A | 8/1996 | Gross |
| 5,556,375 A | 9/1996 | Ewall |
| 5,578,022 A | 11/1996 | Scherson |
| 5,580,353 A | 12/1996 | Mendes et al. |
| 5,588,955 A | 12/1996 | Johnson, Jr. |
| 5,599,330 A | 2/1997 | Rainin |
| 5,607,388 A | 3/1997 | Ewall |
| 5,628,735 A | 5/1997 | Skow |
| 5,636,643 A | 6/1997 | Argenta et al. |
| 5,645,081 A | 7/1997 | Argenta et al. |
| 5,655,258 A | 8/1997 | Heintz |
| 5,656,027 A | 8/1997 | Ellingboe |
| 5,662,598 A | 9/1997 | Tobin |
| 5,662,624 A | 9/1997 | Sundstrom |
| 5,662,625 A | 9/1997 | Westwood |
| 5,678,564 A | 10/1997 | Lawrence |
| 5,697,920 A | 12/1997 | Gibbons |
| 5,716,360 A | 2/1998 | Baldwin et al. |
| 5,717,005 A | 2/1998 | Richardson |
| 5,717,030 A | 2/1998 | Dunn |
| 5,720,720 A | 2/1998 | Laske |
| 5,733,884 A | 3/1998 | Barbul |
| 5,735,833 A | 4/1998 | Olson |
| 5,736,372 A | 4/1998 | Vacanti et al. |
| 5,738,686 A | 4/1998 | Kubein-Messenburg et al. |
| 5,743,912 A | 4/1998 | Lahille et al. |
| 5,762,640 A | 6/1998 | Kajiwara |
| 5,766,618 A | 6/1998 | Laurencin et al. |
| 5,782,871 A | 7/1998 | Fujiwara |
| 5,810,840 A | 9/1998 | Lindsay |
| 5,817,145 A | 10/1998 | Augustine |
| 5,827,246 A | 10/1998 | Bowen |
| 5,869,080 A | 2/1999 | McGregor et al. |
| 5,876,359 A | 3/1999 | Bock et al. |
| 5,911,222 A | 6/1999 | Lawrence |
| 5,919,476 A | 7/1999 | Fischer |
| 5,921,972 A | 7/1999 | Skow |
| 5,928,174 A | 7/1999 | Gibbins |
| 5,935,136 A | 8/1999 | Hulse et al. |
| 5,941,859 A | 8/1999 | Lerman |
| 5,947,914 A | 9/1999 | Augustine |
| 5,951,295 A | 9/1999 | Lyles et al. |
| 5,954,680 A | 9/1999 | Augustine |
| 5,958,314 A | 9/1999 | Draenert |
| 5,961,480 A | 10/1999 | Augustine |
| 5,964,721 A | 10/1999 | Augustine |
| 5,964,723 A | 10/1999 | Augustine |
| 5,964,733 A | 10/1999 | Laabs et al. |
| 5,968,047 A | 10/1999 | Reed |
| 5,986,163 A | 11/1999 | Augustine |
| 6,010,527 A | 1/2000 | Augustine |
| 6,045,518 A | 4/2000 | Augustine |
| 6,045,541 A | 4/2000 | Matsumoto |
| 6,051,016 A | 4/2000 | Mesaros et al. |
| 6,053,416 A | 4/2000 | Specht |
| 6,071,254 A | 6/2000 | Augustine |
| 6,071,267 A | 6/2000 | Zamierowski |
| 6,071,304 A | 6/2000 | Augustine |
| 6,080,189 A | 6/2000 | Augustine |
| 6,080,243 A | 6/2000 | Insley |
| 6,086,587 A | 7/2000 | Hawk |
| 6,087,553 A | 7/2000 | Cohen et al. |
| 6,093,160 A | 7/2000 | Augustine |
| 6,095,148 A | 8/2000 | Shastri |
| 6,095,992 A | 8/2000 | Augustine |
| 6,106,913 A * | 8/2000 | Scardino et al. ............. 428/36.3 |
| 6,110,197 A | 8/2000 | Augustine |
| 6,113,561 A | 9/2000 | Augustine |
| 6,117,111 A | 9/2000 | Fleischmann |
| 6,135,116 A | 10/2000 | Vogel |
| 6,142,982 A | 11/2000 | Hunt |
| 6,143,945 A | 11/2000 | Augustine |
| 6,146,423 A | 11/2000 | Cohen et al. |
| 6,159,246 A | 12/2000 | Mendes et al. |
| 6,174,306 B1 | 1/2001 | Fleischmann |
| 6,187,047 B1 | 2/2001 | Kwan et al. |
| 6,190,391 B1 | 2/2001 | Stubbs |
| 6,203,563 B1 | 3/2001 | Fernandez |
| 6,207,875 B1 | 3/2001 | Lindqvist |
| 6,213,965 B1 | 4/2001 | Augustine |
| 6,213,966 B1 | 4/2001 | Augustine |
| 6,217,535 B1 | 4/2001 | Augustine |
| 6,235,009 B1 | 5/2001 | Skow |
| 6,235,047 B1 | 5/2001 | Augustine |
| 6,241,697 B1 | 6/2001 | Augustine |
| 6,241,698 B1 | 6/2001 | Augustine |
| 6,248,084 B1 | 6/2001 | Augustine |
| 6,254,557 B1 | 7/2001 | Augustine |
| 6,254,580 B1 | 7/2001 | Svedman |
| 6,264,622 B1 | 7/2001 | Augustine |
| 6,264,979 B1 | 7/2001 | Svedman |
| 6,267,740 B1 | 7/2001 | Augustine |
| 6,283,931 B1 | 9/2001 | Augustine |
| 6,284,941 B1 | 9/2001 | Cox |
| 6,290,685 B1 | 9/2001 | Insley |
| 6,293,917 B1 | 9/2001 | Augustine |
| 6,323,146 B1 | 11/2001 | Pugh |
| 6,325,788 B1 | 12/2001 | McKay |

(56) References Cited

U.S. PATENT DOCUMENTS

| | | |
|---|---|---|
| 6,344,061 B1 | 2/2002 | Leitao et al. |
| 6,345,623 B1 | 2/2002 | Heaton et al. |
| 6,355,215 B1 | 3/2002 | Poggie et al. |
| 6,359,189 B1 | 3/2002 | Fleischmann |
| 6,377,653 B1 | 4/2002 | Lee et al. |
| 6,394,948 B1 | 5/2002 | Borst et al. |
| 6,398,767 B1 | 6/2002 | Fleischmann |
| 6,430,427 B1 | 8/2002 | Lee et al. |
| 6,458,109 B1 | 10/2002 | Henley |
| 6,484,716 B1 | 11/2002 | Leininger |
| 6,485,503 B2 | 11/2002 | Jacobs et al. |
| 6,488,643 B1 | 12/2002 | Tumey |
| 6,491,693 B1 | 12/2002 | Lytinas |
| 6,520,982 B1 | 2/2003 | Boynton |
| 6,551,317 B2 | 4/2003 | Berish et al. |
| 6,553,998 B2 | 4/2003 | Heaton et al. |
| 6,555,729 B1 | 4/2003 | Fleischmann |
| 6,641,604 B1 | 11/2003 | Adelman |
| 6,648,862 B2 | 11/2003 | Watson |
| 6,663,349 B1 | 12/2003 | Discenzo |
| 6,673,028 B1 | 1/2004 | Argenta et al. |
| 6,682,491 B2 | 1/2004 | Johnson |
| 6,685,681 B2 | 2/2004 | Lockwood |
| 6,695,823 B1 | 2/2004 | Lina |
| 6,712,851 B1 | 3/2004 | Lemperle et al. |
| 6,749,592 B2 | 6/2004 | Lord |
| 6,752,794 B2 | 6/2004 | Lockwood |
| 6,755,807 B2 | 6/2004 | Risk, Jr. |
| 6,764,462 B2 | 7/2004 | Risk, Jr. |
| 6,767,334 B1 | 7/2004 | Randolph |
| 6,770,794 B2 | 8/2004 | Fleischmann |
| 6,793,633 B2 | 9/2004 | Douglas et al. |
| 6,800,074 B2 | 10/2004 | Henley |
| 6,814,079 B2 | 11/2004 | Heaton et al. |
| 6,824,533 B2 | 11/2004 | Risk, Jr. |
| 6,840,960 B2 | 1/2005 | Bubb |
| 6,855,135 B2 | 2/2005 | Lockwood |
| 6,856,821 B2 | 2/2005 | Johnson |
| 6,878,119 B2 | 4/2005 | Johnson |
| 6,887,246 B2 | 5/2005 | Bhatnagar et al. |
| 6,936,037 B2 | 8/2005 | Bubb |
| 6,951,553 B2 | 10/2005 | Bubb |
| 6,988,423 B2 | 1/2006 | Bolam |
| 6,994,702 B1 | 2/2006 | Johnson |
| 7,004,915 B2 | 2/2006 | Boynton |
| 7,022,113 B2 | 4/2006 | Lockwood |
| 7,066,960 B1 | 6/2006 | Dickman |
| 7,070,584 B2 | 7/2006 | Johnson |
| 7,077,832 B2 | 7/2006 | Fleischmann |
| 7,108,683 B2 | 9/2006 | Zamierowski |
| 7,117,869 B2 | 10/2006 | Heaton |
| 7,128,735 B2 | 10/2006 | Weston |
| 7,144,390 B1 | 12/2006 | Hannigan |
| 7,169,151 B1 | 1/2007 | Lytinas |
| 7,175,625 B2 | 2/2007 | Culbert |
| 7,198,046 B1 | 4/2007 | Argenta |
| 7,216,651 B2 | 5/2007 | Argenta |
| 7,276,051 B1 | 10/2007 | Henley et al. |
| 7,279,612 B1 | 10/2007 | Heaton et al. |
| 7,722,894 B2 | 5/2010 | Wang et al. |
| 7,931,651 B2 | 4/2011 | Webb et al. |
| 2001/0029956 A1 | 10/2001 | Argenta et al. |
| 2001/0043943 A1 | 11/2001 | Coffey |
| 2002/0065494 A1 | 5/2002 | Lockwood et al. |
| 2002/0082567 A1 | 6/2002 | Lockwood et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0143403 A1 | 10/2002 | Vaidyanathan et al. |
| 2002/0161317 A1 | 10/2002 | Risk et al. |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0040687 A1 | 2/2003 | Boynton |
| 2003/0050594 A1 | 3/2003 | Zamierowski |
| 2003/0108587 A1 | 6/2003 | Orgill et al. |
| 2003/0109855 A1 | 6/2003 | Solem et al. |
| 2003/0118692 A1 | 6/2003 | Wang et al. |
| 2003/0130599 A1 | 7/2003 | Restle et al. |
| 2003/0187367 A1 | 10/2003 | Odland |
| 2003/0208149 A1 | 11/2003 | Coffey |
| 2003/0219469 A1 | 11/2003 | Johnson |
| 2003/0225347 A1 | 12/2003 | Argenta |
| 2003/0225441 A1 | 12/2003 | Boynton |
| 2004/0006319 A1 | 1/2004 | Lina |
| 2004/0024351 A1 | 2/2004 | Greter |
| 2004/0030304 A1 | 2/2004 | Hunt |
| 2004/0039391 A1 | 2/2004 | Argenta |
| 2004/0039415 A1 | 2/2004 | Zamierowski |
| 2004/0064111 A1 | 4/2004 | Lockwood et al. |
| 2004/0064132 A1 | 4/2004 | Boehringer |
| 2004/0073151 A1 | 4/2004 | Weston |
| 2004/0122434 A1 | 6/2004 | Argenta |
| 2004/0167482 A1 | 8/2004 | Watson |
| 2004/0225178 A1 | 11/2004 | Kriewall |
| 2004/0225208 A1 | 11/2004 | Johnson |
| 2004/0249353 A1 | 12/2004 | Risks, Jr. et al. |
| 2004/0260230 A1 | 12/2004 | Randolph |
| 2005/0020955 A1 | 1/2005 | Sanders |
| 2005/0028828 A1 | 2/2005 | Heaton et al. |
| 2005/0043659 A1 | 2/2005 | Challis et al. |
| 2005/0063939 A1 | 3/2005 | Ameer et al. |
| 2005/0065484 A1 | 3/2005 | Watson, Jr. |
| 2005/0090787 A1 | 4/2005 | Risk, Jr. et al. |
| 2005/0101940 A1 | 5/2005 | Radl |
| 2005/0124966 A1 | 6/2005 | Karpowicz |
| 2005/0131327 A1 | 6/2005 | Lockwood et al. |
| 2005/0148913 A1 | 7/2005 | Weston |
| 2005/0165350 A1 | 7/2005 | Greter |
| 2005/0177190 A1 | 8/2005 | Zamierowski |
| 2005/0182445 A1 | 8/2005 | Zamierowski |
| 2005/0197645 A1 | 9/2005 | Karpowicz |
| 2005/0203452 A1 | 9/2005 | Weston |
| 2005/0209574 A1 | 9/2005 | Boehringer |
| 2005/0222527 A1 | 10/2005 | Miller |
| 2005/0222528 A1 | 10/2005 | Weston |
| 2005/0222544 A1 | 10/2005 | Weston |
| 2005/0228329 A1 | 10/2005 | Boehringer |
| 2005/0234510 A1 | 10/2005 | Zamierowski |
| 2005/0240220 A1 | 10/2005 | Zamierowski |
| 2005/0261615 A1 | 11/2005 | Weston |
| 2005/0261642 A1 | 11/2005 | Weston |
| 2005/0283105 A1 | 12/2005 | Heaton et al. |
| 2006/0025727 A1 | 2/2006 | Boehringer |
| 2006/0029650 A1 | 2/2006 | Coffey |
| 2006/0029675 A1 | 2/2006 | Ginther |
| 2006/0079852 A1 | 4/2006 | Bubb |
| 2006/0100586 A1 | 5/2006 | Karpowicz |
| 2006/0149170 A1 | 7/2006 | Boynton |
| 2006/0149171 A1 | 7/2006 | Vogel |
| 2006/0149176 A1 | 7/2006 | Bolam |
| 2006/0173253 A1 | 8/2006 | Ganapathy |
| 2006/0189910 A1 | 8/2006 | Johnson |
| 2006/0193888 A1 | 8/2006 | Lye et al. |
| 2006/0213527 A1 | 9/2006 | Argenta et al. |
| 2006/0263417 A1 | 11/2006 | Lelkes et al. |
| 2006/0286076 A1 | 12/2006 | Fleischmann |
| 2006/0293169 A1 | 12/2006 | Srinivasan et al. |
| 2007/0005028 A1 | 1/2007 | Risk, Jr. et al. |
| 2007/0014837 A1 | 1/2007 | Johnson |
| 2007/0021697 A1 | 1/2007 | Ginter |
| 2007/0021698 A1 | 1/2007 | Fleischmann |
| 2007/0032754 A1 | 2/2007 | Walsh |
| 2007/0071790 A1 | 3/2007 | Ameer et al. |
| 2007/0207179 A1 | 9/2007 | Andersen et al. |
| 2007/0208420 A1 | 9/2007 | Ameer et al. |
| 2007/0219585 A1 | 9/2007 | Cornet et al. |
| 2007/0233022 A1 | 10/2007 | Henley et al. |
| 2007/0260226 A1 | 11/2007 | Jaeb et al. |
| 2008/0112998 A1 | 5/2008 | Wang |
| 2008/0208147 A1 | 8/2008 | Argenta et al. |
| 2008/0208171 A1 | 8/2008 | Argenta |
| 2009/0093565 A1 | 4/2009 | Yang et al. |
| 2009/0148945 A1 | 6/2009 | Ameer et al. |

(56) References Cited

U.S. PATENT DOCUMENTS

| | | |
|---|---|---|
| 2009/0187259 A1 | 7/2009 | Argenta et al. |
| 2009/0325859 A1 | 12/2009 | Ameer et al. |
| 2010/0121229 A1 | 5/2010 | Argenta et al. |
| 2012/0215235 A1 | 8/2012 | Fogel |

FOREIGN PATENT DOCUMENTS

| | | |
|---|---|---|
| DE | 561757 | 10/1932 |
| DE | 847475 | 6/1952 |
| DE | 1963258 | 6/1971 |
| DE | 2809828 | 9/1978 |
| DE | 3102674 | 9/1982 |
| DE | 3539533 | 5/1987 |
| DE | 4037931 | 5/1992 |
| DE | 4111122 | 4/1993 |
| DE | 29504378 | 9/1995 |
| DE | 19722075 | 10/1998 |
| DK | 64055 | 10/1945 |
| EP | 0117632 | 9/1984 |
| EP | 0274898 | 7/1988 |
| EP | 0424165 | 4/1991 |
| EP | 0485657 | 5/1992 |
| EP | 0547496 | 6/1993 |
| EP | 0620720 | 10/1994 |
| EP | 0620720 B1 | 10/1994 |
| EP | 0620720 B2 | 10/1994 |
| EP | 0688189 | 12/1995 |
| EP | 0777504 | 6/1997 |
| EP | 0853950 | 7/1998 |
| EP | 0880953 | 12/1998 |
| EP | 0688189 | 9/2000 |
| EP | 1064958 | 1/2001 |
| EP | 1088569 | 4/2001 |
| EP | 1452191 | 9/2004 |
| FR | 500253 | 3/1920 |
| FR | 1303238 | 9/1962 |
| GB | 190203090 | 6/1902 |
| GB | 114754 | 4/1918 |
| GB | 641061 | 8/1950 |
| GB | 1273342 | 5/1972 |
| GB | 1457164 | 12/1976 |
| GB | 1549756 | 8/1979 |
| GB | 2195255 | 4/1988 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| JP | 1004629 | 1/1989 |
| JP | 06-048860 | 2/1994 |
| RU | 70627 | 2/2008 |
| SE | 84485 | 10/1935 |
| SU | 587941 | 1/1978 |
| SU | 1416108 | 7/1985 |
| SU | 1251912 | 8/1986 |
| SU | 1268175 | 11/1986 |
| WO | 80/01139 | 6/1980 |
| WO | 87/00439 | 1/1987 |
| WO | 87/04626 | 8/1987 |
| WO | WO 89/04158 | 5/1989 |
| WO | 90/00060 | 1/1990 |
| WO | 90/10424 | 9/1990 |
| WO | 9011795 | 10/1990 |
| WO | 9100718 | 1/1991 |
| WO | 9116030 | 10/1991 |
| WO | 9219313 | 11/1992 |
| WO | 9220299 | 11/1992 |
| WO | 93/09727 | 5/1993 |
| WO | 94/00090 | 1/1994 |
| WO | 94/20041 | 9/1994 |
| WO | 96/05873 | 2/1996 |
| WO | 96/15745 | 5/1996 |
| WO | 99/13793 | 3/1999 |
| WO | 99/51164 | 10/1999 |
| WO | 00/07653 | 2/2000 |
| WO | 00/15277 | 3/2000 |
| WO | 00/21586 | 4/2000 |
| WO | 00/26100 | 5/2000 |
| WO | 00/30567 | 6/2000 |
| WO | 00/32247 | 6/2000 |
| WO | 00/38552 | 7/2000 |
| WO | 00/38755 | 7/2000 |
| WO | 00/42958 | 7/2000 |
| WO | 00/59418 | 10/2000 |
| WO | 00/59424 | 10/2000 |
| WO | 00/61206 | 10/2000 |
| WO | 00/64394 | 11/2000 |
| WO | 01/34223 | 5/2001 |
| WO | 01/37922 | 5/2001 |
| WO | 01/49233 | 7/2001 |
| WO | 01/85248 | 11/2001 |
| WO | WO 01/89431 | 11/2001 |
| WO | WO 02/43634 | 6/2002 |
| WO | 03/005943 | 1/2003 |
| WO | 03028786 | 4/2003 |
| WO | 03/101385 | 12/2003 |
| WO | WO 03/101508 | 12/2003 |
| WO | 2005/028017 | 3/2005 |
| WO | 2005/046762 | 5/2005 |
| WO | 2005/102234 | 11/2005 |
| WO | 2006/046060 | 5/2006 |
| WO | 2007106589 | 9/2007 |
| WO | 2007106591 | 9/2007 |
| WO | 2008063281 | 5/2008 |
| WO | 2009/049058 | 4/2009 |
| WO | 2009/089435 | 7/2009 |
| WO | 2010009294 | 1/2010 |

OTHER PUBLICATIONS

Lee, S.S., et al., "Management of intractable sternal wound infections with topical negative pressure dressing", J. Card. Surg., 20(3):218-22 (May-Jun. 2005).

Jethwa, P., et al., "Using topical negative pressure therapy to resolve wound failure following perineal resection", J. Wound Care, 14(4):166-7 (Apr. 2005).

Banwell, P.E., et al., "Topical negative pressure therapy: mechanisms and indications", Int. Wound J., 1(2):95 (15 pages) (Jun. 2004).

Melano, E., et al., "The effects of Panafil when using topical negative pressure to heal an infected sternal wound," J. Wound Care, 13(10):425-6 (Nov. 2004).

Morton, N., "Use of topical negative pressure therapy in postoperative dehisced or infected wounds", J. Wound Care, 13(8):346-8 (Sep. 2004).

Moisidis, E., et al., "A prospective, blinded, randomized, controlled clinical trial of topical negative pressure use in skin grafting", Plast. Reconstr. Surg., 114(4):917-22 (7 sheets) (Sep. 15, 2004).

Tachi, M., et al., "Topical negative pressure using a drainage pouch without foam dressing for the treatment of undetermined pressure ulcers", Ann. Plast. Surg., 53(4):338-42 (7 sheets) (Oct. 2004).

Jones, S.M., et al., "Complications of topical negative pressure therapy in small-diameter wounds", Plast. Reconstr. Surg., 114(3):815-817 (5 sheets) (Sep. 1, 2004).

Loree, S., et al., "Is vacuum assisted closure a valid technique for debriding chronic leg ulcers?" J. Wound Care, 13 (6):249-52 (Jun. 2004).

Vogt, P.M., et al., "Several aspects of foam materials and their possible interactions with the wound surface in the vacuum therapy", Zentralbl. Chir., (English abstract on first page, 1 sheet printout from PubMed); 129 Suppl 1:S92-S94 (May 2004).

Haslik, W., et al., "The use of subatmospheric pressure to prevent burn wound progression: first experiences in burn wound treatment", Zentralbl. Chir., (English abstract on first page, and 1 sheet printout from PubMed); 129 Suppl. 1: S62-63 (May 2004).

Steenvoorde, P., et al., "Combining topical negative pressure and a Bogota bag for managing a difficult laparostomy", J. Wound Care, 13(4):142-3 (Apr. 2004).

(56) References Cited

OTHER PUBLICATIONS

Pullen, R., "Treatment of pressure sores in elderly patients", Z. Genrontol. Geriatr., (English abstract on first page, 1 sheet printout from PubMed); 37(2):92-9 (Apr. 2004).
Gottrup, F., "Optimizing wound treatment through health care structuring and professional education", Wound Repair Regen., 12(2):129-33 (Mar.-Apr. 2004).
(Anon.) "New best practice guidelines for managing pressure ulcers with negative pressure wound therapy published", Home Healthcare Nurse, 23(7):469 (one sheet) (Jul. 2005).
Stechmiller, J.K., et al., "Effect of negative pressure wound therapy on the expression of TNF-alpha, IL-1beta, MMP-2, MMP-3, and TIMP-1 in wound fluids of adults with pressure ulcers", Wound Repair Regen., 13(2):A16 (Mar.-Apr. 2005).
Snyder, R.J., "Negative pressure wound therapy (NPWT)/ vacuum-assisted closure® (VAC®) as an adjunct in the treatment of pyoderma gangrenosum", Wound repair and regeneration, 13:A29 (Mar. 2005).
Armstrong, D.G., et al., "Negative pressure wound therapy in treatment of diabetic foot wounds: a marriage of modalities", Ostomy Wound Manage., 50(4A suppl):9-12 (Apr. 2004).
Armstrong, D.G., et al., "Plantar pressure changes using novel negative pressure wound therapy technique", J. Am. Podiatr. Med. Assoc., 94(5):456-60 (Sep.-Oct. 2004).
Baharestani, M.M., "Negative pressure wound therapy: An examination of cost-effectiveness", Ostomy Wound Manage., 50(11A suppl):29S-335 (Nov. 2004).
Bernstein, B.H., et al., "Combination of subatmospheric pressure dressing and gravity feed antibiotic instillation in the treatment of post-surgical diabetic foot wounds: a case series," parts 1 and 2, Wounds, 17(2):37-48 (23 sheets) (Feb. 2005).
Datiashvili, R.O., et al., "Negative pressure dressings: An alternative to free tissue transfers?" Wounds, 17 (8):206-212 (Aug. 2005).
De Leon, J., "Negative pressure wound therapy in pressure ulcer management", Ostomy Wound Manage., 51(2A suppl):3S-8S (Feb. 2005).
Dobke, M.K., et al., "A novel approach to acute infection of the glenohumeral joint following rotator cuff repair—a case series", Wounds, 17(6):137-40 (6 sheets) (Jun. 2005).
Dunbar, A., et al., "Addressing the pain: Silicone net dressings as an adjunct with negative pressure wound therapy", Ostomy Wound Manage., 51(4):18-20 (4 sheets) (Apr. 2005).
Etoz, A., et al., "The use of negative pressure wound therapy on diabetic foot ulcers: A preliminary controlled trial", Wounds, 16(8):264-9 (Aug. 2004).
Fife, C.E., et al., "Healing dehisced surgical wounds with negative pressure wound therapy", Ostomy Wound Manage., 50(4A suppl):28-31 (Apr. 2004).
Geller, S.M., et al., "Ulceration of pyoderma gangrenosum treated with negative pressure wound therapy", J. Am. Podiatr. Med. Assoc., 95(2):171-4 (Mar.-Apr. 2005).
Gray, M., et al., "Is negative pressure wound therapy effective for the management of chronic wounds?" J. Wound Ostomy Continence Nurs., 31(3):101-5 (May-Jun. 2004).
Gupta, S., et al., "A literature review of negative pressure wound therapy", Ostomy Wound Manage., 50(11A suppl):2S-4S (Nov. 2004).
Gupta, S., et al., "The perioperative use of negative pressure wound therapy in skin grafting", Ostomy Wound Mangage., 50(4A suppl):32-4 (Apr. 2004).
Gupta, S., et al., "Guidelines for managing pressure ulcers with negative pressure wound therapy", Adv. Skin Wound Care, 17(Suppl 2):1-16 (Nov.-Dec. 2004).
Huljev, D., et al., "Necrotizing fasciitis of the abdominal wall as a post-surgical complication: a case report", Wounds, I7(7):169-77 (10 sheets) (2005) (Posted Aug. 11, 2005).
Kaplan, M., "Negative pressure wound therapy in the management of abdominal compartment syndrome", Ostomy Wound Manage., 51(2A suppl):29S-35S (Feb. 2005).

Mendez-Eastman, S., "Determining the appropriateness of negative pressure wound therapy for pressure ulcers", Ostomy Wound Manage., 50(4A suppl):13-16 (Apr. 2004).
Mendez-Eastman, S., "Using negative-pressure for positive results", Nursing, 35(5):48-50 (May 2005).
Miller, M.S., et al., "Negative pressure wound therapy: 'A rose by any other name'", Ostomy Wound Manage., 51 (3):44-9 (11 sheets) (Mar. 2005).
Niezgoda, J.A., et al., "The economic value of negative pressure wound therapy", Ostomy Wound Manage., 51 (2A suppl):44S-47S (Feb. 2005).
Niezgoda, J.A., "Combining negative pressure wound therapy with other wound management modalities", Ostomy Wound Manage., 51(2A suppl):S36-8 (Feb. 2005).
Orgill, D.P., et al., "Guidelines for treatment of complex chest wounds with negative pressure wound therapy", Supplement B to Wounds: A Compendium of Clinical Research and Practice, (24 sheets) (Dec. 2004).
Orgill, D.P., "Utilizing negative pressure wound therapy on open chest/sternotomy wounds", Ostomy Wound Manage., 50(11A suppl):15S-17S (Nov. 2004).
Orgill, D.P., "Advancing the treatment options of chest wounds with negative pressure wound therapy", Ostomy Wound Manage., 51(2A suppl):39S-43S (Feb. 2005).
Page, J.C., et al., "Retrospective analysis of negative pressure wound therapy in open foot wounds with significant soft tissue defects", Adv. Skin Wound Care, 17(7):354, 356, 358-60, 362-64 (Sep. 2004).
Page, J.C., et al., "Negative pressure wound therapy in open foot wounds with significant soft tissue defects", Ostomy Wound Manage., 51(2A suppl):9S-14S (Feb. 2005); excerpted from Page, J.C., et al., "Retrospective analysis of negative pressure wound therapy in open foot wounds with significant soft tissue defects", Adv. Skin & Wound Care, 17(7):354-364, (2004).
Pattison, P.S., et al., "Case report: Using dual therapies—Negative pressure wound therapy and modified silicone gel liner—to treat a limb postamputation and dehiscence", Wounds, 17(8):233-40 (11 sheets) (Aug. 2005).
Ratliff, C.R., "Negative-pressure wound therapy. Adjunct relief for chronic wounds", Adv. Nurs. Pract., 12(7):47-9 (3 sheets) (Jul. 2004) (Issue date: Jul. 1, 2004).
Sarsam, S.E., et al., "Management of wound complications from cesarean delivery," Obstet. Gynecol. Surv., 60 (7):462-73 (Jul. 2005).
Schaum, K.D., "Payment perspective: Negative pressure wound therapy pumps and ostomy supplies", Ostomy Wound Manage., 51(3):20-22 (2 sheets) (Mar. 2005).
Simman, R., et al., "A comparative histological study of skin graft take with tie-over bolster dressing versus negative pressure wound therapy in a pig model: a preliminary study [brief communication]", Wounds, 16(2):76-80 (7 sheets) (Feb. 2004).
Milner, R.H., et al., "Plasticized polyvinyl chloride film as a primary burns dressing: a microbiological study," Burns, 14(1):62-65 (1988).
Wilson, G., et al., "Plasticised polyvinylchloride as a temporary dressing for burns," Br. Med. J., 294:556-557 (Feb. 1987).
Hunsaker, R.H., Correspondence and Brief Communications—"Polyvinylchloride for increasing take of skin grafts," Plast. Reconstr. Surg. 82:193 (Jul. 1988).
3M™ Inzisionsfolien—Produktubersicht, by 3M Medica, 6 annotated sheets.
Application for rationalization proposal, proposal entitled "Variant for vacuum treatment of purulent wounds," (4 sheets in English, 4 sheets in Russian, certificate of translation dated May 8, 2009), proposal allegedly executed Dec. 25, 1985 (Bagautdinov III).
Buschbaum, H.J., ed., et al., Strategies in Gynecologic Surgery, pp. 203, Springer-Verlag, NY, (1986).
Flynn, J-B. McC., et al., Technological Foundations in Nursing, pp. 506-507, Appleton & Lange, Norwalk, CT, (1990).
Gomco Mobile constant and intermittent model 6030 & 6031, Operation, Maintenance and Service Manual, with annotations, 21 sheets, (Jan. 1987).
Kahlson, G., et al., "Wound healing as dependent on rate of histamine formation," The Lancet, pp. 230-234, (Jul. 30, 1960).

(56) References Cited

OTHER PUBLICATIONS

Karev, I.D., et al., "Foam drainage system for treating purulent wounds," pp. 87-88, (2 sheets English translation, 2 sheets Russian and certifcation of translation dated Apr. 6, 2009) (allegedly dated 1986).
Kozier, B., et al., Techniques in Clinical Nursing, 3d ed., pp. 559-560, pp. 603-605, Addison-Wesley Publishing Company, Inc., Health Sciences, Redwood City, CA, (1989).
McLean, W. C., "The role of closed wound negative pressure suction in radial surgical procedures of the head and neck," The Laryngoscope, 74(1)70-94, (Jan. 1964).
Norton, B.A., et al., Skills for Professional Nursing Practice: communication, physical appraisal, and clinical techniques, pp. 298-302, pp. 328-329, Appleton-Century-Crofts, Norwalk, CT (1986).
Bagautdinov, N.A., Report on Practical Application entitled "Variant of vacuum treatment of purulent wounds," Kazan Municipal Hospital No. 8, (1 sheet in English, 1 sheet in Russian and certificate of translation dated May 8, 2009), (allegedly dated Dec. 24, 1985). (Practical Report I).
Kuznetsov, V.A. et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009) (allegedly dated May 19, 1986). (Practical Report II).
Bagautdinov, N.A., Report on Practical Application entitled "Method of vacuum treatment of open purulent wounds," Medical-Sanitary Ward of the Arzamas Instrument Plant, (1 sheet in English, 1 sheet in Russian and certificate of translation dated Apr. 27, 2009) (allegedly dated 1986).(Practical Report III).
Roth, B., et al., "Ubersichtsarbeit: Indication for suction-rinse drainage and hygienic certainty in drainages," GMS Krankenhaushyg. Interdiszip, 1(1):Doc27 (7 sheets in German with English abstract on first sheet) (2006).
Schneider, F.R., Handbook for the Orthopaedic Assistant, 2nd ed., pp. 185, The C.V. Mosby Company, St. Louis, (1976).
Thomas, S., Wound Management and Dressings, Chapter 4: Semipermeable film dressings (continued onto pp. 26-34), Chapter 5: Foam dressings (continued onto pp. 36-42), and pp. 166, The Pharmaceutical Press, London, (1990).
Witkowski, J.A., et al., "Synthetic dressings: wound healing in the 80's," (5 sheets), Hospital Therapy, (Nov. 1986).
Excerpts from Bier's Hyperemic Treatment, pp. 17-25, 44-46, 90-96, 167-170, 210-211 (1909).
Leaper, D.J., "The Wound Healing Process," Advances in Wound Management, T.D. Turner, et al., eds., pp. 7-16, New York: John Wiley and Sons, (1986).
Kohlman, P., et al., "Pouching Procedure to Collect Drainage From Around a Biliary Drainage Catheter", Ostomy/Wound Management, Nov./Dec. 1991, pp. 47-50, V. 37.
Alper, J., "Recent Advances in Moist Wound Healing", Southern Medical Journal, Nov. 1986, pp. 1398-1404, V. 79, N.11.
Reid, D., "Information on Cupping or Using Suction Cups on Wounds and for Healing Purposes", from Chines Herbal Medicine (2 pages).
Sheppard, M.D., "Sealed drainage of wounds," The Lancet, Jun. 14, 1952, pp. 1174-1176.
Putney, F., "The Use of Continuous Negative Pressure After Laryngectomy and Radical Neck Dissection", Surgery, Gynecology & Obstetrics, Aug. 1956, pp. 244-246.
Pleupump MK II, printouts from websites, www.xenamedical.se and www.landstinget.sormland.se, Aug. 14, 2001 (12 pages).
"Wound Suction; Better Drainage With Fewer Problems", Nursing75, October, pp. 52-55 (1975).
Grams Aspirator, et al., Grams Medical, catalog pages (3 pages) (prices as of Aug. 1991 and Sep. 1992).
Medela Dominant promotional literature (2 pages of photos) (labeled circa 1984-1985).
Engdahl, O., et al., "Quantification of Aspirated Air Volume Reduces Treatment Time in Pneumothorax", Eur Respir J., 1990, 3, pp. 649-652.
Usage Manual Pleurasug TDR (2 pages of diagrams with descriptions).
Spengler, M., et al., "Performance of Filtered Sump Wound Drainage Tubes", Surgery, Gynecology & Obstetricsq, Mar. 1982, pp. 333-336, vol. 154.
Hallstrom, B., et al., "Postoperative Course After Total Hip Arthroplasty: Wound Drainage Versus No Drainage", Orthopaedic Review, Jul. 1992, pp. 847-851.
Miles, W., et al., "A Method of Performing Abdominoperineal Excision for Carcinoma of the Rectum and of the Terminal Portion of the Pelvic Colon", The Lancet, Dec. 19, 1908, pp. 1812-1813.
Benjamin, P., "Faeculent Peritonitis: A Complication of Vacuum Drainage", Br. J. Surg., 1980, pp. 453-454, vol. 67.
Sagi, A., et al., "Burn Hazard From Cupping—An Ancient Universal Medication Still in Practice", Burns, 1988, pp. 323-325, vol. 14, No. 4.
Agrama, H., et al., "Functional Longevity of Intraperitoneal Drains", The American Journal of Surgery, Sep. 1976, pp. 418-421, vol. 132.
Magee, C., et al., "Potentiation of Wound Infection by Surgical Drains", The American Journal of Surgery, May 1976, pp. 547-549, vol. 131.
Birdsell, D., et al., "The Theoretically Ideal Donor Site Dressing",Annals of Plastic Surgery, Jun. 1979, pp. 535-537, vol. 2, No. 6.
Cruse, P., et al., "A Five-Year Prospective Study of 23,649 Surgical Wounds", Surgical Wounds/Cruse and Foord, Aug. 1973, pp. 206-210, vol. 107.
Aubrey, D., et al., "Treatment of the Perineal Wound After Proctectomy by Intermittent Irrigation", Arch. Surg., Oct. 1984, pp. 1141-1144, vol. 119.
Mayo, C., "The One-Stage Combined Abdominoperineal Resection for Carcinoma of the Rectum, Rectosigmoid and Sigmoid", Surgical Clinics of North America, Aug. 1939, pp. 1011-1019.
Draper, J., "Make the dressing fit the wound", Nursing Times, Oct. 9, 1985, pp. 32-35.
Schumann, D., et al., "Preoperative Measures to Promote Wound Healing", Nursing Clinics of North America, Dec. 1979, pp. 683-699, vol. 14, No. 4.
Besst, J., et al., "Wound Healing—Intraoperative Factors", Nursing Clinics of North America, Dec. 1979, pp. 701-712, vol. 14, No. 4.
Cooper, D., et al., "Postsurgical Nursing Intervention as an Adjunct to Wound Healing", Nursing Clinics of North America, Dec. 1979, pp. 713-726, Nursing Clinics of North America, vol. 14, No. 4.
O'Byrne, C., "Clinical Detection and Management of Postoperative Wound Sepsis", Nursing Clinics of North America, Dec. 1979, pp. 727-741, vol. 14, No. 4.
Keith, C., "Would Management Following Head and Neck Surgery", Nursing Clinics of North America, Dec. 1979, pp. 761-778, vol. 14, No. 4.
Tenta, L., et al., "Suction Drainage of Wounds of the Head and Neck", Surgery, Gynecology. & Obstetrics, Dec. 1989, p. 558, vol. 169.
Firlit, C., et al., "Surgical Wound Drainage: A Simple Device for Collection", journal of Urology, Aug. 1972, pp. 327, vol. 108.
Moloney, G., "Apposition and Drainage of Large Skin Flaps", Oxford, England, pp. 173-179 (Feb. 1957).
Worth, M., et al., "The Effectiveness of Bacterial Filtration in Vented Wound Drains", Journal of Surgical Research, 1979, pp. 405-407, 27.
Flynn, M., et al., "Promoting Wound Healing: Wound Healing Mechanisms", American Journal of Nursing, Oct. 1982, pp. 1544-1558.
Miles, W., "Technique of the Radical Operation for Cancer of the Rectum", The British Journal of Surgery, 1914-1915, pp. 292-305.
Hilton, P., "Surgical Wound Drainage: A Survey of Practices Among Gynaecologists in the British Isles", British Journal of Obstetrics and Gynaecology, Oct. 1988, pp. 1063-1069, vol. 95.
Milsom, I., et al., "An Evaluation of a Post-Operative Vacuum Drainage System", Current Medical Research and Opinion, 1979, pp. 160-164, vol. 6, No. 2.
Fox, J., et al., "The Use of Drains in Subcutaneous Surgical Procedures", The American Journal of Surgery, Nov. 1976, pp. 673-674, vol. 132.

(56) References Cited

OTHER PUBLICATIONS

Hilsabeck, J., "The Presacral Space as a Collector of Fluid Accumulations Following Rectal Anastomosis", American Society of Colon and Rectal Surgeons, (Oct. 1982), pp. 680-684, vol. 25, No. 7.
Hulten, L., et al., "Primary Closure of Perineal Wound After Protocolectomy or Rectal Excision", Acta Chir Scand 137, 1971, pp. 467-469.
Landes, R., "An Improved Suction Device for Draining Wounds", Arch. Surg., May 1972, pp. 707, vol. 104.
Hugh, T., "Abdominal Wound Drainage", The Medical Journal of Australia, May 4, 1987, pp. 505.
Eisenbud, D., "Modern Wound Management", Adadem Publishing, pp. 109-116 (Jan. 1999).
Eaglstein, W., et al., "Wound Dressings: Current and Future", Clinical and Experimental Approaches to Dermal and Epidermal Repair; Normal and Chronic Wounds, Progress in Clinical and Biological Research, vol. 365, © 1991 Wiley-Liss, Inc., pp. 257-265.
Bruno, P., "The Nature of Wound Healing", Nursing Clinics of North America, Dec. 1979, pp. 667-682, vol. 14, No. 4.
Bar-El, Y., et al., "Potentially Dangerous Negative Intrapleural Pressures Generated by Ordinary Pleural Drainage Systems", Chest, Feb. 2001, pp. 511-514, vol. 119, No. 2.
Agarwala, S., et al., "Use of Mini-Vacuum Drains in Small Surgical Wounds", Plastic and Reconstructive Surgery, Apr. 1998, pp. 1421-1422, vol. 101, n. 5.
Nasser, A., "The Use of the Mini-Flap Wound Suction Drain in Maxillofacial Surgery", Annals of the Royal College of Surgeons of England, 1986, pp. 151-153, vol. 68.
Hunt, T.K., et al. eds., "Dead Space" and "Drainage", Fundamentals of Wound Management, pp. 416-447 (1979).
Lumley, J., et al., "The Physical and bacteriological Properties of Disposable and Non-Disposable Suction Drainage Units in the Laboratory", Br. J. Surg., 1974, pp. 832-837, vol. 61.
Britton, B., et al., "A Comparison Between Disposable and Non-disposable Suction Drainage Units: A Report of a Controlled Trial", Br. J. Surg., 1979, pp. 279-280, vol. 66.
McFarlane, R., "The use of Continuous Suction Under Skin Flaps", British Journal of Plastic Surgery, pp. 77-86 (1958-1959).
Fay, M., "Drainage Systems: Their Role in Wound Healing", AORN Journal, Sep. 1987, pp. 442-455, vol. 46, No. 3.
Taylor, V., "Meeting the Challenge of Fistulas & Draining Wounds", Nursing80, June, pp. 45-51.
Orgill, D., "Curent Concepts and Approaches to Would Healing", Critical Care Medicine, Sep. 1988, pp. 899-908, vol. 16, No. 9.
Part III. Resolving Selected Clinical Dilemmas, pp. 17-20.
"Making Sense of Wound Drainage", Nursing Times, Jul. 5, 1989, pp. 40-42, vol. 85, No. 27.
Manualectric Breastpump, Catalog pages (4 pages), diagrams and descriptions.
Harkiss, K., "Leg Ulcers Cheaper in the Long Run", Community Outlook, Aug. 1985, pp. 19, 21, 22, 24 & 26.
Westaby, S. (Editor), "Wound Care No. 43; Which Dressing and Why", Nursing Times Jul. 21, 1982, pp. 41-44.
OpSite Wound Dressings, "Do Your Pressure Sore Dressings Shape Up to the OpSite Standard", 2 pages of advertisements.
Dow Corning Silastic® Foam Dressing: A New Concept in the Management of Open Granulating Wounds, 2 pages of advertisements.
Cobb, J., "Why Use Drains", The Journal of Bone and Joint Surgery, Nov. 1990, pp. 993-995, vol. 72-B, No. 6.
PLEUR$_x$ Pleural Catheter, Denver Biomedical, 4 pages of brochure.
Silvis, R., et al., "The Use of Continuous Suction Negative Pressure Instead of Pressure Dressing", Annals of Surgery, Aug. 1955, pp. 252-256, vol. 142, No. 2.
Van Way, C., "Prevention of Suction-Induced Gastric Mucosal Damage in Dogs", Gastric Suction, 1987, pp. 774-777, vol. 15, No. 8.
Moserova, J., "The Healing and Treatment of Skin Defects", pp. 103-151 (1989).
Rabkin, J., et al., "Infection and Oxygen", Problem Wounds: The Role of Oxygen, pp. 1-15 (1987).

Paradise Valley Hospital, The Center for Wound Healing and Hyperbaric Medicine, 3 pages of brochure.
DuoDERM Hydroactive™ Dressing, "In wound management—Now, a proven environment for fast healing", 1 page advertisement.
Howmedica porto-vac®, "Gentle, Steady Wound Drainage", 1 page advertisement.
Silicone from CUI (Cox-Uphoff International), "Flexability", 1 page advertisement.
Curtin, L., "Wound Management: Care and Cost—An Overview", Nursing Management, Feb. 1984, pp. 22-25, vol. 15.
Grabowski, S., "Leczenie ran z zastosowaniem podcisnienia", article, pp. 19-21, English abstract on p. 21 and 1 sheet printout from PubMed, (Jan. 1, 1964).
Royle, G., et al., "Disposable Drains", Annals of the Royal College of Surgery of England, 1984, 1 pages, vol. 66.
Meehan, P., "Open Abdominal Wounds: A Creative Approach to a Challenging Problem", Pregressions, 1992, pp. 3-8, 11, vol. 4, No. 2.
Stansby, G., et al., "Vacuum Drainage of Groin Wounds After Vascular Surgery", Br. J. Surg., Oct. 1990, pp. 1194-1195, vol. 77, No. 10.
Edlich, R., et al., "Evaluation of a New, Improved Surgical Drainage System", The American Journal of Surgery, Feb. 1985, pp. 295-298, vol. 149.
Broader, J., et al., "Management of the Pelvic Space After Proctectomy", Br. J. Surg., 1974, pp. 94-97, vol. 61.
Ayoub, M., et al., "A study of cutaneous and intracompartmental limb pressures associated with the combined use of tourniquets and plaster casts", May 1986, pp. 497, vol. 68-B, No. 3.
Cooper, D., "Optimizing Wound Healing: A Practice Within Nursing's Domain", Nursing Clinics of North America, Mar. 1990, pp. 165-180, vol. 25, No. 1.
Cooper, D., "Wound Healing", Nursing Clinics of North America, pp. 163-164 (Mar. 1990).
Hollis, H., et al., "A Practical Approach to Wound Care in Patients With Complex Enterocutaneous Fistulas", Surgery, Gynecology & Obstetrics, Aug. 1985, pp. 178-180, vol. 161.
Fingerhut, A., "Passive vs. Closed Suction Drainage After Perineal Would Closure Following Abdominoperineal Rectal Excision for Carcinoma", Dis Colon Rectum, Sep. 1995, pp. 926-932, vol. 38, No. 9.
Cook Pneumothorax Catheter Set, Wayne Pneumothorax Catheter Set, Emergency Medicine, Videotape advertisement.
Schaffer, D., "Closed Suction", Nursing97, Nov., http://www.springnet.com, pp. 62-64.
Carroll, P., "The Principles of Vacuum and Its Use in the Hospital Environment", Ohmeda, pp. 1-30 and cover sheet.
Healing of Full Thickness Defects in Swine.
Webster, J.G., "Prevention of Pressure Sores", © IOP Publishing Ltd 1991, The Adam Hilger Series on Biomedical Engineering, pp. 199-223.
Garcia-Velasco, M., et al., "Compression Treatment of Hypertrophic Scars in Burned Children", The Canadian Journal of Surgery, V.21, No. 5, Sep. 1978, pp. 450-452.
Rose, M.P., et al., "The Clinical Use of a Tubular Compression Bandage, Tubigrip, for Burn-Scar Therapy: A Critical Anaylis", Burns (1985) 12, 58-64.
Murray, Y., "Tradition Rather Than Cure", Wound Care, Nursing Times, Sep. 21, vol. 84, No. 38, 1988.
Spurlock, Gareth, "The Management of Open Joint Injuries", Wound Management, Veterinary Clinics of North American Equina Practice, vol. 5, No. 3, Dec. 1989.
Tittel, K., et al., "VariDyne—new standards in postoperative wound drainge", Jahrgang 14 (1988), Nr. 2, April, vol. 14 (1988), No. 2, April, pp. 104-107.
Queen, D., et al., "The preclinical evaluation of the Water Vapour Transmission Rate Through Burn Wound Dressings", Biomaterials 1987 vol. 8, September, pp. 367-371.
Wood, R.A.B., et al., "Foam Elastomer Dressing in the Management of Open Granulating Wounds: Experience with 250 Patients", Br. J. Surg., vol. 64 (1977), pp. 554-557.
Waymack, J.P., et al., "An Evaulation of Aquaphor Gauze Dressing in Burned Children", Burns (1986) 12, 443-448.

(56) References Cited

OTHER PUBLICATIONS

Winter, George D., "Epidermal Wound Healing Under a New Polyurethane Foam Dressing (Lyofoam)", Plastic & Reconstructive Surgery, Nov. 1975, Vo. 56, No. 5, pp. 531-537.
Svedman, P., "A dressing allowing continuous treatment of a biosurface," IRCS Medical Science: Biomedical Technology; Clinical Medicine; Surgery and Transplantation, 7:221 (1979), with annotations.
Viljanto, J., "A new method for treatment of open wounds", Ann. Chir. Gynaecol. Fenn., (English abstract on first page, and 1 sheet printout from PubMed); 60:94-100 (1972).
Yusupov, Y.N., et al., "Active drainage of wounds", Vestn. Khir. Im. I.I. Grek., (with English abstract on last page, 5 sheets of English translation, 3 pp. of English translation by BlueSky publishing and 1 sheet printout from PubMed); 138(4):42-46 (Apr. 1987).
Alexander, J.W., et al., "Clinical evaluation of epigard, a new synthetic substitute for homograft and heterograft skin," J. of Trauma, 13:374-383, (1973).
Anon., "Standard Test Methods for Water Vapor Transmission of Materials," ASTM, Designation: E 96/E 96M-05, Published Jun. 2005, 11 sheets, (Exhibit D-184).
Byers, R.M., "Clinical effects of closed suction drainage on wound healing in patients with head and neck cancer," Arch. Otolaryngol., vol. 108:723-6, (Nov. 1982).
Cesany, P., "Suction in the Treatment of Torpid Ulcerations," Rozhledy v chirurgii, 48-9, MINC022894-MINC022898, cover sheet and pp. 406-409 English abstract on p. 409 (1 sheet printout from PubMed) (Sep. 1969).
Chinn, S.D., "Closed wound suction drainage," J. Foot Surg., vol. 24: 76-81, (Jan.-Feb. 1985).
Email dated Jan. 14, 2002 with attachments, including "Report of Meeting with DG Consulting" dated Jan. 10, 2002, 5 sheets, (Exhibit D-157).
Westaby, S., "Treatment of purulent wounds and fistulae with an adhesive wound irrigation device," Annals of the Royal College of Surgeons, vol. 63: 353-6 (1981).
Hartz, R.R., et al., "Healing of the Perineal Wound," Arch. Surg., vol. 115, 471-474, (1980), (Exhibit D-395).
Mizuno, K., "Suctioning Sponge," Arch. Opthalmol., vol. 101:294, (Feb. 1983).
Nikolov, A., "Method of treatment of postphlebitic and varicose trophic ulcers on the lower extremities by vacuum [Vacuum treatment method in postphlebitic and varicose trophic ulcers of the lower extremities]," Khirurgiia, pp. 368-374, (English abstract on p. 371 and 1 sheet printout from PubMed) (1981).
Smith, S.R.G., "Surgical drainage", Br. J. Hosp. Med., 33(6):308-315 (Jun. 1985).
Svedman, "A dressing system providing fluid supply and suction drainage used for continuous or intermittent irrigation," Ann. Plast. Surg., vol. 17, 9 pages, (Aug. 1986).
Svedman, "Irrigation treatment in split thickness skin grafting of intractable leg ulcers," Scand. J. Plast. Reconstr. Surg., vol. 19:211-213, (1985).
Labler, L., et al., "Wound conditioning by vacuum assisted closure (V.A.C.) in postoperative infections after dorsal spine surgery," Eur. Spine J., 15 (9): 1388-1396 (Sep. 2006).
Tauro, L.F., et al., "A comparative study of the efficacy of topical negative pressure moist dressings and conventional moist dressings in chronic wounds," Indian J. Plast. Surg. 40(2):133-140 (Jul.-Dec. 2007).
Ramnarine, I.R., et al., "Vacuum-assisted closure in the paediatric patient with post-cardiotomy mediastinitis", Eur. J. Cardiothorac. Surg., 22:1029-31 (Dec. 2002).
Rollins, H., "Hypergranulation tissue at gastrostomy sites", J. Wound Care, 9(3):127-129 (Mar. 2000).
Schaum, K.D., "Medicare Part B negative pressure wound therapy pump policy. A partner for Medicare Part A PPS," Home Healthc. Nurse, 20(1):57-8 (Jan. 2002).

Shaer, W.D., "Inexpensive vacuum-assisted closure employing a conventional disposable closed-suction drainage system", Plast. Reconstr. Surg., 107(1):292-3 (Jan. 2001).
Saklani, A.P., et al., "Vacuum assisted closure system in the management of enterocutaneous fistula", Postgrad. Med. J., 78(925):699 (Nov. 2002).
Takei, T., et al., "Molecular basis for tissue expansion: clinical implications for the surgeon", Plast. Reconstr. Surg., 102(1):247-258 (Jul. 1998).
Tang, A.T.M., et al., "Vacuum-assisted closure to treat deep sternal wound infection following cardiac surgery", J. Wound Care, 9(5):229-30 (May 2000).
Nikkhah, C., et al., "Re: use of specialized bone screws for intermaxillary fixation", Ann. Plast. Surg., 47(1): 93, (Jul. 2001).
Voinchet, V., et al., "Vacuum assisted closure. Wound healing by negative pressure", Ann. Chir. Plast. Esthet., (English abstract on first page, and 1 sheet printout from PubMed); 41(5):583-9, (Oct. 1996).
Von Gossler, C.M., et al., "Rapid aggressive soft-tissue necrosis after beetle bite can be treated by radical necrectomy and vacuum suction-assisted closure", J. Cutan. Med. Surg., 4(4):219-222 (Oct. 2000).
Wilhelmi, B.J., et al., "Creep vs. stretch: a review of the viscoelastic properties of skin", Ann. Plast. Surg., 41(2):215-219, (Aug. 1998).
Wiseman, J., et al., "Aesthetic aspects of neurofibromatosis reconstruction with the vacuum-assisted closure system", Aesth. Plast. Surg., 25:326-31 (Sep.-Oct. 2001).
Young, T., "Common problems in wound care: overgranulation", Br. J. Nursing, 4(3):169-170, (Feb. 9-22, 1995).
Ziegler, U.E., et al., "Skin substitutes in chronic wounds", Zentralbl. Chir., (English abstract on first page; 1 sheet printout from PubMed); 126 Suppl 1:71-4 (2001).
Stannard, J., "Complex orthopaedic wounds: prevention and treatment with negative pressure wound therapy", Orthop. Nurs., 23 Suppl 1:3-10 (10 sheets) (Mar.-Apr. 2004), presented at the 17th Annual Clinical Symposium on Advances in Skin & Wound Care, Dallas, TX (Sep. 23, 2002).
Patel, C.T.C., et al., "Vacuum-assisted wound closure: changing atmospheric pressure assists wound healing," AJN, 100:45-47 (2000).
Masters, J., "Reliable, inexpensive and simple suction dressings", Letters to the Editor, p. 267, labeled 1998.
Hazelbag, S., et al., "Cytokine profile of cervical cancer cells", Gynecol. Oncol., 83(2):235-243, (Nov. 2001).
Beitz, J.M., et al., "Abdominal wound with enterocutaneous fistula: a case study", J. Wound Ostomy Continence Nurs., 25(2):102-6, (Mar. 1998).
Baxandall, T., "Healing cavity wounds with negative pressure", Elderly Care, 9(1):20, 22 (Feb.-Mar. 1997).
McKinney, P.E., "Out-of-hospital and interhospital management of crotaline snakebite", Ann. Emerg. Med., 37(2):168-174, (Feb. 2001).
Leroy, S.C., et al., "Severe penile erosion after use of a vacuum suction device for management of erectile dysfunction in a spinal cord injured patient. Case report", Paraplegia, 32(2):120-123 (Feb. 1994).
Defranzo, A.J., et al., "Vacuum assisted closure of the abdominal wall", 73rd Annual Meeting, American Association of Plastic Surgeons, Philadelphia, PA (2004), 1 sheet of abstract.
Argenta, L.C., et al., "The V.A.C. as an adjunct for treatment for abdominal wounds", 66th Annual Meeting of the American Society of Plastic and Reconstructive Surgeons, San Francisco, CA, pp. 330-331; 1 sheet of abstract (Sep. 21-24 1997).
Argenta, L.C., et al., "Vacuum assisted closure of chronic wounds", 65th Annual Scientific Meeting, American Society of Plastic and Reconstructive Surgeons, Dallas, TX, pp. 226-227; 1 sheet of abstract (Nov. 9-13, 1996).
Defranzo, A.J., et al., "The use of V.A.C. therapy for treatment of lower extremity wounds with exposed bone", 68th Annual Meeting of the American Society of Plastic and Reconstructive Surgeons, New Orleans, LA, pp. 37-38; 2 sheets of abstract (Oct. 24-27, 1999).
Kortesis, B., et al., "Vacuum-assisted closure for the treatment of open tibia fractures", 72nd Annual Meeting of the American Society of Plastic Surgeons, San Diego, CA, pp. 172-173; 1 sheet of abstract (Oct. 25-29, 2003).

(56) References Cited

OTHER PUBLICATIONS

Kremers, L., et al., "Effect of topical sub-atmospheric pressure treatment on angiotensin I and II levels post burn", 35th Annual Meeting, Abstract printed in J. Burn Care Rehabilitation, p. S44, Abstract No. 3 American Burn Association, Miami, Florida (Apr. 1-4 2003).

Kremers, L., et al., "Serum interleukin levels post burn with and without application of sub-atmospheric pressure", 35th Annual Meeting, Abstract printed in Burn Care Rehabilitation, p. S43, Abstract No. 2, American Burn Association, Miami, Florida, (Apr. 1-4 2003).

Molnar, J.A., et al., "Improved skin graft adherence and vascularization of integra(R) using subatmospheric pressure—a laboratory study", Abstract printed in Burn Care & Rehabilitation, p. S111, Abstract No. 141; American Burn Meeting, 34th Annual Meeting, Chicago, IL, (Apr. 24-27 2002).

Morykwas, M.J., et al., "Negative pressure treatment of burned extremities", 65th Annual Scientific Meeting, American Society of Plastic and Reconstructive Surgeons, Dallas, TX, pp. 86-87; 1 sheet of abstract (Nov. 9-13, 1996).

Morykwas, M.J., et al., "The effect of V.A.C.(TM) therapy on the length of stay, total charges and average daily charge for patients assigned to DRG 263: analysis of 13 consecutive quarters", presented in part at the 28th Annual Conference of the Wound, Ostomy, and Continence Nurses Society, Seattle, WA, (15 sheets) (Jun. 15-19, 1996).

Park, C.A., et al., "Outpatient use of Integra® and subatmospheric pressure in the management of wound and burn reconstruction", J. Burn Care Rehabil., 26(2 suppl.):S113, Chicago, IL, (May 10-13, 2005).

Schneider, A.M., et al., "Muscle flap survival after complete venous occlusion by application of a negative pressure device", 66th Annual Meeting of the American Society of Plastic and Reconstructive Surgeons, San Francisco, CA, pp. 300-302; 2 sheets of abstract (Sep. 21-24 1997).

Schneider, A.M., et al., "Treatment of brown recluse spider bite wounds by external application of sub-atmospheric pressure", 68th Annual Meeting of the American Society of Plastic and Reconstructive Surgeons, New Orleans, LA, p. 35; 1 sheet of abstract (Oct. 24-27, 1999).

Webb, L.X., "Use of negative pressure devices in highly contaminated, high energy wounds", Extremity War Injuries: State of the Art and Future Directions, AAOS/OTA Extremity War Injures Symposium, Jan. 24-27, 2006, [Abstract].

Morykwas, M.J., "Basic Research and Animal Studies," Presentation at the European Topical Negative Pressure Meeting in Salsbury, England, (Jun. 2005).

Fleischmann, W., et al., "Vacuum assisted closure of wounds following dermatofasciotomy of the leg", Unfallchirurg., (English abstract on p. 284, and 1 sheet printout from PubMed); 99(4):283-7, (Apr. 1996).

Ford, C.N., et al., "Interim analysis of a prospective, randomized trial of vacuum-assisted closure versus the healthpoint system in the management of pressure ulcers", Ann. Plast. Surg., (11 sheets); 49(1):55-61 (Jul. 2002).

Gouttefangeas, C., et al., "Functional T lymphocytes infiltrate implanted polyvinyl alcohol foams during surgical wound closure therapy," Clin. Exp. Immunol., 124(3):398-405 (Jun. 2001).

Greer, S.E., et al., "Subatmospheric pressure dressing for saphenous vein donor-site complications," Ann. Thorac. Surg., (6 sheets); 71(3):1038-40 (Mar. 2001).

Hawkins-Bradley, B., et al., "Treatment of a nonhealing wound with hypergranulation tissue and rolled edges", J. Wound Ostomy Continence Nurs., 29(6):320-324 (Nov. 2002).

Harlan, J.W., "Treatment of open sternal wounds with the vacuum-assisted closure system: a safe, reliable method", Plast. Reconstruct. Surg., 109(2):710-12 (Feb. 2002).

Hartnett, S., "Heparin-induced thrombocytopenia as the cause of gluteus muscle necrosis: a case study describing the benefits of multidisiplinary physical and psychosocial interventions", Ostomy Wound Manage., 47(5):18-26 (May 2001).

Hersh, R.E., et al., "A technique for the treatment of sternal infections using the vacuum assisted closure™ device", Heart Surg. Forum, 4(3):211-15 (2001).

Ingber, D.E., "Mechanical signaling and the cellular response to extracellular matrix in angiogenesis and cardiovascular physiology", Circ. Res., 91:877-887 (Nov. 15, 2002).

Kalailieff, D., "Vacuum-assisted closure: wound care technology for the new millennium", Perspectives, 22(3):28-9 (Fall 1998).

Kercher, K.W., et al., "Successful salvage of infected PTFE mesh after ventral hernia repair", Ostomy Wound Manage., 48(10):40-5 (Oct. 2002).

Kiernan, M., "The process of granulation and its role in wound healing", Community Nurse, 5(5):47-48 (Jun. 1999).

Kloth, L.C., "5 questions-and answers-about negative pressure wound therapy", Adv. Skin Wound Care, 15(5):226, 228-9 (Sep.-Oct. 2002).

Kusel, C., "Use of V.A.C. (vacuum-assisted closure) therapy in general surgery: problem wounds deprived of air", Pflege Z., (and 1 sheet printout from PubMed); 55(6):408-412 (Jun. 2002).

Labler, L., et al., "Vacuum sealing of problem wounds", Swiss Surg., (English abstract on first page, 1 sheet printout from PubMed); 8(6):266-7 (2002).

Marston, W.A., et al., "The efficacy and safety of Dermagraft in improving the healing of chronic diabetic foot ulcers: results of a prospective randomized trial", Diabetes Care, 26(6) 10 pp., (Exhibit 271) (Jun. 1, 2003).

Mendez-Eastman, S., "New treatment for an old problem: negative-pressure wound therapy", Nurs., 32(5):58-64. (12 sheets) (May 2002).

Muller, G., "Vacuum dressing in septic wound treatment", Langenbecks Arch. Chir. Suppl. Kongressbd., (English abstract on p. 537, and 1 sheet printout from PubMed); 114:537-41 (1997).

McGuinness, J.G., et al., "Vacuum-assisted closure of a complex pilonidal sinus", Dis. Colon Rectum, 46(2):274-6 (Feb. 2003).

Moran, S.G., et al., "Vacuum-assisted complex wound closure with elastic vessel loop augmentation: a novel technique", J. Wound Care, 12(6):212-3 (Jun. 2003).

Schipper, J., et al., "The preconditioning and prelamination of pedicled and free microvascular anastomised flaps with the technique of vacuum assisted closure", Laryngorhinootologie, (English abstract on first page, and 2 sheets printout from PubMed); 82(6):421-7, (Jun. 2003).

Shi, B., et al., "Effects of vacuum-assisted closure (VAC) on the expressions of MMP- 1, 2, 13 in human granulation wound", Zhonghua Zheng Xing Wai Ke Za Zhi, (English abstract on first page and 1 sheet printout from PubMed); 19 (4):279-81 (Jul. 2003).

Silver, F.H., et al., "Mechanobiology of force transduction in dermal tissue", Skin Res. Technol., 9(1):3-23 (Feb. 2003).

Silver, F.H., et al., "Mechanosensing and mechanochemical transduction: how is mechanical energy sensed and converted into chemical energy in an extracellular matrix?" Crit. Rev. Biomed. Eng., 31(4):255-331 (2003).

Skillman, J., et al., "Vacuum assisted closure (VAC) dressing for skin graft application following exenteration of the orbit", Orbit, 22(1):63-5 (Mar. 2003).

Song, D.H., et al., "Vacuum assisted closure for the treatment of sternal wounds: the bridge between debridement and definitive closure", Plast. Recontr. Surg., 111(1):92-7 (Jan. 2003).

Wanner, M.B., et al., "Vacuum-assisted wound closure for cheaper and more comfortable healing of pressure sores: a prospective study", Scand. J. Plast. Reconstruct. Surg. Hand Surg., 37(1):28-33 (2003).

Weaver, B. "The nursing needs of a patient with a complicated abdominal wound", Prof. Nurse, 18(5):269-73 (Jan. 2003).

Wongworawat, M.D., et al., "Negative pressure dressings as an alternative technique for the treatment of infected wounds", Clin. Orthop. Relat. Res., (414):45-8 (Sep. 2003).

Baker, E.A., et al., "Growth factor profiles in intraperitoneal drainage fluid following colorectal surgery: relationship to wound healing and surgery", Wound Rep. Reg., 11(4):261-267, (Jul.-Aug. 2003).

Alberty, A., et al., "Effects of distraction and compression on proliferation of growth plate chondrocytes. A study in rabbits.", Acta Orthop. Scand., (1 sheet printout from PubMed); 64(4):449-455 (Aug. 1993).

(56) References Cited

OTHER PUBLICATIONS

Juchli, L., "Krankenpflege [Nursing] Practice and Theory of Promoting Health and Patient Care," Georg Thieme Verlag Stuttgart, as labeled as "Anlage 6.1" 1991 (allegedly dated Feb. 1991), and email dated May 30, 2007 labeled as "Anlage 6.2," both in German with English translations.
Fleischmann, W., et al., "Combination osteosynthesis in the treatment of pylon fractures with soft tissue damage," labeled "Anlage NK10," pp. 178-181 and showing "6. German-Austrian-Swiss Trauma Conference in Vienna May 21-25, 1991," published in "Der Unfallchirurg" [The Traumatologist] in 1993, in German with English translation.
"Coldex," labeled as "Anlage NK12" in German with English translation.
Turner, T.D., et al., eds., Excerpts from "Advances in wound management," including "Recent advances in wound management products" by T.D. Turner and "The role of foam dressings in wound management" by S. Thomas, Proceedings of a symposium held at the Welsh School of Pharmacy, University of Wales Institute of Science and Technology, Cardiff, Mar. 20-21, 1985, labeled as "Anlage NK13," 1986.
Fleischmann, W., et al., "Combination osteosynthesis in treating pilon fractures involving soft tissue injuries," in "Translation of an excerpt from the brochure regarding the Sixth German-Austrian-Swiss Accident Congress" allegedly dated 1991, in German with English translation.
ISO 10079-1, "International Standard," "Medical suction equipment—Part 1: electrically powered suction equipment—Safety requirements," dated May 15, 1991.
Spahn, J.G., "Soft tissue challenges in the head and neck region,"Clinical Seminar Handout, EHOB, (46 pages).
Mendez-Eastman, S., "Guidelines for using negative pressure wound therapy", Adv. Skin Wound Care, 14(6):314-323. (16 pp.) (Nov.-Dec. 2001).
Addition to the "Users Manual Concerning Overflow Protection—Concerns all Egnell Pumps", dated Feb. 3, 1983, 1 page Swedish, [1 page English].
Aeros, "Moblvac," "Introducing the 'off the wall' vacuum system," Aeros Instruments, Life Support Nursing, 3(1):34-37, Barlin Publishing Ltd. (Jan.-Feb. 1980).
Article in Russian, pp. 84-85.
Austad, E.D., et al., "Tissue expansion: dividend or loan?"Plast. Reconstr. Surg.,78(1):63-67 (Jul. 1986).
BlueSky Medical, 2 sheets of advertisement, "Introducing the Chariker-Jeter wound drainage kit" and "Introducing the Kremlin® wound drainage kit".
Egnell Minor, Instruction Book, First Addition [Edition], allegedly dated Feb. 1987, 21 pages Swedish, 3 pages English.
Feierabend, T.C., et al., "Injuries causing major loss of scalp", Plast. Reconstr. Surg., [Abstract only—1 pp. printout from PubMed], 76(2):189-194 (Aug. 1985).
Geronemus, R.G., et al., "The effect of two new dressings on epidermal wound healing", J. Dermatol. Surg. Oncol., 8(10):850-852 (Oct. 1982).
Miller, S.H., et al., "An inexpensive wound suction device", Surg. Gyencol. Obstet., 141(5):768 (Nov. 1975).
Miller, S.J., "Surgical wound drainage system using silicone tubing", J. Am. Podiatry Assn., 71(6): pp. 287-296, (Jun. 1981).
Nelson, R.P., et al., "Use of negative pressure suction in urology", Urology, 4(5):574-576, (Nov. 1974).
Svedman, "Irrigation Treatment of Leg Ulcers", The Lancet, Sep. 3, 1983, pp. 532-534.
Stewart, A., et al., "Cleaning v. healing," Community Outlook, pp. 22, 24 & 26 (Aug. 14, 1985).
Trammell, T.R., et al., "Closed-wound drainage systems: the Solcotrans Plus versus the Stryker-CBC ConstaVAC", Orthopaedic Review, 20(6):536-542 (Jun. 1991).
Woodley, D.T., et al., "A double-blind comparison of adhesive bandages with the use of uniform suction blister wounds", Arch. Dermatol., 128(10):1354, 1357 (Oct. 1992).
Zelko, J.R., et al., "Primary closure of the contaminated wound; closed suction wound catheter", Am. J. Surgery, 142:704-706, (Dec. 1981).
Morykwas, M.J., et al., "Use of Negative Pressure to Increase the Rate of Granulation Tissue Formation in Chronic Open Wounds", The FASEB Journal, (799-800), Feb. 19, 1993.
Orringer, J.S., et al., "Management of Wounds in Patients with Complex Enterocutaneous Fistulas", Surgery, Gynecology & Obstetrics, Jul. 1987, vol. 165.
Swearingen, P.L., "The Addison-Wesley Photo-Atlas of Nursing Procedures", 9 pages, © 1984.
Mulder, G.D, et al., Clinicians' Pocket Guide to Chronic Wound Repair, Wound Healing Publications Second Edition, 1992, pp. 1-107.
Peacock, E.E., Jr., Wound Repair:, Repair of Skin Wounds, 1984, pp. 172-175.
Davies , J.W.L, "Synthetic materials for covering burn wounds: Progress towards perfection. Part I. Short term dressing materials", Burns, Nov. 1983;10(2), 94-103.
Lamke, L.O., et al., "The evaporative water loss from burns and the water-vapour permeability of grafts and artificial membranes used in the treatment of burns", Burns, 3, 159-165, 1977.
Barnett, A., et al., "Comparison of Synthetic Adhesive Moisture Vapor Permeable and Fine Mesh Gauze Dressings for Split-Thickness Skin Graft Donor Sites", The American Journal of Surgery, vol. 145, Mar. 1983, pp. 379-381.
Alper, J., et. al., "Moist wound healing under a vapor permeable membrane", Journal of the American Academy of Dermatology, vol. 8, No. 3, Mar. 1983, pp. 347-353.
James, J.H., et. al., "The use of Opsite, A Vapour Permeable Dressing, on Skin Donor Sites", British Journal of Plastic Surgery (1975), 28, 107-110.
Nahas, L.F., et al., "Use of Semipermeable Polyurethane Membrane for Skin Graft Dressings", Plastic and Reconstructive Surgery, Jun. 1981, pp. 791-792.
Edlich, R.F., et al., "Surgical Devices in Wound Healing Management", Wound Healing Biochemical & Clinical Aspects, W.B. Saunders Company, © 1992, pp. 581-599.
Orr, RK, et al., "Early Discharge After Mastectomy. A Safe Way of Diminishing Hospital Cost", Am Surg. Mar. 1987; 53(3) Abstract.
Otolaryngology, Head and Neck Surgery, The C.V. Mosby Company, © 1986, pp. 1716, 1724 and 2521.
Otolaryngology, vol. III, Head and Neck, W.B. Saunders Company, © 1980, pp. 2963.
Lore, Jr., J.M., "An Atlas of Head and Neck Surgery", Second Edition, vol. II, W.B. Saunders Company, Ó 1973.
Johnson, Frank E., "An Improved Technique for Skin Graft Placement Using a Suction Drain", pp. 585-586 (Dec. 1984).
Dewan, P.A., et al., "An Alternative Approach to Skin Graft Donor Site Dressing", Aust. N.Z. J. Surg. 1986, 56, 509-510.
3M™, Tegaderm Family of Transparent Dressings for Chronic Wounds, pp. 1-8 (2002).
Alper, Joseph C., et al., "The In Vitro Response of Fibroblasts to the Fluid that Accumulates Under a Vapor-Permeable Membrane". Journal of Investigative Dermatology, 84:513-515, 1985.
Alper, Joseph C., et al., "Use of the Vapor Permeable Membrane for Cutaneous Ulcers: Details of application and side effects", Journal of the American Academy of Dermatology, vol. 11, No. 5, Part I, Nov. 1984, pp. 858-866.
Angermeier, Marla C., et al., "Vapor-Permeable Membrane Therapy for Ulcers of Osteomyelitis", J. Dermatol. Surg. Oncol,, 10:5, May 1984, pp. 384-388.
Bourke, et al., "Comparison Between Suction and Corrugated Drainage After Simple Mastectomy: A Report on Controlled Trial", Br. J. Surg., vol. 63, 1976, pp. 67-69.
ConstaVac™ Closed Wound Drainage System, Stryker Instruments, 2 pages.
Eaglstein, William H., "Experiences with Biosynthetic Dressings", Journal of the American Academy of Dermatology, vol. 12, No. 2, Part 2, Feb. 1985, pp. 434-440.
Falanga, Vincent, et al., "A Therapeutic Approach to Venous Ulcers", Journal of the American Academy of Dermatology, vol. 14, No. 5, Part 1, May 1986, pp. 777-784.

(56) References Cited

OTHER PUBLICATIONS

Friedman, S., et al., "Treatment of Dermabrasion Wounds with a Hydrocolloid Occlusive Dressing", Arch Dermatol, vol. 121, Dec. 1985, pp. 1486-1487.
Friedman, Stephen J., et al., "Management of Leg Ulcers with Hydrocolloid Occlusive Dressing", Arch. Dermatol., vol. 120, Oct. 1984, pp. 1329-1336.
Holland, K.T., et al., "A Comparison of the In Vivo Antibacterial Effects of OpSite, Tegaderm and Ensure dressings", Journal of Hospital Infection, 1985, 6, pp. 299-303.
Jeter, Katherine F., et al., "Wound Dressings of the Nineties: Indications and Contraindications", Clinics in Podiatric Medicine and Surgery, vol. 8, No. 4, Oct. 1991, pp. 799-816.
Katz, Stuart, et al., "Semipermeable Occlusive Dressings", Arch Dermatol., vol. 122, Jan. 1986, pp. 58-62.
Lewis, R.T., "Knitted Polypropylene (Marlex) Mesh in the Repair of Incisional Hernias", The Canadian Journal of Surgery, vol. 27, No. 2, Mar. 1984, pp. 155-157.
Lower Extremity Ulcers, Chapter 9, pp. 47-57.
Microtek Medica, Inc. "The Microtek Complete Closed Wound Drainage System", 6 pages.
Rovee, David T., et al., "Effect of Local Wound Environment on Epidermal Healing", Dept. of Skin Biology, Johnson & Johnson Research, New Brunswick, NJ, pp. 159-181 (1972).
Satas, Donatas, "Handbook of Pressure-Sensitive Adhesive Technology", Silicone Release Coatings, Van Nostand Reinhold Company, 1982, pp. 384-403.
Turner, T.D., "A Look at Wound Dressings", Health and Social Service Journal, May 4, 1979, pp. 529-531.
Turner, T.D., "Recent Advances in Wound Management Products", pp. 3-6.
Turner, T.D., "Semipermeable Films as Wound Dressings", Welsh School of Pharmacy, University of Wales, Great Britain (Jul. 31, 1984).
Turner, T.D., "The Development of Wound Management Products", Chronic Wound Care, pp. 31-46.
Turner, T.D., et al., "Wound Management Product Selection", Journal of Sterile Services Management, Apr. 1985, pp. 3-6.
Varghese, Mathew C., et al., "Local Environment of Chronic Wounds Under Synthetic Dressings", Arch. Dermatol, vol. 122, Jan. 1986, pp. 52-57.
Viljanto, J., "Cellstic: A Device for Wound Healing Studies in Man. Description of the Method", Journal of Surgical Research, 20, 1976, pp. 115-119.
Wagner, S.A., et al., "An individualized Plastic Intraoral Device for the Collection of Human Parotid Saliva", International Journal of Clinical Pharmacology, Therapy and Toxilogy, Vo. 22, No. 5, 1984, pp. 236-239.
Wilson, John L., et al., "Loss of Blood Volume in Spinal Surgery with Use of Closed Wound Suction: An Experimental Study", Southern Medical Journal, Jul. 1968, pp. 761-763, read before the Section on Orthopaedic and Traumatic Surgery, Southern Medical Association, 61st Annual Meeting, Miami Beach, FL, (Nov. 13-16, 1967).
Winter, G.D., "Healing of Skin Wounds and the Influence of Dressings on the Repair Process", pp. 46-60 of "Surgical dressings and wound healing: proceedings of a symposium held on Jul. 7-8, 1970 at the University of Bradford," Crosby Lockwood for Bradford University Press, (1971).
Avery, C., et al., "Negative pressure wound dressing of the radial forearm donor site", International Journal of Oral Maxillofacial Surgery, 2000; 29, pp. 198-200.
Armstrong, David G., et al., "Outcomes of Subatmospheric Pressure Dressing Therapy on Wounds of the Diabetic Foot", Ostomy/Wound Management 2002; 48(4): 64-68.
Brown, Karen M., et al., "Vacuum-Assisted Closure in the Treatment of a 9-Year-Old Child with Severe and Multiple Dog Bite Injuries of the Thorax", Society of Thoracic Surgeons, 2001; 72:1409-1410.
Catarino, Pedro A., et al., "High-Pressure Suction Drainage via a Polyurethane Foam in the Management of Poststernotomy Mediastinitis", Ann Thorac Surg 2000; 70:1891-5.

Mendez-Eastman, Susan, RN, CPSN, CWCN, Clinical Management Extra, Guidelines for Using Negative Pressure Wound Therapy, Advances in Skin & Wound Care, Nov./Dec. 2001, vol. 14, No. 6, p. 314-323.
Cooper, Susan Mary, "Topical negative pressure in the treatment of pressure ulcers", Letters posted in the Journal of the American Acad of Dermatology, August, Part 1, 1999, p. 280.
Davydov, I.A., et al., "Concept of clinico-biological control of the wound", Vestnik khirurgii imeni I.I. Grekova, v. 146, issue 2, 1991, 132-6 (with English translation).
de la Torre, Jorge I., MD, et al., "Healing a Wound with an Exposed Herrington Road: A Case Study", Ostomy Wound Management, pp. 18-19, May 2002, vol. 48, Issue 5.
de Lange, M.Y., et al., "Vacuum-assisted closure: indications and clinical experience", Eur J Plast Surg (2000) 23:178-182.
Deva, Anand, K., et al, "Topical negative pressure in wound management", MJA, Vo. 173, pp. 128-131, Aug. 7, 2000.
Elwood, Eric T., et al., "Negative-Pressure Dressings in the Treatment of Hidradenitis Suppurativa", Ann Plast Surgery Jan. 2001; 46:49-51.
Evans, D. and Land, L., "Topical negative pressure for treating chronic wounds: a systematic review", British Journal of Plastic Surgery (2001), 54, 238-242.
Fabian, Thaddeus S., MD, "The Evaluation of Subatmospheric Pressure and Hyperbaric Oxygen in Ischemic Full-Thickness Wound Healing", The American Surgeon, Dec. 2000, vol. 66, 1136-1143.
Fenn, C.H. and Butler, P.E.M., "Abdominoplasty wound-healing complications: assisted closure using foam suction dressing", British Journal of Plastic Surgery (2001), 54, 348-351.
Giovannini, Uberto M., MD, "Negative Pressure for the Management of an Exposed Vascular Dacron Polyester Patch", Annals of Plastic Surgery, 47(5): 577-578, 2001.
Gustafsson, Ronny, MD, "Vacuum-assisted closure therapy guided by C-reactive protein level in patients with deep sternal wound infection", The Journal of Thoracic and Cardiovascular Surgery, vol. 123, No. 5, pp. 895-900, May 2002.
Gwan-Nulla, Daniel N., MD and Casal, Rolando S., MD, "Toxic Shock Syndrome Associated with the Use of the Vacuum-Assisted Closure Device", Ann Plastic Surgery 2001;47:552-554.
Hersh, Robert E., MD, et al., "The Vacuum-Assisted Closure Device as a Bridge to Sternal Wound Closure", Ann Plast Surg. 2001; 46: 250-254.
Heugel, Judson R., et al., "Treatment of the Exposed Achilles Tendon Using Negative Pressure Wound Therapy: A Case Report", Journal of Burn Care and Rehabilitation, May/Jun. 2002, vol. 23, No. 3, pp. 167-171.
Joseph, Emmanuella, MD, et al., "A Prospective Randomized Trial of Vacuum-Assisted Closure Versus Standard Therapy of Chronic Nonhealing Wounds", Wounds 2000: 12(3): 60-67.
Josty, I.C., et al., "Vacuum-assisted closure: an alternative strategy in the management of degloving injuries of the foot", British Journal of Plastic Surgery (2001), 54, pp. 363-365.
Kostiuchenok, B.M., et al., "Vacuum Treatment in the Surgical Management of Suppurative Wounds", Izdatelstvo Meditsina, St. Petersburg, Sep. 1986; 137(9): 18-21 (with English Translation).
Kovacs, Laszlo H., MD, "Necrotizing Fasciitis", Annals of Plastic Surgery, vol. 47, No. 6, Dec. 2001, pp. 680-682.
Kranser, Diane L., "Managing Wound Pain in Patients with Vacuum-Assisted Closure Devices", Ostomy Wound Management 2002; 48(5): 38-43.
Mendez-Eastman, Susan, RN, CPSN, CWCN, "wound therapy", Nursing2002, vol. 32, No. 5, May, pp. 59-63 and 1 sheet of quiz.
Mooney, James F., III., "Treatment of Soft Tissue Defects in Pediatric Patients Using the V.A.C. TM System", Clinical Orthopedics and Related Research, No. 376, pp. 26-31, Jul. 2000.
Scheufler, O., et al., "Problem-adapted application of vacuum occlusion dressings: case report and clinical experience", Eur J. Plast Surg (2000) 23: 386-390.
Sposato, G., et al., "Ambulant vacuum-assisted closure of skin-graft dressing in the lower limbs using a portable mini-Vac device", British Journal of Plastic Surgery (2001), 54, 235-237.

(56) References Cited

OTHER PUBLICATIONS

Tang, Augustine T.M., et al., "Novel application of vacuum assisted closure technique to the treatment of sternotomy wound infection", European Journal of Cardio-Thoracic Surgery 17 (2000) 482-484.
Wu, S.H., et al., "Vacuum therapy as an intermediate phase in wound closure: a clinical experience", Eur J Surg (2000) 23:174-177.
Zhivotaev VM. Vacuum therapy of postoperative infected wounds of the urinary bladder, Klinicheskaia Khiurgiia. 1970;5:36-39. (in Russian) (and 1 sheet printout from PubMed).
The Kremlin Papers . . . perspectives in wound care, "A collection of published studies complementing the research and innovation of wound care", Russian Medical Journal "Vestnik Khirurgii", 5 Russian Articles from 1986-1991, translated by BlueSky Medical Group Inc. © 2004.
Davydov, Y.A., et al., "The bacteriological and cytological assessment of vacuum therapy of purulent wounds", Vestnik Khirurgii imeni I.I. Grekova, (1 sheet of title page and pp. 48-52, 5 sheets of Russian text and English abstract on p. 52); 141(10):48-52, (Oct. 1988).
Davydov, Y.A., et al., "Bacteriological and cytological assessment of vacuum therapy of purulent wounds," (7 sheets of translation, pp. 48-52 of Russian text and English abstract on p. 52); 141(10):48-52 (Oct. 1988).
Davydov, Y.A., et al., "Vacuum therapy in the treatment of purulent lactation mastitis", Vestnik Khirurgii Imeni I.I. Grekova, (1 Sheet of Title page and pp. 66-70, 6 sheets of Russian text and English abstract on p. 70); 137 (11):66-70, (Nov. 1986).
Davydov, Y.A., et al., "Vacuum therapy in the treatment of purulent lactation mastitis", (8 sheets of English translation, pp. 66-70 of Russian text, and English abstract on p. 70); 137(11):66-70, (Nov. 1986).
Davydov, Y.A., et al., "Vacuum therapy in the treatment of acute purulent diseases of soft tissues and purulent wounds", (4 sheets of Translation, 4 sheets of Russian text and English abstract on p. 46); 141(9):43-46 (Sep. 1988).
Davydov, Y.A., et al., "Vacuum therapy in treatment of acute purulent diseases of soft tissues and purulent wounds," Vestnik Khirurgii (Surgeon's Herald), No. 9 Medicine Publishers, (5 sheets of translation), (1986).
Argenta, L.C., et al., "Vacuum-assisted closure: state of clinic art", Plast. Reconstr. Surg., 117 (7 Suppl.): 127S-142S (Jun. 2006).
Chung, C.J., et al., "Case review: management of life-threatening sepsis and wound healing in a Klippel-Trenaunay patient using serial surgical debridements and vacuum-assisted closure", Eur. J. Plast. Surg., 26:214-216 (2003).
Dedmond, B.T., et al., "Subatmospheric pressure dressings in the temporary treatment of soft tissue injuries associated with type III open tibial shaft fractures in children", J. Pediatr. Orthop., 26(6):728-732, (Nov.-Dec. 2006).
Dedmond, B.T., et al., "The use of negative-pressure wound therapy (NPWT) in the temporary treatment of soft tissue injuries associated with high-energy open tibial shaft fractures", J. Orthop. Trauma, 21(1):11-17, (Jan. 2007).
Gemeinhardt, K.D., et al., "Vacuum-assisted closure for management of a traumatic neck wound in a horse", Equine Veterinary Education, 17(1):27-32, (2005).
Laverty, D., et al., "Negative pressure wound therapy in the management of orthopedic wounds", Ostomy Wound Manage., 50(11A suppl):18S-9S (Nov. 2004).
Molnar, J.A., "Applications of negative pressure wound therapy to thermal injury", Ostomy Wound Manage., 50(4A suppl):17-9 (Apr. 2004).
Molnar, J.A., "The science behind negative pressure wound therapy", Ostomy Wound Manage., 50 (4A suppl):2-5 (Apr. 2004).
Molnar, J.A., et al., "Management of an acute thermal injury with subatmospheric pressure", J. Burns Wounds, 4:83-92, 4:e5 (published online Mar. 24, 2005).
Morykwas, M.J., et al., "Effects of varying levels of subatmospheric pressure on the rate of granulation tissue formation in experimental wounds in swine", Ann. Plast. Surg., 47(5):547-551 (Nov. 2001).
Plikaitis, C.M., et al., "Subatmospheric pressure wound therapy and the vacuum-assisted closure device: basic science and current clinical successes", Expert Rev. Med. Devices, 3(2):175-184, (Mar. 2006).
Schlatterer, D., et al., "Orthopedic indications for negative pressure wound therapy", Ostomy Wound Manage., 51 (2A suppl):27S-8S (Feb. 2005).
Schneider, A.M., et al., "Re: use of specialized bone screws for intermaxillary fixation: reply", Ann. Plast. Surg., 47 (1): 93, (Jul. 2001).
Webb, L.X., et al., "The contaminated high-energy open-fracture: a protocol to prevent and treat inflammatory mediator storm-induced soft-tissue compartment syndrome (IMSICS)", J. Am. Acad. Orthop. Surg., 14(10):SA82-S86 (Oct. 2006).
Yang, C.C., et al., "Vacuum-assisted closure for fasciotomy wounds following compartment syndrome of the leg", J. Surg. Orthop. Adv., 15(1):19-23 (Spring 2006).
Argenta, P.A., et al., "Vacuum-assisted closure in the treatment of complex gynecologic wound failures," Obstet. Gynecol., 99(3):497-501, (9 sheets) (Mar. 2002).
Azad, S., et al., "Topical negative pressure may help chronic wound healing," B.M.J., 324:1100 (1 sheet) (May 4, 2002).
Ballard, K., et al., "Developments in wound care for difficult to manage wounds," Br. J. Nurs., 9(7):405-8,410,412 (Apr. 13-26, 2000).
Ballard, K., et al., "Vacuum-assisted closure," Nurs. Times, 97(35):51-2 (5 sheets) Aug. 30-Sep. 5, 2001.
Ballard, K., et al., "Use of vacuum-assisted closure therapy following foot amputation," Br. J. Nurs., 10(15 Supplement):S6, 8, 11-12 (Aug. 2001).
Banwell, P.E., "Topical negative pressure therapy in wound care," J. Wound Care, 8(2):79-84 (Feb. 1999).
Bartels, C.G., et al., "The vacuum sealing technique. A new approach to cover soft tissue defects, used after the resection of a leiomyosarcoma", (English abstract on 2nd page and 1 page printout from PubMed); Hautarzt, 52 (7):653-7 (Jul. 2001).
Bauer, P., et al., "Possibilities of preliminary treatment of infected soft tissue defects by vacuum sealing and PVA foam", (English abstract on first page and 1 sheet PubMed abstract), Handchir. Mikrochir. Plast. Chir., 30(1):20-3 (Jan. 1998).
Baynham, S.A., et al., "Treating stage IV pressure ulcers with negative pressure therapy: a case report", Ostomy Wound Manage., 45(4):28-32, 34-35 (Apr. 1999).
Birchall, L., et al., "Developing a trust-wide centralised approach to the use of TNP", J. Wound Care, 11(8):311-4 (Sep. 2002).
Brody, G.S., "Biological creep", Plast. Reconstr. Surg., 92(6):1202-1203 (Nov. 1993).
Campton-Johnston, S., et al., "Infected wound management: advanced technologies, moisture-retentive dressings, and die-hard methods", Crit. Care Nurs. Q, 24(2):64-77 (Aug. 2001).
Chen, K.D., et al., "Mechanotransduction in response to shear stress", J. Biol. Chem., 274(26):18393-18400, (Jun. 25, 1999).
Clare, M.P., et al., "Experience with the vacuum assisted closure negative pressure technique in the treatment of non-healing diabetic and dysvascular wounds", Foot Ankle Int., 23(10):896-901 (Oct. 2002).
Claxton, M.J., et al., "Healing the diabetic wound and keeping it healed: modalities for the early 21st century", Curr. Diab. Rep., 2(6):510-8 (Dec. 2002).
Coggrave, M., et al., "Topical negative pressure for pressure ulcer management", Br. J. Nurs., 11(6 Suppl):S29-31, S33-34, S36 (Mar. 2002).
Collier, M., "Know how: Vacuum assisted closure (VAC)", Nurs. Times, 93(5):32-3 (Jan. 29-Feb. 4, 1997).
Cooper, S.M., et al., "Topical negative pressure", Int. J. Dermatol., 39(12):896-8 (Dec. 2000).
Cozart, R.F., et al., "The use of controlled subatmospheric pressure to promote wound healing in preparation for split-thickness skin grafting in a fourth degree burn", Tenn. Med., 92(10):382-4 (Oct. 1999).
Cro, C., et al., "Vacuum assisted closure system in the management of enterocutaneous fistulae," Postgrad. Med. J., 78(925):364-5 (Nov. 2002).

(56) References Cited

OTHER PUBLICATIONS

De Filippo, R.E., et al., "Stretch and growth: the molecular and physiologic influences of tissue expansion", Plast. Reconstr. Surg., 109(7):2450-2462 (Jun. 2002).
Deva, A.K., et al., "Vacuum-assisted closure of a sacral pressure sore", J. Wound Care, 6(7):311-312, (Jul. 1997).
Dunford, C., "Hypergranulation tissue", J. Wound Care, 8(10):506-507 (Nov. 1999).
Dunford, C.E., "Treatment of a wound infection in a patient with mantle cell lymphoma", Br. J. Nurs., 10(16):1058, 1060, 1062, 1064-5 (Sep. 13-26, 2001).
Espensen, E.H., et al., "Use of subatmospheric (VAC) therapy to improve bioengineered tissue grafting in diabetic foot wounds", J. Am. Podiatr. Med. Assoc., 92(7):395-7 (Jul.-Aug. 2002).
Fleck, T.M., et al., "The vacuum-assisted closure system for the treatment of deep sternal wound infections after cardiac surgery", Ann. Thorac. Surg., 74(5):1596-600 (Nov. 2002).
Bagautdinov, N.A., "Alternative method of external vacuum aspiration in the treatment of purulent soft tissue disease," Curr. Problems Contemporary Clin. Surg.: Interscholastic Collection, pp. 94-96, (6 sheets of English translation and certification dated May 30, 2008; four sheets of English translation, 6 sheets in Russian, and certification dated May 9, 2008; 1 sheet of English translation of alleged library index card, 1 sheet in Russian, and certification dated May 7, 2008); I.N. Ulianov Chuvash State University, Cheboksary, (1986).
Zivadinovic, G., et al., "Vacuum therapy in the treatment of peripheral blood vessels," Conference Papers of the 5th Timok Medical Days, Majdanpek, No. 3-4, pp. 161-164, (5 sheets English translation; 5 sheets in Serbian, certification dated May 9, 2008) (1986).
Johnson, F.E., "An improved technique for skin graft placement using a suction drain", Surg. Gynecol. Obstet., 159 (6):584-585 (Dec. 1984).
Safronov, A.A., Dissertation Abstract, "Vacuum therapy of trophic ulcers of the lower leg with simultaneous autoplasty of the skin," (Central Scientific Research Institute of Traumotology and Orthopedics, Moscow, U.S.S.R.) (23 sheets English translation; 23 sheets in Russian; certification dated May 8, 2008; alleged index card(English translation; 1 sheet Russian; certification dated May 14, 2008), (1967).
Tribble, D.E., "An improved sump drain-irrigation device of simple construction," Arch. Surg., 105:511-513, (Sep. 1972).
Tennant, C.E., "The use of hyperemia in the postoperative treatment of lesions of the extremities and thorax," Jour. A.M.A., 64(19):1548-1549, (May 8, 1915).
Orgill, D.P., et al., "Microdeformational wound therapy—a new era in wound healing," Business Briefing: Global Surgery—Future Directions, pp. 22, 24-25 (2005).
"V.A.C.® Therapy Clinical Guidelines: A reference source for clinicians," KCI, The Clinical Advantage® (Jul. 2007).
Bagautdinov, N.A., "Variant of external vacuum aspiration in the treatment of purulent diseases of soft tissues," Current Problems in Modern Clinical Surgery, Interdepartmental Collection, Cheboksary, (4 pages of English translation, 6 sheets in Russian, certification dated May 22, 2008, English translation of index card, 1 sheet Russian, certification dated May 7, 2008) (1986).
Chardak, W.M., et al., "Experimental studies on synthetic substitutes for skin and their use in the treatment of burns," Ann. Surg., 155(1):127-139, (Jan. 1962).
Fujimori, R., et al., "Sponge fixation method for treatment of early scars," Plast. & Reconst. Surg., 42(4):322-326, (Oct. 1968).
Kirk-Othmer, Encyclopedia of Chemical Technology, 2nd completely revised edition, vol. 14, pp. 227, John Wiley & Sons, Inc., (1967).
Meyer, W., et al., excerpts from "Bier's Hyperemic Treatment", W.B. Saunders and Co., (48 sheets) (1908).
Zivadinovic, G., et al., "Vacuum therapy in the treatment of peripheral blood vessels," Timok Medical Journal, Abstract book of the 5th Timok Medical Days, Majdanpek, 6 sheets of English translation, (1986).
Safronov, A.A., "Vacuum therapy for trophic ulcers of the tibia with concurrent skin autoplasty," Dissertation abstract, additional abstract, Moscow, 20 sheets of English translation, (1967).
Safronov, A.A., Abstract of Invention No. 240188, "Device for wound or ulcer treatment," (2 sheets English translation and 2 sheets in Russian) (1969).
Svedman, P., et al., "A dressing system providing fluid supply and suction drainage used for continuous or intermittent irrigation", Ann. Plast. Surg., 17(2):125-33 (Aug. 1986).
"Pressure equivalents," McGraw-Hill Encyclopedia of Science & Technology, 6th ed., New York, pp. 249, (1987).
Thomas, S., "Wound management and dressings," cover sheet, preface, sheet labeled "Chapter 5" and pp. 36-39 (1990).
Conquest, A.M., et al., "Hemodynamic effects of the vacuum-assisted closure device on open mediastinal wounds,"J. Surg. Res., 115(2):209-13 (Dec. 2003).
Copson, D., "Topical negative pressure and necrotising fasciitis", Nurs. Stand., 18(6):71-2, 74, 76, 78, 80 (Oct. 22, 2003).
Demaria, R.G., et al., "Topical negative pressure therapy. A very useful new method to treat severe infected vascular approaches in the groin," J. Cardiovascular Surg., 44(6):757-61 (Dec. 2003).
De Vooght, A., et al., "Vacuum-assisted closure for abdominal wound dehiscence with prosthesis exposure in hernia surgery,"Plast. Recontr. Surg., 112(4):1188-9 (Sep. 15, 2003).
Duxbury, M.S., et al., "Use of a vacuum assisted closure device in pilonidal disease,"J. Wound Care, 12(9):355 (Oct. 2003).
Eldad, A., et al., "Vacuum—a novel method for treating chronic wounds", Harefuah, (English abstract on last 2 pp. and 1 sheet printout from PubMed); 142(12):834-6, 878, 877 (Dec. 2003).
Evans, D., et al., "Topical negative pressure for treating chronic wounds", Cochrane Database Syst. Rev., vol. (3), accession No. 00075320-100000000-01309 (2005).
Fuchs, U., et al., "Clinical outcome of patients with deep sternal wound infection managed by vacuum-assisted closure compared to conventional therapy with open packaging: a retrospective analysis", Ann. Thorac. Surg., 79:526-31 (2005).
Gustafsson, R.I., et al., "Deep sternal wound infection: a sternal-sparing technique with vacuum-assisted closure therapy" Ann. Thorac. Surg., 76(6):2048-53 (Dec. 2003).
Herscovici Jr., D., et al., "Vacuum-assisted wound closure (VAC therapy) for the management of patients with high-energy soft tissue injuries", J. Orthrop. Trauma, 17(10):683-8 (Nov.-Dec. 2003).
Huang, J., et al., "Treatment of open fracture by vacuum sealing technique and internal fixation", Zhongguo Xiu Fu Chong Jian Wai Ke Za Zhi, (English abstract on first page and 2 sheets printout from PubMed); 17(6):456-8 (Nov. 2003).
Jones, E.G., et al., "Management of an ileostomy and mucous fistula located in a dehisced wound in a patient with morbid obesity", J. Wound Ostomy Continence Nurs., 30(6):351-356 (Nov. 2003).
Langley-Hawthorne, C., "Economics of negative pressure wound therapy", Ostomy Wound Manage., 50(4A suppl):35, 36, C3 (Apr. 2004).
Neubauer, G., et al., "The cost-effectiveness of topical negative pressure versus other wound-healing therapies", J. Wound Care, 12(10):392-3 (Nov. 2003).
Orgill, D.P., et al., "Functional reconstruction following electrical injury", Ann. N.Y. Acad. Sci., 888:96-104 (Oct. 30, 1999).
Salameh, J.R., et al., "Laparoscopic harvest of omental flaps for reconstruction of complex mediastinal wounds", JSLS, 7(4):317-22 (Oct.-Dec. 2003).
Shoufani, A., et al., "Vacuum assisted closure—a new method for wound control and treatment", Harefuah, (English abstract on last page; 1 sheet printout from PubMed); 142(12):837-40, 877 (Dec. 2003).
Shvartsman, H.S., et al., "Use of vacuum-assisted closure device in the treatment of recurrent Paget's disease of the vulva", Obstet. Gynecol., Supplement, 102(5, part 2):1163-6 (Nov. 2003).
Sibbald, R.G., et al., "A consensus report on the use of vacuum-assisted closure in chronic, difficult-to-heal wounds", Ostomy Wound Manage., 49(11):52-66 (Nov. 2003).
Wagner, S., et al., "Comparison of inflammatory and systemic sources of growth factors in acute and chronic human wounds", Wound Rep. Reg., 11:253-260 (Jul.-Aug. 2003).

(56) References Cited

OTHER PUBLICATIONS

Wild, T., "Consensus of the German and Austrian Societies for wound healing and wound management on vacuum closure and the VAC treatment unit", MMW Fortschr. Med., (English abstract on p. 100; 1 sheet printout from PubMed); 145 Suppl. 3:97-101 (Oct. 9, 2003).

Chen, S.Z., et al., "Effect of vacuum-assisted closure on the expression of proto-oncogenes and its significance during wound healing", Zhonghua Zheng Xing Wai Ke Za Zhi, (English abstract on first page, 2 sheets printout from PubMed); 21:197-200 (May 2005).

Immer, F.F., et al., "Deep sternal wound infection after cardiac surgery: modality of treatment and outcome", Ann. Thorac. Surg., 80(3):957-61 (Sep. 2005; available online Aug. 23, 2005).

Saltzman, C.L., "Salvage of diffuse ankle osteomyelitis by single-stage resection and circumferential frame compression arthrodesis", Iowa Orthop. J., 25:47-52 (2005).

Bogart, L., "A summary of posters presented at the symposium on Advanced Wound Care: 2003 and 2004", Ostomy Wound Manage., 51(4):88-91 (Apr. 2005).

Chen, S.Z., et al., "Effects of vacuum-assisted closure on wound microcirculation: an experimental study", Asian J. Surg., 28(3):211-7 (Jul. 2005).

Paul, J.C., "Vacuum assisted closure therapy: A must in plastic surgery", Plastic Surg. Nurs., 25(2):61-5 (Apr.-Jun. 2005).

Winter, D., "Perspectives on vacuum-assisted closure therapy in pilonidal sinus surgery", Dis. Colon Rectum, 48 (9):1829-30, (Sep. 2005).

Arca, M.J., et al., "Use of vacuum-assisted closure system in the management of complex wounds in the neonate", Pediatr. Surg. Int., 21(7):532-5, 8 sheets, (published online Jun. 17, 2005).

Adamkova, M., et al., "First experience with the use of vacuum assisted closure in the treatment of skin defects at the burn center", Acta. Chir. Plast., 47(1):24-7 (2005).

Venturi, M.L., et al., "Mechanisms and clinical applications of the vacuum-assisted closure (VAC) device: a review", Am. J. Clin. Dermatol., 6(3):185-94 (2005).

Noel, B., "Management of venous leg ulcers", Rev. Med. Suisse, (English abstract on first page, 1 sheet printout from PubMed); 1(16):1062-6, 1068 (Apr. 20, 2005).

Riccio, M. et al., "Delayed microsurgical reconstruction of the extremities for complex soft-tissue injuries", Microsurgery, 25:272-83 (2005).

Sjogren, J., et al., "Clinical outcome after poststernotomy mediastinitis: vacuum-assisted closure versus conventional treatment", Ann. Thorac. Surg., 79(6):2049-55 (Jun. 2005).

Dainty, L.A., et al., "Novel techniques to improve split-thickness skin graft viability during vulvo-vaginal reconstruction", Gynecol. Oncol., 97(3):949-52 (Jun. 2005).

Clubley, L., et al., "Using negative pressure therapy for healing of a sternal wound", Nurs. Times, 101(16):44-6 (Apr. 19, 2005).

Caniano, D.A., et al., "Wound management with vacuum-assisted closure: experience in 51 pediatric patients", J. Pediatr. Surg., 40(1):128-32 (Jan. 2005).

Steenvoorde, P., et al., "Deep infection after ilioinguinal node dissection: vacuum-assisted closure therapy?" Low. Extem. Wounds, 3(4):223-226 (Dec. 2004).

Ryan, T.J., "Evans (1966) exchange and the skin in the light of vacuum-assisted closure, yoga, and maggots", Low. Extrem. Wounds, 3(3):121-2 (Sep. 2004).

Armstrong, D.G., et al., "Decreasing foot pressures while implementing topical negative pressure (vacuum-assisted closure) therapy", Low. Extrem. Wounds, 3(1):12-15 (Mar. 2004).

Wackenfors, A., et al., "Blood flow responses in the peristernal thoracic wall during vacuum-assisted closure therapy", Ann. Thorac. Surg., 79(5):1724-31 (May 2005).

Whelan, C., et al., "Mechanics of wound healing and importance of vacuum-assisted closure® in urology", J. Urol., 173:1463-70 (May 2005).

O'Connor, J., et al., "Vacuum-assisted closure for the treatment of complex chest wounds", Ann. Thorac. Surg., 79 (4):1196-200 (Apr. 2005).

Nugent, N., et al., "Vacuum-assisted closure—A management option for the burns patients with exposed bone", Burns, 31(3):390-393 (May 2005) (Epub Jan. 22, 2005).

Lambert, K.V., et al., "Vacuum assisted closure: a review of development and current applications", Eur. J. Vasc. Endovasc. Surg., 29(3):219-226 (Mar. 2005).

Smith, N., "The benefits of VAC Therapy in the management of pressure ulcers", Br. J. Nurs., 13(22):1359-60, 1362, 1364-65 (Dec. 9, 2004-Jan. 12, 2005).

White, R.A., et al., "Vacuum-assisted closure complicated by erosion and hemorrhage of the anterior tibial artery", J. Orthop. Trauma, 19(1):56-59 (Jan. 2005).

De Geus, H.R.H., et al., "Vacuum-assisted closure in the treatment of large skin defects due to necrotizing fasciitis", Intensive Care Med., 31(4): 601 (1 page) (Apr. 2005) (Epub Jan. 22, 2005).

Samson, D., et al., "Wound-healing technologies: low level laser and vacuum-assisted closure", Evid. Rep. Technol. Assess. (Summ.),(111):1-6, (Dec. 2004).

Gibson, K., "Vacuum-assisted closure", Am. J. Nurs., 104(12):16 (1 page) (Dec. 2004).

Polly Jr., D.W., et al., "Advanced medical care for soldiers injured in Iraq and Afghanistan", Minn. Med., 87(11):42-4 (Nov. 2004).

Stone, P.A., et al., "Vacuum-assisted fascial closure for patients with abdominal trauma", J. Trauma, 57:1082-6 (Nov. 2004).

Connolly, T.P., "Necrotizing surgical site infection after tension-free vaginal tape", Obstet. Gynecol., 104(6):1275-6 (4 pages) (Dec. 2004).

Wackenfors, A., et al., "Effects of vacuum-assisted closure therapy on inguinal wound edge microvascular blood flow", Wound Rep. Regen., 12(6):600-6 (Nov.-Dec. 2004).

Schaffzin, D.M., et al., "Vacuum-assisted closure of complex perineal wounds", Dis. Colon Rectum, 47:1745-8 (Oct. 2004) (Published online Aug. 24, 2004).

Yousaf, M., et al., "Use of vacuum-assisted closure for healing of a persistent perineal sinus following panproctocolectomy: report of a case", Dis. Colon Rectum, 47(8):1403-8 (Aug. 2004) (Published online Aug. 12, 2004).

Fox, A., et al., "An unusual complication of vacuum assisted closure in the treatment of a pressure ulcer", J. Wound Care, 13(8):344-5 (Sep. 2004).

Saxena, V., et al., "Vacuum-assisted closure: microdeformations of wounds and cell proliferation", Plast. Reconstruct. Surg., 114(5):1086-96 (Oct. 2004).

Scholl, L., et al., "Sternal osteomyelitis: use of vacuum-assisted closure device as an adjunct to definitive closure with sternectomy and muscle flap reconstruction", J. Card. Surg., 19(5):453-61 (Sep.-Oct. 2004).

Ohye, R.G., et al. "Primary closure for postoperative mediastinitis in children", J. Thorac. Cardiovasc. Surg., 128(3):480-6 (Sep. 2004).

Tang, S.Y., et al., "Influence of vacuum-assisted closure technique on expression of Bcl-2 and NGF/NGFmRNA during wound healing", Zhonghua Zheng Xing Wai Ke Za Zhi, (English abstract on first page 1 sheet printout from PubMed); 20(2):139-42 (Mar. 2004).

Armstrong, D.G., et al., "Guidelines regarding negative wound therapy (NPWT) in the diabetic foot", Ostomy Wound Manage., 50(4B Suppl.):3S-27S (Apr. 2004).

Shilt, J.S., et al., "Role of vacuum-assisted closure in the treatment of pediatric lawnmower injuries", J. Pediatr. Orthop., 24(5):482-7 (Sep.-Oct. 2004).

Antony, S., et al., "A retrospective study: clinical experience using vacuum-assisted closure in the treatment of wounds", J. Natl. Med. Assoc., 96(8):1073-7 (Aug. 2004).

Steenvoorde, P., et al., "Vacuum-assisted closure therapy and oral anticoagulation therapy", Plast. Reconstruct. Surg., 113(7):2220-1 (Jun. 2004).

Oczenski, W., et al., "Vacuum-assisted closure for the treatment of cervical and mediastinal necrotizing fasciitis", J. Cardiothorac. Vasc. Anesth., 18(3):336-8 (Jun. 2004).

(56) References Cited

OTHER PUBLICATIONS

Carson, S.N., et al., "Vacuum-assisted closure used for healing chronic wounds and skin grafts in the lower extremities", Ostomy Wound Manage., 50(3):52-8 (9 sheets) (Mar. 2004).
Marathe, U.S., et al., "Use of the vacuum-assisted closure device in enhancing closure of a massive skull defect", Laryngoscope, 114(6):961-4 (8 sheets) (Jun. 2004).
Schintler, M.V., et al., "The impact of the VAC-treatment for locally advanced malignancy of the scalp", Zentralbl. Chir., (English abstract on first page, 1 sheet printout from PubMed); 129 Suppl: 1:S141-S146 (May 2004).
Querings, K., et al., "Revitalization of a gluteal abscesses with V.A.C. therapy (vacuum assisted closure)", Zentralbl. Chir., (English abstract on first page, 1 sheet printout from PubMed); 129 Suppl 1:S138-S140 (May 2004).
Kall, S., et al., "Influence of foam- and tubing material of the vacuum assisted closure device (V.A.C.) on the concentration of transforming growth factor beta 1 in wound fluid", Zentralbl. Chir., (English abstract on first page, 2 sheets printout from PubMed); 129 Suppl 1: S113-S115 (May 2004).
Mang, R., et al., "Vacuum therapy in a pre- and postsurgical ulcera crurum", Zentralbl. Chir., (English abstract on first page, 1 sheet printout from PubMed); 129 Suppl 1:S101-S103 (May 2004).
Steiert, A.E., et al., "The V.A.C. system (vacuum assisted closure) as bridging between primary osteosynthesis in conjunction with functional reconstructed of soft tissue—open fractures type 2 and type 3", Zentralbl. Chir., (English abstract on first page, 2 sheets printout from PubMed); 129 Suppl 1:S98-100 (May 2004).
Karl, T., et al., "Indications and results of V.A.C. therapy treatments in vascular surgery—state of the art in the treatment of chronic wounds", Zentralbl. Chir., (English abstract on first page, 1 sheet printout from PubMed); 129 Suppl 1:S74-S79 (May 2004).
Ferbert, T., et al., "Treatment of soft tissue defects on hand and forearm with vacuum assisted closure", Zentralbl. Chir., (English abstract on first page, 1 sheet printout from PubMed); 129 Suppl 1:S57-S58 (May 2004).
Halama, D., et al., "Intraoral application of vacuum-assisted closure in the treatment of an extended mandibular keratocyst", Zentralbl. Chir., (English abstract on first page, 1 sheet printout from PubMed); 129 Suppl 1:S53-S56 (May 2004).
Fleck, T., et al., "Early treatment of sternal wound infections with vacuum assisted closure therapy reduces involvement of the mediastinum and further diminishes the need of plastic reconstructive surgery", Zentralbl. Chir., (1 sheet printout from PubMed); 129 Suppl 1:S35-S37 (May 2004).
Kutschka, I., et al., "Vacuum assisted closure therapy improves early postoperative lung function in patients with large sternal wounds", Zentralbl. Chir., (English abstract on first page, 1 sheet printout from PubMed); 129 Suppl 1: S33-S34 (May 2004).
Labler, L., et al., "New application of V.A.C. (vacuum assisted closure) in the abdominal cavity in case of open abdomen therapy", Zentralbl. Chir., (English abstract on first page, 2 sheets printout from PubMed); 129 Suppl 1:S14-S19 (May 2004).
Wild, T., et al., "Consensus of the German and Austrian Societies for Wound Healing and Wound Management on vacuum closure and the V.A.C. treatment unit", Zentralbl. Chir., (English abstract on first page, 2 sheet printout from PubMed and 1 sheet of erratum); 129 Suppl 1:S7-S11 (May 2004).
Weed, T., et al., "Quantifying bacterial bioburden during negative pressure wound therapy. Does the wound VAC enhance bacterial clearance?" Ann. Plast. Surg., 52(3):276-80 (Mar. 2004).
Mustoe, T., "Understanding chronic wounds: a unifying hypothesis on their pathogenesis and implications for therapy", Am. J. Surg., 187(5A):65S-70S (May 2004).
Tzeng, Y.J., et al., "Using vacuum-assisted closure (VAC) in wound management", Hu Li Za Zhi, (English abstract on last page, 1 sheet printout from PubMed); 51(2):79-83 (Apr. 2004).
Quah, H.M., et al., "Vacuum-assisted closure in the management of the open abdomen: a report of a case and initial experiences", J. Tissue Viability, 14(2):59-62 (Apr. 2004).

Emohare, O., et al., "Vacuum-assisted closure use in calciphylaxis", J. Burn Care Rehabil., 25(2):161-4 (Mar.-Apr. 2004).
Wackenfors, A., et al., "The effect of vacuum-assisted closure therapy on the pig femoral artery vasomotor responses", Wound Repair Regen., 12(2):244-51 (Mar.-Apr. 2004).
Sjogren, J., et al., "Vacuum-assisted closure therapy in mediastinitis after heart transplantation", J. Heart Lung Transplant., 23(4):506-7 (Apr. 2004).
Miller, Q., et al., "Effect of subatmospheric pressure on the acute healing wound", Curr. Surg., 61(2):205-8 (Mar.-Apr. 2004).
Penn, E., et al., "Management of a dehisced abdominal wound with VAC therapy", Br. J. Nurs., 13(4):194, 196, 198-201 (Feb. 26-Mar. 10, 2004).
Moues, C.M., et al., "Bacterial load in relation to vacuum-assisted closure wound therapy: a prospective randomized trial", Wound Repair Regen., 12(1):11-7 (Jan.-Feb. 2004).
Schimp, V.L., et al., "Vacuum-assisted closure in the treatment of gynecologic oncology wound failures", Gynecol. Oncol., 92(2):586-91 (Feb. 2004).
Aru, G.M., et al., "Limitations on the role of vacuum-assisted closure in cardiac surgery", J. Thorac. Cardiovasc. Surg., 127(2):604-5 (Feb. 2004).
Bihariesingh, V.J., et al., "Plastic solutions for orthopaedic problems", Arch. Orthop. Trauma. Surg., 124(2):73-6 (Mar. 2004) (Epub Jan. 17, 2004).
Kaplan, M., "Managing the open abdomen", Ostomy Wound Manage., 50(1A suppl):C2, 1-8, and 1 sheet of quiz (Jan. 2004).
Colwell, A.S., et al., "Management of early groin vascular bypass graft infections with sartorius and rectus femoris flaps", Ann. Plast. Surg., 52(1):49-53 (Jan. 2004).
Evidence Report/Technology Assessment, No. 111, "Wound healing technologies: low-level laser and vacuum-assisted closure", prepared for Agency for Healthcare Research and Quality by the Blue Cross and Blue Shield Association Technology Evaluation Center Evidence-based Practice Center, under Contract No. 290-02-0026, AHRQ Publications Clearinghouse, Available Dec. 2004.
Wolvos, T., "Wound instillation—the next step in negative pressure wound therapy. Lessons learned from initial experiences", Ostomy Wound Manage., 50(11):56-58, 60-66 (Nov. 2004).
Bluman, E.M., et al., "Subatmospheric pressure-induced compartment syndrome of the entire upper extremity. A case report", J. Bone Joint Surg. (Am.), 86-A(9):2041-4 (Sep. 2004).
Kamolz, L.P., et al., "Use of subatmospheric pressure therapy to prevent burn wound progression in human: first experiences", Burns, 30(3):253-8 (May 2004) (Available online Mar. 16, 2004).
Jones, S.M., et al., "Advances in wound healing: topical negative pressure therapy", Postgrad. Med. J., 81 (956):353-7 (Jun. 2005).
Stone, P., et al., "Bolster versus negative pressure wound therapy for securing split-thickness skin grafts in trauma patients", Wounds, 16(7):219-23 (5 sheets) (2004) (Posted Aug. 4, 2004).
Wolvos, T., "Wound instillation with negative pressure wound therapy", Ostomy Wound Manage., 51(2A suppl):21S-26S (Feb. 2005).
Jeter, K., "Closed suction wound drainage system", JWOCN, 31(2):51 (1 sheet) (Mar.-Apr. 2004).
Agarwal, J.P., et al., "Vacuum-assisted closure for sternal wounds: a first-line therapeutic management approach", Plast. Reconstr. Surg., 116(4):1035-1040 (Sep. 15, 2005).
Sjogren, J., et al., "The impact of vacuum-assisted closure on long-term survival after post-sternotomy mediastinitis", Ann. Thorac. Surg., 80(4):1270-5, (Oct. 2005).
Mendez-Eastman, S., "New advances in wound therapy", printout from Wounds1.com; 7 sheets (Apr. 15, 2005).
"Promoting wound healing", Nurses-Digest, 2(3), 6 sheets, Mar. 2005.
Roylance, L., "Nancy Sujeta, Amanda Clark,"DOME, vol. 55, Mar. 2004, 2 sheets of website printout www.hopkinsmedicine.org/dome/0405/feature4.cfm.
Agarwal, J.P., et al., "Vacuum assisted closure™ for sternal wounds: a first line therapeutic management", ASPS, Plastic Surgery 2004, Philadelphia, PA, abstract (2 sheets) (Wednesday Oct. 13, 2004).
Gomoll, A.H., et al., "Incisional vacuum-assisted closure therapy", J. Orthop. Trauma, 20(10):705-709, (Nov.-Dec. 2006).

(56) References Cited

OTHER PUBLICATIONS

Leininger, B.E., et al., "Experience with wound VAC and delayed primary closure of contaminated soft tissue injuries in Iraq", J. Trauma, 61(5):1207-1211 (Nov. 2006).
Gupta, S., ed., "Differentiating negative pressure wound therapy devices: an illustrative case series", Wounds, 19(1 suppl):1-9, (Jan. 2007).
Korasiewicz, L.M., "Abdominal Wound With a Fistula and Large Amount of Drainage Status After Incarcerated Hernia Repair", Journal of Wound, Ostomy & Continence Nursing. 31(3):150-153, (May-Jun. 2004).
Guntinas-Lichius, O., et al., "The role of growth factors for disease and therapy in diseases of the head and neck", DNA and Cell Biol., 22(9):593-606, (Sep. 2003).
Goldman, R., "Growth factors and chronic wound healing: past, present, and future", Adv. Skin Wound Care, 17 (1):24-35, (Jan.-Feb. 2004).
Malli, S., "Keep a close eye on vacuum-assisted wound closure", Nursing, 35(7):25 (Jul. 2005).
Lynch, J.B., et al., "Vacuum-assisted closure therapy: a new treatment option for recurrent pilonidal sinus disease. Report of three cases", Dis. Colon Rectum, 47(6):929-32 (Jun. 2004) (Published online May 4, 2004).
MX: Business Strategies for Medical Technology Executives, (Mar. / Apr. 2005).
Niezgoda, J.A., "Incorporating negative pressure therapy into the management strategy for pressure ulcers", Ostomy Wound Manage., 50(11A suppl.):5S-8S, (Nov. 2004).
Banwell, P.E., "Topical negative pressure therapy: advances in burn wound management", Ostomy Wound Manage., 50(11A suppl.):9S-14S, (Nov. 2004).
Kaplan, M., "Negative pressure wound therapy in the management of abdominal compartment syndrome", Ostomy Wound Manage., 50(11A suppl):20S-25S, (Nov. 2004).
Gupta, S., et al., "The perioperative use of negative pressure wound therapy in skin grafting", Ostomy Wound Manage., 50(11A suppl. ):26S-28S, (Nov. 2004).
Schoemann, M.B., et al., "Treating surgical wound dehiscence with negative pressure dressings", Ostomy Wound Manage., 51(2A suppl. ):15S-20S, (Feb. 2005).
Bookout, K., et al., "Case studies of an infant, a toddler, and an adolescent treated with a negative rpessure wound treatment system", J. Wound OstomyContinence Nurs., 31(4):184-192, (8 pp.) (Jul. / Aug. 2004).
Borkowski, S., "G tube care: managing hypergranulation tissue", Nursing, 35(8):24 (Aug. 2005).
Machen, M. S., "Management of traumatic war wounds using vacuum-assisted closure dressings in an austere environment," Army Medical Department J., pp. 17-23, (Jan.-Mar. 2007).
Peck, M.A., et al., "The complete management of extremity vascular injury in a local population: a wartime report from the 332nd Expeditionary Medical Group/Air Force Theater Hospital, Balad Air Base, Iraq," J. Vasc. Surg., pp. 1-9, (2007), (Presented at the Plenary Session of the Eastern Vascular Society's Twentieth Annual Meeting, Washington D. C., Sep. 30, 2006).
Giovannini, U.M., et al., "Topical negative therapy and vacuum assisted closure. New strategies and devices in surgical reconstruction", Minerva Chir., 60(3):191-4 (Jun. 2005).
Kuznetsov, V.A., et al., Report on Practical Application entitled "Method of vacuum-sorption treatment of purulent wounds," Kazan Municipal Hospital No. 8, (1 sheet in English, 1 sheet in Russian and certificate of translation dated Apr. 28, 2009), (allegedly dated May 19, 1986).
Thomas, S., "Pain and wound management," Community Outlook, pp. 11-13, 15 and one extra sheet, (Jul. 1989).
Livshits, V.S., "Polymer dressings for wounds and burns (review)," All-Union Scientific-Research Institute for Medical Polymers, Moscow, pp. 515-522, (allegedly published in Pharmaceutical Chemical Journal, 22(7):790-798, translated from Russian (allegedly dated Jul. 1988)), Plenum Publishing Corp., (1989).

Calne, S., ed., Position Document: Pain at wound dressings changes, pp. 1-17 and 3 additional sheets, supported by Molnlycke Health Care, (allegedly dated 2002).
Skover, G., et al., "45: New Technologies: An Overview," Chronic Wound Care, pp. 425-430 (allegedly dated 1990).
2 sheets of documents, the citation is alleged to be: David JA, Wound Management: A Comprehensive Guide to Dressing and Healing, pp. 51-51 (allegedly dated 1986).
Thomas, S., "Selecting dresssings," Community Outlook, vol. 6, 4 sheets, (Jun. 1991).
1 sheet document, the citation is alleged to be: David J., Extract from Practical Nursing Handbook: Wound Management: A Comprehensive Guide to Dressing and Healing, pp. 166-167, (allegedly dated 1986).
Dunphy, J.E., ed., et al., "Current Surgical Diagnosis & Treatment" 5th ed., pp. 946-951, with 5 additional sheets, Lange Medical Publications, Los Altos, CA (1981).
British Pharmacopoeia, vol. II, pp. 903-940, London (1980).
British Pharmacopoeia 1980, pp. A81, 542, 546-549, with annotations, London—Addendum (1986).
Wagner, D.R., et al., "Combined parenteral and enteral nutrition in severe trauma," Nutrition in Clinical Practice, 7:113-116 with additional sheet, (1992).
Krizek, T.J., et al., "The use of prophylactic antibacterials in plastic surgery: A 1980s update," Plast. Reconstr. Surg., 76(6): 953-962, (Dec. 1985).
Parikh, R.S., et al., "Self-adhesive drape (Opsite) for management of leaking abdominal wounds", Indian J. Gastroenterol., 19(4):178-180 (Oct. / Dec. 2000).
Alexis, A.F., et al., "Reassessment of the suction blister model of wound healing: introduction of a new higher pressure device", Int. J. Dermatol., 38(8):613-617 (Aug. 1999).
Gnanaraj, J., "A simple, sterile, low-cost, closed suction drainage system", Trop. Doct., 27(2):104 (Apr. 1997).
Klemm, K.W., "Antibiotic bead chains", Clin. Orthop. Rel. Res., (295):63-76 (Oct. 1993).
Pignatti, M., et al., "Mobile-VAC for the treatment of lower limb ulcers", Plast. Reconstr. Surg., 108(6):1837-1838 (Nov. 2001).
Schaum, K.D., "Payment strategies: a new medicare part B wound care policy", Adv. Skin & Wound Care, 14 (5):238-240 (Sep. / Oct. 2001).
Banwell, P.E., et al., "Topical negative pressure (TNP): the evolution of a novel wound therapy," J. Wound Care, 12(1):22-8 (Jan. 2003).
Cardozo, M., "A case study of holistic wound management in intensive care", Br. J. Nurs., 12(11 Suppl):S35-37, S40-42 (Jun. 2003).
Collier, M., "Topical negative pressure therapy", Nurs. Times, 99(5):54-5 (Feb. 4-10, 2003).
Domkowski, P.W., et al., "Evaluation of vacuum-assisted closure in the treatment of poststerotomy mediastinitis," J. Thorac. Cardiovasc. Surg., 126(2):386-90 (Aug. 2003).
Eginton, M.T., et al., "A prospective randomized evaluation of negative-pressure wound dressings for diabetic foot wounds", Ann. Vasc. Surg., 17(6):645-9 (2003).
Ferreira, M.C., et al., "The vacuum assisted closure of complex wounds: report of three cases", Rev. Hosp. Clin. Fac. Med. S. Paulo, 58(4):227-30 (2003).
Fisher, A., et al., "Vacuum assisted wound closure therapy", Issues Emerg. Health Technol., Issue 44, 6 pp. (Mar. 2003).
Hallberg, H., et al., "Vaginal construction with skin grafts and vacuum-assisted closure", Scand. J. Plast. Reconstr. Surg. Hand Surg., 37(2):97-101 (2003).
Hess, C.L., et al., "A review of mechanical adjuncts in wound healing: hydrotherapy, ultrasound, negative pressure therapy, hyperbaric oxygen, and electrostimulation", Ann. Plast. Surg., 51(2):210-8 (Aug. 2003).
Hodzic, J., et al., "Vacuum sealing of extensive wound healing disorders after kidney transplantation," Urologe A., (6 sheets in German, English abstract on p. 2 and 1 sheet printout from PubMed); 42(8):1097-100 (Aug. 2003) (Epub Apr. 3, 2003).
Kaufman, M.W., et al., "Vacuum-assisted closure therapy: wound care and nursing implications", Dermatol. Nurs., 15 (4):317-20, 323-236 (Aug. 2003).

(56) References Cited

OTHER PUBLICATIONS

Luckraz, H., et al., "Vacuum-assisted closure as a treatment modality for infections after cardiac surgery", J. Thorac. Cardiovasc. Surg., 125(2):301-5 (Feb. 2003).
Svedman, P., "A dressing allowing continuous treatment of a biosurface," IRCS Medical Science: Biomedical Technology; Clinical Medicine; Surgery and Transplantation, 7:221 (1979). (Exhibit D-407).
Meyer, W., et al., "Bier's Hyperemic Treatment," W.B. Saunders & Co., 1908 (Exhibit D246).
Svedman, P., et al., "Staphylococcal wound infection in the pig: Part I. Course," Ann. Plast. Surg., 23(3):212-218, (Sep. 1989).
Sanden, G., et al., "Staphylococcal wound infection in the pig: Part II. Inoculation, quanitification of bacteria, and reproducibility," Ann. Plast. Surg., 23(3):219-223, (Sep. 1989).
Westaby, S., et al., "A wound irrigation device," Lancet, pp. 503-504, (Sep. 2, 1978).
Taber's Cyclopedic Medical Dictionary, 16th edition, pp. 613-614, 643, 679, 1444, and 1686-1688, (1989).
Parker, S.P., ed., McGraw-Hill Dictionary of Scientific and Technical Terms, 4th ed., pp. 1462, (1989).
Gove, P.B., ed., Webster's Third New International Dictionary Unabridged, pp. 869 and 2627 (1986).
Peacock, Jr., E.E., Wound Repair, 3d edition, W.B. Saunders Company pp. 12-14, pp. 38-51, Chapter 6 Repair of skin wounds, (1984).
Spartanburg Regional Medical Center Operative reports, 35 sheets, dated 1989.
Johnson, F.E, "Expanded use of suction drains," pp. 469 and 1 sheet of drawings (allegedly dated 1985).
Brossy, J.-J., "Foam elastomer dressings in surgery," SA Medical Journal, 59:559-560, (Apr. 1981).
Groves, A.R., et al., "Silastic foam dressing: an appraisal," Annals of the Royal College of Surgeons of England, vol. 67, pp. 117-118 and additional page, (1985).
Harding, K.G., et al., "Silastic foam dressing for skin graft donor sites—a preliminary report," Br. J. Plast. Surg., 33:418-421, (1980).
Malone, W.D., "Wound dressing adherence: a clinical comparitive study," Archives of Emergency Medicine, 4:101-105, (1987).
Moblvac II advertising materials, 4 sheets, allegedly dated 1984.
Bucknall, T.E. ed., et al., "Wound healing for surgeons," Introduction, Chapter 1 The healing wound, Chapter 2 Wound strength, Chapter 3 Factors affecting healing, Chapter 4 Sutures and dressings, Chapter 5 Clinical trials, Chapter 6 Skin healing and burns, and Chapter 7 The abdominal wall, (1984).
Brubacher, L.L., "To heal a draining wound," RN, 45(3):30-36 (Mar. 1982).
Dahlin, P.A., et al., "Cerebrospinal fluid leak because of pressure sore fistula in a quadriplegic," Spine, 12(1):72-75, (1987).
Downie, P.A., ed., Cash's textbook of medical conditions for physiotherapists, Chapter 1 Inflammation and healing, Chapter 2 Oedema, Chapter 19 Skin conditions, Chapter 20 Burns, B. Lippincott Co., (1979).
Ersh, Z. Ya., "Use of polyurethane foam for cleaning of purulent cavities and wounds," I.I. Grekov J. of Surg., 133 (9):134-135 and additional sheets (10 sheets in English and 5 sheets in Russian) (1984).
Fasol, P., et al., "The foil vacuum dressing for the treatment of infected skin defects," Acta Chir. Austriaca 116-118, (2 sheets English and 3 sheets German) (1976).
Gruendemann, B.J., et al., Alexander's Care of the patient in surgery, 8th ed., C.V. Mosby Co., pp. 138-139 (1987).
Kirk-Othmer Encyclopedia of chemical technology, 3d ed., vol. 8, pp. 201-203 (1979).
Kostyuchenok, B.M., et al., "Vacuum treatment of purulent wounds," Soviet Medicine, pp. 18-21, (4 sheets English, 4 sheets Russian, with English abstract on last page), (1984).
Kuzin, M.I., et al., "Method of vacuum treatment of wounds," Wounds and Wound Infection, pp. 348-350, (2 sheets) (1981).

Kuzin, M.I., ed., et al., "Vacuum treatment of a purulent wound," Wounds and Wound Infection, Handbook for Physicians, 2nd revised and supplemented ed., pp. 243-246, (3 sheets) (1990).
Tranchell, H.G., et al., Circulatory Ulcers A Physicial Approach, John Wright & Sons Ltd., Bristol, Foreword, I. Ulcers: a comparison, II. The ulcer, pp. 44-47, and 54-55, (1960).
Parish, L.C., et al., "The infected decubitus ulcer," Int. J. Dermatol., 28:643-647 (Dec. 1989).
Davydov, Y.A., et al., "Device and method for vacuum therapy of purulent lactation mastites," Khirurgiya, (4):131-132, (Apr. 1988).
Davidov, Y.A., et al., "Justifying the usage of forced early secondary sutures in treatment of purulent wounds by the vacuum therapy," Vestnik Chirugia 126-129, (2 sheets in English and 3 sheets in Russian) (Mar. 1990).
Davydov, Y.A., et al., "Pathogenic mechanisms of the effect of vacuum therapy on the course of the wound process," Khirurgiya, 6:42-47 (7 sheets English and 8 sheets Russian, with English abstract on pp. 46-47) (1990).
Davydov, Y.A., et al., "Bacteriological and cytological evaluation of vacuum therapy of purulent wounds", Vestnik khirurgii, 10:48-52, (5 sheets English, 5 sheets Russian, English abstract on pp. 52) (Received 1987).
Davydov, Y.A., et al., "Vacuum therapy in the treatment of purulent lactation mastitis," pp. 66-70 (5 sheets English, 5 sheets Russian, English abstract on pp. 70) (Received 1986).
Davydov, Y.A., et al., "Vacuum therapy in the treatment of acute purulent diseases of soft tissues and purulent wounds", Vest. Khir. 141(9):43-46 (6 sheets English, 6 sheets Russian, English abstract on pp. 46) (1988).
Demorest, R.L., "New standards in water vapour permeability testing," British Plastics & Rubber, 3 sheets, (handwritten label on first sheet shows "Exhibit TT"), (May 1995).
Kirk-Othmer, Encyclopedia of Chemical Technology, 2nd completely revised edition, vol. 9, pp. 220-232, John Wiley & Sons, Inc., (1966).
Stedman's Medical Dictionary, 25th ed., pp. 1739, Williams & Wilkins, (1990).
Standard Operating Procedure, The determination of moisture vapour permeability (MVP) and water transmission rate (WTR), implementation date: Sep. 11, 2006 and QA Operational Laboratories Analytical Report dated Nov. 13, 2008.
British Pharmacopoeia Selections: (1988) vol. II, p. 1126-1127, A223-A224; Addendum 1992, p. 1494; (1993) vol. II, p. 1266, A218-A219.
Solovev, V.A., "Treatment and prevention of suture failures after gastric resection," Dissertation abstract, with alleged index card, S.M. Kirov Gorky State Medical Institute, Gorky, U.S.S.R., (Exhibit I of Third party comments) (1988).
Solovev, V.A., "The method of treatment of immature external fistulas in the upper gastrointestinal tract," S.M. Kirov Gorky State Medical Institute, Gorky, U.S.S.R., (Exhibit J of Third party comments) (1987).
Thomas, S., "Wound Management and Dressings," The Pharmaceutical Press, London, 223 sheets, (1990).
Wood, R.A.B., et al., "A new method for treatment of open granulating wounds," Surgical Dressings in the Hospital Environment, T.D. Turner, ed., et al., Surgical Dressings Research Unit, Welsh School of Pharmacy, Uwist, Cardiff, 8 sheets, (1975).
Turner, T.D., ed., et al., Advances in Wound Management, including "The role of foam dressings in wound management" by S. Thomas, "Clinical aspects of Synthaderm®" by T. Martin, et al., "Lyofoam®—Used in the treatment of leg ulcers" by J. Creevy, and "Clinical experience of Silastic® foam dressing," by K.G. Harding; John Wiley & Sons, 17 sheets, (Proceedings dated Mar. 20-21, 1985) (1986).
PCT/US08/79364—Written Opinion and International Search Report P04263WO0-ISR (Dec. 16, 2008).
Bagautdinov, N.A., "Variant of external vacuum aspiration in the treatment of purulent disease of soft tissue," pp. 94-96 and Introduction by V.E. Volkov and an opinion by V. V. Shutova dated Feb. 4, 2009, in Russian with English translation, with alleged card cata-

(56) References Cited

OTHER PUBLICATIONS logue card with English translation, and certification of translation dated Feb. 19, 2009, Current Problems in Modern Clinical Surgery, (1986).

Kuznetsov, V.A., "Vacuum and vacuum-sorption treatment of open septic wounds," in II All-union conference "Wounds and wound infection" "(Abstracts of presentations)" in Russian with English translation, and card with English translation, Moscow, Oct. 28-29, 1986.

Robson, M.C., et al., Chapter 10 "Wounds and wound healing," p. 107-114 in Essentials of General Surgery, P.F. Lawrence ed., Williams & Wilkins, (1988).

Robson, M.C., et al., Chapter 11 "Wounds and wound healing," p. 119-126 in Essentials of General Surgery, 2nd edition, P.F. Lawrence ed., Williams & Wilkins, (1992).

Smith, D.J. Jr., et al., Chapter 7 "Wounds and wound healing," p. 113-122 in Essentials of General Surgery, 3d edition, P.F. Lawrence ed., Lippincott Williams & Wilkins, (2000).

Talboy, G.E., et al., "Chapter 8: Wounds and wound healing," p. 147-161 in Essentials of General Surgery, B. Sun ed., Lippincott Williams & Wilkins, (2006).

Garrison, R.N., et al., "Chapter 9: Surgical infections," p. 163-179 in Essentials of General Surgery, B. Sun ed., Lippincott Williams & Wilkins, (2006).

Sumpio, B.E., et al., "Role of negative pressure wound therapy in treating peripheral vascular graft infections," Vascular, 16(4):194-200, (2008).

Taber's Cyclopedic Medical Dictionary, Edition 20, pp. 306-309, 728-729, 765, 1726, and 2006-2009. (2005).

Mills, N., Polymer Foams Handbook: engineering and biomechanics applications and design guide, pp. 2-3, (2007).

Bucknall, T.E., et al., eds., "Sutures and dressings," p. 88-93 in Wound Healing for Surgeons, (1984).

Parker, S.P., ed., McGraw-Hill Dictionary of Scientific and Technical Terms, 5th ed., pp. 139, 533, 772, and 1672 (1994).

Alger, M.S.M., Polymer Science Dictionary, (4 sheets), Elsevier Science Publishers Ltd. (1989).

Stedman's Medical Dictionary, 25th ed., pp. 554, 667-668, and 1603-1604, Williams & Wilkins, (1990).

Webster's New World Dictionary of the American Language, pp. 1105, Simon & Schuster, Inc., (1984).

Transeal transparent wound dressing, DeRoyal, 4 sheets (2003).

Kuznetsov, V.A., "Vacuum and vacuum-sorption treatment of open septic wounds," in II All-union conference "Wounds and wound infections" "(Presentation abstracts)" in Russian with English translation dated Apr. 2, 2009, with table of contents, Moscow, Oct. 28-29, 1986.

British Pharmacopoeia 19, vol. II, p. 927 and p. 548 of 1986 addendum, (vol. II—1980, addendum—1986).

KCI, "The V.A.C. operations summary," 7 sheets, (1999).

Kanshin, N.N., "Closed treatment of suppurative processes by the method of active lavage drainage," Third Surgical Clinic of the N.V. Sklifosovkiy Moscow Scientific Research Institute of Emergency Care, pp. 18-23, (6 sheets in English, 6 sheets in Russian and English abstract on pp. 22-23), allegedly submitted 1979.

Lokhvitskii, S.V., et al., "External vacuum aspiration in the treatment of purulent disorders of the soft tissues," Inpatient Surgery Clinic of the Therapeutic Department at Karagandy Medical Institute, Municipal Hospital No. 1, Temirtau, pp. 130-134 (5 sheets English, 5 sheets Russian), allegedly submitted Sep. 22, 1982.

Ersh, Z. Ya., "Use of polyurethane foam for treating purulent cavities and wounds," Purulent Septic Unit of Hospital No. 35, (2 sheets English and 2 sheets Russian), allegedly submitted for publication Mar. 21, 1984.

3M™ Tegaderm™ Transparent film dressings—wound, Commonly asked questions, 4 sheets, (Jan. 2007).

Greene, A.K., et al., "Microdeformational wound therapy," Ann. Plast. Surg., 56(4):418-422, (2006).

Bui, T.D., et al., "Negative pressure wound therapy with off-the-shelf components," Am. J. Surg., 192:235-237, (2006).

Larichev, A.B., et al., "Vacuum-therapy in the complex of treatment of festering wounds," Khirurgiia (Mosk.), 6:22-26, (13 sheets English translation, 5 sheets in Russian, English abstract on pp. 22), (2008).

Scherer, S.S., et al., "The mechanism of action of the vacuum-assisted closure device," Plast. Reconstr. Surg., 122: 786-797, (presented at the Wound Healing Society Meeting 2007 in Tampa, Florida, Apr. 28-May 1, 2008).

Bagautdinov, N.A., "Variant of external vacuum aspiration in the treatment of purulent diseases of soft tissues," Current Problems in Modern Clinical Surgery, Interdepartmental Collection, Cheboksary, pp. 94-96, and library card, in English and Russian, (KCI_Con00220647-59) (1986).

Kuznetsov, V.A., et al., "Vacuum and vacuum-sorption treatment of open purulent wounds," II All-Union Conference "Wounds and Wound Infections" Moscow, pp. 91-92, with library card and table of contents, in English and Russian, (KCI_Con00220660-89) (1986).

Williams, R.S., "A simple technique for successful primary closure after excision of pilonidal sinus disease," Ann. R. Coll. Surg. England, 72:313-315, (only 2 sheets provided), (1990).

Gray, A.J., et al., "Small bowel perforation following vacuum suction drainage," J. R. Coll. Surg. Edinb. 30(5):324-5 and additional sheet, (Oct. 1985).

Kumar, A.R., "Standard wound coverage techniques for extremity war injury," J. Am. Acad. Orthop. Surg., 14:S62-S65, (2006).

Helgeson, M.D., et al., "Bioartificial dermal substitute: A preliminary report on its use for the management of complex combat-related soft tissue wounds," J. Orthop. Trauma, 21(6):394-399, (Jul. 2007).

Ingari, J.V., et al., "Civilian and detainee orthopaedic surgical care at an air force theater hosptial," Tech. Hand Upper Extr. Surg., 11(2):130-134, (2007).

Covey, D.C., "Combat orthopaedics: A view from the trenches," J. Am. Acad. Orthop. Surg., 14:S10-S17, (2006).

Andersen, R.C., et al., "Definitive treatment of combat casulties at military medical centers," J. Am. Acad. Orthop. Surg., 14:S24-S31, (2006).

Wagner, D. R., et al., "Bioelectrical impedance as a discriminator of pressure ulcer risk," Adv. Wound Care, 9 (2):30-37, (1996).

Mulder, G.D., et al., "Prospective randomized study of the efficacy of hydrogel, hydrocolloid, and saline solution-moistened dressings on the management of pressure ulcers," Wound Rep. Reg., 1:213-218, (1993).

Tintle, T.E., et al., "Early experience with a calcium alginate dressing," Ostomy/Wound Management, pp. 74-81, (May/Jun. 1990).

Jeter, K.F., et al., "Comprehensive wound management with a starch-based copolymer dressing," J. Enterostom. Ther., 13(6):217-225, (Nov.-Dec. 1986).

Winter, G.D., "Formation of the scab and the rate of epithelization of superficial wounds in the skin of the young domestic pig," Nature, No. 4812, p. 293-294 (Jan. 20, 1962).

Robson, M.C., et al., "Bacterial quantification of open wounds," Military Medicine, pp. 19-24, (Jan. 1969).

Jackson, D.M., "The diagnosis of the depth of burning," Br. J. Surgery, 40(164):588-596 and 7 additional sheets, (May 1953).

Morykwas, M.J., "38: Vacuum-assisted closure of wounds" in "Wound Healing," A. Falabella et al., eds., Taylor & Francis, NY, pp. 503-515, (2005).

DeFranzo, A.J., et al., "Vacuum assisted closure for the treatment of abdominal wounds," Clin. Plast. Surg. 33(2): 213-224 (Apr. 2006).

Defranzo, A.J., et al., "Vacuum-assisted closure for defects of the abdominal wall," Plast. Reconstr. Surg., 121 (3):832-839, (Mar. 2008).

Park, C.A., et al., "Breast asymmetry: presentation of a giant fibroadenoma," Breast J., 12(5):451-461, (2006).

Zannis, J., et al., "Comparison of fasciotomy wound closures using traditional dressing changes and the Vacuum-Assisted Closure device," Ann. Plast. Surg., 62(4):407-409, (Apr. 2009).

Thompson, J.T., et al., "Outcome analysis of helmet therapy for positional plagiocephaly using a three-dimensional surface scanning laser," J. Craniofasc. Surg., 20(2):362-365, (Mar. 2009).

Argenta, L.C., et al., "Advances in hemangioma evaluation and treatment," J. Craniofac. Surg., 17(4):748-755 (Jul. 2006).

(56) References Cited

OTHER PUBLICATIONS

Plikaitis, C.M., et al, "Neurocutaneous melanosis: clinical presentations," J. Craniofac. Surg., 16(5):921-925 (Sep. 2005).
David, L.R., et al., "Proboscis lateralis: a rare craniofacial anomaly, reconstruction, and long-term evaluation," J. Craniofac. Surg., 19(4):1107-1113, (Jul. 2008).
Sanger, C., et al., "Dynamic spring mediated cranioplasty in an experimental model with resorbable foot plates," J. Craniofac. Surg., 18(1):54-59, (Jan. 2007).
Morykwas, M.J., et al., "Vacuum-assisted closure: state of basic research and physiologic foundation," Plast. Reconstr. Surg., 117(7) (Suppl): 121S-126S, (Jun. 2006).
Hill, C.A., et al. "Superior sternal cleft repair using autologous rib grafts in an infant with complex congenital heart disease," Ann. Thorac. Surg., 84:673-4, (2007).
McGee, M.P., et al., "Swelling and pressure-volume relationships in the dermis measured by osmotic-stress technique," Am. J. Physiol. Regul. Integr. Comp. Physiol., 296:R1907-R1913, (Mar. 25, 2009).
Morykwas, M., "Vacuum assisted closure," 91 sheets of slides.
Morykwas, M., et al., "El uso de la plantilla de regeneracion integra en la cirugia reconstructiva," 121 sheets of slides.
Morykwas, M., et al., "Aplicaciones de tratamientos con presion sub-atmosferica en el cuidado de quemaduras," 140 sheets of slides.
Argenta, A., et al., "Deformation of superficial and deep abdominal tissues with application of a controlled vacuum", 1 sheet.
*Kinetic Concepts, Inc., et al.*, v. *Bluesky Medical Corporation, et al.*, Civil Action No. SA-03-CA-0832-RF, U.S. District Court, W. Dist. of Texas San Antonio Div., Promotional Slide Presentation BlueSky Medical Negative Pressure Wound Care with Versatile 1 Presentation Presented by Penny Campbell and Shelly Burdette-Taylor 27 pages (dated Oct. 14, 2005).
Barillo, D., et al., "Management of Burns to the Hand", Wounds 15,(1):4-9, 2003 Health Management Publications, Inc., Posted Feb. 12, 2003.
Medical Technology & Innovation, "Medical Technology is Extending Life, Reducing Costs", vol. 1, Issue 46, Dec. 4, 2000.
Wu, Lisa C., et al., "Vacuum-Assisted Closure for the Treatment of Sternal Wounds: The Bridge Between Debridement and Definitive Closure", printout from www.plasticsurgery.org, 3 pages (printout dated Apr. 20, 2005).
Bertone, A., "Management of Exuberant Granulation Tissue", Wound Management, pp. 551-562 (Dec. 1989).
Taber's Cyclopedic Medical Dictionary, Edition 18, pp. 937, 942 and 1375.
Harris, Ann, et al., "Hypergranulation Tissue: a Nontraumatic Method of Management", Ostomy/Would Management, vol. 40, No. 5, Jun. 1994.
Webster's New Universal Unabridged Dictionary Deluxe Second Edition, p. 631.
Chariker-Jeter Technique Tutorial by Penny E. Campbell, Wound Care Solutions, 1 page tutorial chart.
Bluesky Medical, Negative Pressure Wound Therapy, Product Catalog Fall 2005, "Finally a choice . . . " 8 pages.
Chariker-Jeter Status Link from the website www.trademark.com/cbi-bin/tmlist, Oct. 14, 2005, 1 page.
Bluesky Medical Support, printout of webpages www.woundvacuum.com/Standard%20Pages/support.htm, Oct. 11, 2005, pp. 1-3.
Van Susante, J.L.C., et al., "Linkage of chondroitin-sulfate to type I collagen scaffolds stimulates the bioactivity of seeded chondrocytes in vitro," Biomaterials, 22:2359-2369 (2001).
Wang, Y., et al., "A tough biodegradable elastomer," Nature Biotechnology, 20:602-606 (Jun. 2002).
Sasaki, N., et al., "Stress-strain curve and Young's Modulus of a collagen molecule as determined by the x-ray diffraction technique," J. Biomechanics, 29(5):655-658 (1996).
Nagata, M., et al., "Synthesis, characterization, and enzymatic degradation of network aliphatic copolyesters," Journal of Polymer Science: Part A: Polymer Chemistry, 37:2005-2011 (1999).

Causa, F., et al., "A multi-functional scaffold for tissue regeneration: The need to engineer a tissue analogue," Biomaterials, 28(34):5093-5099 (Dec. 2007; available online Aug. 6, 2007).
Nair, L.S., et al., "Development of novel tissue engineering scaffolds via electrospinning," Expert Opin. Biol. Ther. 4 (5):659-668 (May 2004), (2 sheets), abstract.
Webb, A.R., et al., "Biodegradable polyester elastomers in tissue engineering," Expert Opin. Biol. Ther. 4(6):801-812 (2004).
Zhong, S.P., et al., "Development of a novel collagen-GAG nanofibrous scaffold via electrospinning," Materials Science and Engineering: C, 27(2):262-266 (Mar. 2007) (available online Jun. 8, 2006).
Li, C., et al., "Electrospun silk-BMP-2 scaffolds for bone tissue engineering," Biomaterials, 27(16):3115-3124 (Jun. 2006) (available online Feb. 3, 2006).
Teo, W.E., et al., "Electrospun scaffold tailored for tissue-specific extracellular matrix," Biotechnology Journal, 1 (9):918-929 (Sep. 2006) (published online Aug. 28, 2006).
Yi, F., et al., "Poly(glycerol sebacate) nanofiber scaffolds by core/shell electrospinning," Macromol. Biosci. 8:803-806 (2008).
Wang, Y., et al., "In vivo degradation characteristics of poly(glycerol sebacate)," J. Biomed Mater Res A, 66 (1):192-197 (Jul. 1 2003) (published online Jun. 10, 2003).
Ifkovits, J.L., et al., "Biodegradable and radically polymerized elastomers with enhanced processing capabilities," Biomed Mater. 3(3):034104 (Sep. 2008) (published Aug. 8, 2008).
Venugopal, J.R., et al., "Nanobioengineered electrospun composite nanofibers and osteoblasts for bone regeneration," Artif. Organs 32(5):388-397 (2008).
Heydarkhan-Hagvall, S., et al., "Three-dimensional electrospun ECM-based hybrid scaffolds for cardiovascular tissue engineering," Biomaterials 29(19):2907-2914 (Jul. 2008; available online Apr. 9, 2008).
Chen, D., et al., "Application of electrostatic spinning technology in nano-structured polymer scaffold," Zhongguo Xiu Fu Chong Jian Wai Ke Za Zhi, 21(4):411-415 (Apr. 2007), 1 sheet abstract.
Qiu, H., et al., "A citric acid-based hydroxyapatite composite for orthopedic implants," Biomaterials 27:5845-5854 (2006) (available online Aug. 21, 2006).
Nair, L.S., et al., "Nanofibers and nanoparticles for orthopaedic surgery applications," J. Bone Joint Surg. Am. 90 (Supp. 1):128-131 (2008).
Abdel-Fattah, W.I., et al., "Synthesis, characterization of chitosans and fabrication of sintered chitosan microsphere matrices for bone tissue engineering," Acta Biomaterialia 3:503-514 (2007).
Li, M., et al., "Co-electrospun poly(lactide-co-glycolide), gelatin, and elastin blends for tissue engineering scaffolds," J. Biomed. Mater. Res. A. 79(4):963-973 (Dec. 15, 2006) (published online Aug. 31, 2006).
Li, M., et al., "Electrospun blends of natural and synthetic polymers as scaffolds for tissue engineering," Conf. Proc. IEEE Eng. Med. Biol. Soc. 6:5858-5861 (2005), 1 sheet abstract.
Yang, X., et al., "Multifunctional nanofibrous scaffold for tissue engineering," Journal of Experimental Nanoscience 3 (4):329-345 (2008).
Hoshi, R.A., "Nanoporous biodegradable elastomers," Adv. Mater. 21:188-192 (2009).
Yang, J., et al., "Synthesis and evaluation of poly(diol citrate) biodegradable elastomers," Biomaterials 27:1889-1898 (2006; available online Nov. 15, 2005).
Yoshimoto, H., et al., "A biodegradable nanofiber scaffold by electrospinning and its potential for bone tissue engineering," Biomaterials 24(12):2077-2082 (May 2003).
Ndreu, A., et al., "Electrospun biodegradable nanofibrous mats for tissue engineering," Nanomedicine (Lond.) 3 (1):45-60 (Feb. 2008), 1 sheet abstract.
Kim, S.S., et al., "Accelerated bonelike apatite growth on porous polymer/ceramic composite scaffolds in vitro," Tissue Eng. 12(10):2997-3006 (Oct. 2006).
Li, M., et al., "Electrospun protein fibers as matrices for tissue engineering," Biomaterials 26(30):5999-6008 (Oct. 2005) (available online May 13, 2005).

(56) References Cited

OTHER PUBLICATIONS

Kidoaki, S., et al., "Mesoscopic spatial designs of nano- and microfiber meshes for tissue-engineering matrix and scaffold based on newly devised multilayering and mixing electrospinning techniques," Biomaterials 26(1):37-46 (Jan. 2005) (available online Mar. 2, 2004).

Ma, Z., et al., "Potential of nanofiber matrix as tissue-engineering scaffolds," Tissue Engineering 11(1/2):101-109 (2005).

Faria, M.L.E., et al., "Recombinant human bone morphogenetic protein-2 in absorbable collagen sponge enhances bone healing of tibial osteotomies in dogs," Veterinary Surgery 36(2):122-131 (Feb. 2007; first published online Mar. 2, 2007).

Li, W.J., et al., "Fabrication and characterization of six electrospun poly(alpha-hydroxy ester)-based fibrous scaffolds for tissue engineering applications," Acta Biomater 2(4):377-385 (Jul. 2006; published online May 6, 2006).

Smith, L.A., et al., "Nano-fibrous scaffolds for tissue engineering," Colloids and Surfaces B: Biointerfaces 39 (3):125-131 (Dec. 10, 2004; available online Feb. 4, 2004).

Wang, W., et al., "Biodegradable polyurethane based on random copolymer of L-lactide and $\epsilon$-caprolactone and its shape-memory property," J. Appl. Polym. Sci. 104:4182-4187 (2007).

Chen, Y., et al., "Increased osteoblast functions in the presence of BMP-7 short peptides for nanostructured biomaterial applications," J. Biomed. Mater. Res. A 91:296-304 (2009; published online Nov. 3, 2008).

Chronakis, I.S., "Novel nanocomposites and nanoceramics based on polymer nanofibers using electrospinning process—A review," Journal of Materials Processing Technology 167:283-293 (2005).

Guan, J., et al., "Preparation and characterization of highly porous, biodegradable polyurethane scaffolds for soft tissue applications," Biomaterials 26:3961-3971 (2005; available online Dec. 8, 2004).

Kim, H.W., et al., "Bioactive glass nanofiber-collagen nanocomposite as a novel bone regeneration matrix," J. Biomed. Mater. Res. A 79:698-705 (2006; published online Jul. 18, 2006).

Nair, L.S., et al., "Biodegradable polymers as biomaterials," Prog. Polym. Sci. 32:762-798 (2007; available online Jun. 11, 2007).

Zhang, Y., et al., "Electrospun biomimetic nanocomposite nanofibers of hydroxyapatite/chitosan for bone tissue engineering," Biomaterials 29:4314-4322 (2008; available online Aug. 20, 2008).

Wan, Y., et al., "Biphasic scaffold for annulus fibrosus tissue regeneration," Biomaterials 29:643-652 (2008; available online Nov. 13, 2007).

Um, I.C., et al., "Electro-spinning and electro-blowing of hyaluronic acid," Biomacromolecules 5:1428-1436 (2004; published online May 7, 2004).

Boland, E.D., et al., "Electrospinning polydioxanone for biomedical applications," Acta Biomaterialia 1:115-123 (2005).

Ji, Y., et al., "Electrospun three-dimensional hyaluronic acid nanofibrous scaffolds," Biomaterials 27:3782-3792 (2006; available online Mar. 23, 2006).

Fujihara, K., et al., "Guided bone regeneration membrane made of polycaprolactone/calcium carbonate composite nano-fibers," Biomaterials 26:4139-4147 (2005; available online Dec. 24, 2004).

Sethuraman, S., et al., "Novel low temperature setting nanocrystalline calcium phosphate cements for bone repair: Osteoblast cellular response and gene expression studies," J. Biomed. Mater. Res. A 82:884-891 (2007; published online Mar. 2, 2007).

Deng, M., et al., "Miscibility and in vitro osteocompatibility of biodegradable blends of poly[(ethyl alanato) (p-phenyl phenoxy) phosphazene] and poly(lacitic acid-glycolic acid)," Biomaterials 29:337-349 (2008; available online Oct. 17, 2007).

Lu, X.L., et al., "Shape memory property of poly(L-lactide-co-$\epsilon$-caprolactone) copolymers," Materials Science and Engineering A 438-440:857-861 (2006).

Leonelli, C., et al., "Synthesis and characterization of cerium-doped glasses and in vitro evaluation of bioactivity," Journal of Non-Crystalline Solids 316:198-216 (2003).

Banwell, P., et al., "Topical Negative Pressure TNP Focus Group Meeting", Proceedings, London, UK 2003, pp. 1-111.

Proceedings from the 2003 National V.A.C.® Education Conference, supplement to the Apr. 2004 Wounds, 40 pages.

Dieu, T., et al., "Too Much Vacuum-Assisted Closure", ANZ J. Surg. 2003; 73: 1057-1060.

Chester, D., et al., "Adverse Alteration of Wound Flora with Topical Negative-Pressure Therapy: A Case Report", British Journal of Plastic Surgery, 2002, pp. 510-511.

Alvarez, A., et al., "Vacuum-Assisted Closure for Cutaneous Gastrointestinal Fistula Management", Gynecologic Oncology, 80, 413-416 (2001).

Nienhuijs, S.W., et al., "Can Topical Negative Pressure Be Used to Control Complex Enterocutaneous Fistulae?", Journal of Wound Care, V. 12, No. 9, Oct. 2003, pp. 343-345.

Erdmann, D., et al., "Abdominal Wall Defect and Enterocutaneous Fistula Treatment with the Vacuum-Assisted Closure (V.A.C.) System", Plastic and Reconstructive Surgery, vol. 108, No. 7, pp. 2066-2068 (Dec. 2001).

Lohman, R., et al., "Discussion: Vacuum Assisted Closure: Microdeformations of Wounds and Cell Proliferation", Plastic and Reconstructive Surgery, Oct. 2004, pp. 1097-1098.

Defranzo, A.J., et al., "109: Use of Sub-Atmospheric Pressure for Treatment of Gunshot Injuries", Plastic Surgical Forum, V. XXIII, Los Angeles, CA, Oct. 14-18, 2000, pp. 180-181.

Marks, M., et al., "Management of Complex Soft Tissue Defects in Pediatric Patients Using the V.A.C. Wound Closure", Plastic Surgical Forum, V. XXI, Boston, MA, Oct. 3-7, 1998, pp. 215-216.

Morykwas, M. and Argenta, L., "Use of Negative Pressure to Prevent Progression of Partial Thickness Burns", American Burn Association, V. 26, 26th Annual Meeting, Apr. 20-23, 1994, Orlando, Florida, pp. 157.

Morykwas, M. and Argenta, L., "Vacuum Assisted Closure (VAC Therapy) for Secondary Closure of Dehisced and Infected Wounds", Wound Repair and Regeneration, Jul.-Sep. 1995, pp. 361.

Morykwas, M. and Argenta, L., "Treatment of Burned Extremities Using Vacuum Therapy (The V.A.C.)", Wound Repair and Regeneration, V. 3, N. 3, Jul.-Sep. 1995, pp. 367.

Webb, L. and Morykwas, M., et al., "The Use of Vacuum-Assisted Closure in Composite Wound Management", The Third Riva Congress, Current Perspectives in Fracture Management and Orthopaedic Reconstruction, May 10-14, 2000, Italy, pp. 137.

Morykwas, M. and Webb, L., "Sub-Atmospheric Pressure for the Treatment of Lower Extremity Wounds", The Third Riva Congress, Current Perspectives in Fracture Management and Orthopaedic Reconstruction, May 10-14, 2000, Italy, pp. 135-136.

Argenta, L., et al., "Use of V.A.C. for Treatment of Dehisced Sternal Incisions", Plastic Surgical Forum, V. XXIII, Los Angeles, CA, Oct. 14-18, 2000, pp. 172-174.

Morykwas, M., et al., "Isolated Muscle Flap Survival with Complete Venous Occlusion: Varying Delay in External Application of Sub-atmospheric Pressure", Plastic Surgical Forum, V. XXI, Boston, MA, Oct. 3-7, 1998, pp. 237.

Morykwas, M. and Argenta, L., "V.A.C. Experience and Difficult Wounds", des Journees Regionales des Plaies et Cicatrisations, Sep. 22-23, 1997, pp. 76-90.

Morykwas, M. and Argenta, L., "Use of the V.A.C.™ for Treatment of a Traumatic Left Hip Disarticulation",ACA-Acta Chir. Austriaca, Supplement Nr. 150, 1998, pp. 24-25 and cover sheet.

Banwell, P., et al., "Application of Topical Sub-Atmospheric Pressure Modulates Inflammatory Cell Extravasation in Experimental Partial Thickness Burns", Wound Repair and Regeneration, Jul./Aug. 1999, V. 7, N. 4, pp. A286-A287.

Banwell, P., et al., "Dermal Perfusion in Experimental Partial Thickness Burns: The Effect of Topical Subatmospheric Pressure", Jan./Feb. 2000, V. 21, N. 1, Part 2, Burn Care & Rehabilitation.

Morykwas, M., et al., "The Effect of Externally Applied Subatmospheric Pressure on Serum Myoglobin Levels After a Prolonged Crused/Ischemia Injury", The Journal of Trauma Injury, Infection and Critical Care, Sep. 2002, V. 53, N. 3, pp. 537-540.

Molnar, J., et al., "Acceleration of Integra Incorporation in Complex Tissue Defects with Subatmospheric Pressure", Plastic and Reconstructive Surgery, Apr. 15, 2004, pp. 1339-1346.

(56) References Cited

OTHER PUBLICATIONS

DeFranzo, A.J., et al., "The Use of Vacuum-Assisted Closure Therapy for the Treatment of Lower-Extremity Wounds with Exposed Bone", Plastic and Reconstructive Surgery, Oct. 2001, V. 108, N. 5, pp. 1184-1191.
Morykwas, M., "The Use of The V.A.C. Wound Treatment System for Acute and Subacute Wounds", Plaies & Cicatrices, Would Closure Healing, Apr. 21, 22 and 23, 1999.
Webb, L., et al., "Negative Pressure Wound Therapy in the Management of Orthopedic Wounds", Ostomy Wound Management, Apr. 2004, V. 50, Issue 4A (Suppl), pp. 26-27 and cover sheet.
Webb, L., et al., "Wound Management With Vacuum Therapy", English abstract from website printout and German article, http://www.ncbi.nlm.nih.gov/entrez/query.fcgi?cmd=Retrieve &db=pubmed&dot=Abstra . . . , Dec. 2, 2004, 2 pages website printout, German article, Oct. 2001, pp. 918-926.
Webb, "New Techniques in Wound Management: Vacuum-Assisted Wound Closure", Journal of the American Academy of Orthopaedic Surgeons, V. 10, N. 5, Sep./Oct. 2002, pp. 303-311.
Morykwas, M. and Argenta, L., "Sub-Atmospheric Pressure Wound Treatment and Cultured Keratinocyte Allografts", Cultured Human Keratinocytes and Tissue Engineered Skin Substitutes, © 2001 Georg Thieme Verlag, pp. 343-346.
Molnar, J., et al., "Single-Stage Approach to Skin Grafting the Exposed Skull", Plastic and Reconstructive Surgery, Jan. 2000, V. 105, N. 1, 174-177.
Scherer, L, et al., "The Vacuum Assisted Closure Device: A Method of Securing Skin Grafts and Improving Graft Surival", Arch. Surg., V. 137, Aug. 2002, pp. 930-934.
Miller, P., et al., "Late Fascial Closure in Lieu of Ventral Hernia: The Next Step in Open Abdomen Management", the Journal of Trauma Injury, Infection and Critical Care, Nov. 2002, V. 53, N. 5, pp. 843-849.
Betancourt, S., "A Method of Collecting the Effluent From Complicated Fistula of the Small Intestine", 1986, p. 375.
Dorland's Illustrated Medical Dictionary , Twenty-Fifth Edition, 1974, pp. 1112.
Hopf, H., et al., "Adjuncts to preparing wounds for closure Hyperbaric oxygen, growth factors, skin substitutes, negative pressure wound therapy (vacuum-assisted closure)", Foot Ankle Clin N Am 6, 2001, pp. 661-682.
Chariker-Jeter® Wound Drainage Kit, BlueSky Medical, 2 page advertisement with business card from Quality Medical Supply.
Chariker-Jeter® Wound Drainage Kit Instructions, Item #500.7777, BlueSky Medical, 2 pages.
Wooding-Scott® Wound Drainage Kit Contents, Item #500.8888, 1 page.
Montgomery, B., "Easy Dressing of Large, Draining Abdominal Wounds Using Moisture Vapor-Permeable Film", pp. 417-418, Techniques for Surgeons, Wiley Medical Publication, © 1985.
Herrmann, L., et al., "The Pavaex (Passive Vascular Exercise) Treatment of Obliterative Arterial Diseases of the Extremeties", The Journal of Medicine, Dec. 1933, pp. 524-529.
Herrmann, L., et al., "Passive Vascular Exercises: Treatment of Peripheral Obliterative Arterial Diseases by Rhythmic Alternation of Environmental Pressure", Archives of Surgery, v. 29, n. 5, Nov. 1934, pp. 697-704.
Sturr, R., Evaluation of Treatment of Peripheral Vascular Disease by Alternating Positive and Negative Pressure, Philadelphia, Archives of Physical Therapy, Sep. 1938, pp. 539-543.
Balin, A., et al., "Oxygen Modulates Growth of Human Cells at Physiologic Partial Pressures", Laboratory for Investigative Dermatology, J. Exp. Med. ©, the Rockefeller University Press, v. 160, Jul. 1984, pp. 152-166.
Saran Resins and Films, "Fresh Thinking". website printout, 6 pages, Jan. 20, 2004.
Bluesky Medical, "A Leader in Suction Technology—Wound Drainage Experts", printout of website, 55 pages, Apr. 8, 2003, www.blueskymedical.com.
Davydov, et al., "Would Healing Under the Conditions of Vacuum Draining", Khirurgiia (Mosk). 1992, (7-8): 21-6 (with English translation by Scientific Translation Services).
Coyle, M., et al., "A Case Study: Positive Outcomes to Negative Pressure Wound Therapy—A collaborative assessment", Hospital of Saint Raphael, 1 page chart.
Nemoto, H., et al., "Stories From the Bedside: Purple Urine Bage Syndrome Development in Ileal Conduit", WCET, Journal 23(2), pp. 31-34.
Baker, B., "Negative-Pressure Therapy Looks Promising", Skin & Allergy News, Feb. 2000, p. 14.
McCallon, S., et al., "Vacuum-Assisted Closure versus Saline-Moistened Gauze in the Healing of Postoperative Diabetic Foot Wounds", Ostomy Wound Management, Aug. 2000, v.46, Issue 8.pp. 28-29, 31-32, 34.
PCT/US08/79364—International Report on Patentability P04263WO0-IPRP (Apr. 13, 2010).
PCT/US03/16763—Written Opinion, International Preliminary Examination Report, and International Search Report, P02915WO0-ISR (Dec. 18, 2003, Apr. 19, 2004, and Sep. 2, 2004).
PCT/US08/30581—International Report on Patentability P04486WO0-IPRP (Jul. 22, 2010).
PCT/US09/50806—Written Opinion and International Search Report P04165WO0-ISR_WO (Sep. 15, 2009).
PCT/US09/50806—International Report on Patentability P04165WO0-IPRP (Jan. 27, 2011).
Murray, J., et al., "On the Local and General Influence on the Body if Increased and Diminished Atmospheric Pressure", The Lancet, V. 1, 1834-1835, pp. 909-917.
Herrmann, L., et al., "The Conservative Treatment of Arteriosclerotic Peripheral Vascular Diseases", pp. 750-760 (Oct. 1934).
Versatile 1 Wound Vacuum System™ for the Promotion of Wound Healing, Wound Application instructions, 1 page advertisement.
Bluesky Medical "The Versatile One!™", Wound Drainage and More, 1 page advertisement. (Labeled Spring 2003).
Chariker-Jeter® Wound Sealing Kit, Would Application Instructions, 1 page advertisement.
Thomas, S., et al., "Comparative Review of the Properties of Six Semipermeable Film Dressings", The Pharmaceutical Journal, Jun. 18, 1988, pp. 785-789.
Baker, B., "Abundance of Web Sites on Wound Care Management", Family Practice News, Mar. 1, 2000, pp. 52.
Cosker, T., et al., "Choice of Dressing Has a Major Impact on Blistering and Healing Outcomes in Orthopaedic Patients", Journal of Wound Care, Vo. 14, No. 1, Jan. 2005, pp. 27-29.
Townsend, P.L.G., "The Quest for a Cheap and Painless Donor-Site Dressing", Burns, 2, pp. 82-85 (Jan. 1976).
Langworthy, M., et al., "Treatment of the Mangled Lower Extremity After a Terrorist Blast Injury", Clinical Orthopaedics and Related Research, No. 422, pp. 88-96 (May 2004).
Park, G.B., et al., "The Design and Evaluation of a Burn Wound Covering", Supplied by The British Library—"The Word's Knowledge", pp. 11-15 (1978).
ACU-derm® Transparent Moisture Vapor Permeable Polyurethane Dressing, pp. 1-13 and cover sheet.
3M Ioban 2, Breathability, Conformability and Strength, Breathability—Moisture Vapor Transmission Rate and Conformability and Strength—Tensile Strength, Elongation and Fn Modulus Test (1 page).
Smith&nephew website printout, Would Management, FAQs.
M. Gosta Arturson, *The Pathophysiology of Severe Thermal Injury*, JBCR, 6(2):129-146 (Mar.-Apr.) 1985.
R. A.F. Clark et al., The Molecular and Cellular Biology of Wound Repair, Chapter 1 (1988).
Jeter, K.F. et al. (eds.), "Managing Draining Wounds and Fistulae: New and Established Methods," Chronic Wound Care: Health Management Publications, 1990, pp. 240-246.
Aeros, "Moblvac II."
Aeros, Aeros Instruments, Inc. 1111 Lakeside Drive, Gurnee, IL 60031. Aug. 1993. "Care-E-Vac."
Emerson, Series 55. J. H. Emerson Co., 22 Cottage Park Ave., Cambridge, MA 02140. "Emerson Post-Operative Suction Pumps."

(56) References Cited

OTHER PUBLICATIONS

Emerson, J. H. Emerson Co., (address: same as above). "Emerson Transport Suction Unit."
Aeros, Aeros Instruments, Inc. 3411 Commercial Ave., Northbrook, IL 60062. Oct. 1988. Part No. 1504-02 7M. "Instavac Aspirator."
"Pleur-evac. Adult-Pediatric, Non-Metered." Code No. A-4000. Control No. F7961J.
Instruction Manual, Creative Medical Laboratories, Inc. P.O. Box 6347, Rochester, Minn. 55903. "TUGS" (Transportable Universal Gradient Suction).
Deknatel, Div. of Howmedica, Inc. Quenns Village, NY 11429. "Pleur-evac."
Sparta Instrument Corp. 26602 Corporate Ave., Hayward, CA 94545. "Power Source Multi-Purpose Surgical Aspirator."
Wells Johnson Company, 2045 N. Forbes Blvd., Suite 106, Tucson, AZ. "Point 5 Aspirator."
Microtek Heritage, Inc. P.O. Box 2487, Columbus, MS 39704. "Wound-Evac ET."
Fleischmann, W. *Wund Forum Spezial.* IHW '94. "Vakuumversiegelung zur Behandlung von Probelmwunden" (with English translation: "Vacuum sealing for Treatment of Problematical Wounds."
Fleischmann, W. *Acta Orthopaedica Belgica.* vol. 58, Suppl. I-1992 "Treatment of Bone and Soft Tissue Defects in Infected Nonunion."
Fleischmann, W. Strecker W, Bombelli M, Kinzl L. *Unfall Chirurg.* Springer-Variag 1993. 96:488-92 "Vakuumversiegelung zur Behandlung des Weichteilschadens bei offenen Frakturen." with English translation [Vacuum sealing as treatment of soft tissue damage in open fractures]. [German].
Valenta, A.L. *American Journal of Nursing.* Apr. 1994. "Using the Vacuum Dressing Alternative for Difficult Wounds." 94:44-5.
Bier, A., "Hyperemia by Suction Apparatus" Chapter VIII, Hyperemia as a Therapeutic Agent, Chicago, IL, Roberts Publishing, 74-85, (1905).
Saunders, J. W., The Lancet, pp. 1286-1287, Jun. 28, 1952, "Negative-Pressure Device for Controlled Hypotension during Surgical Operations".
Landis, et al., Robinette Foundation of the Hospital of the University of Pennsylvania, "The Effects of Alternate Suction and Pressure on Blood Flow to the Lower Extremities" (Sep. 1933).
Hargens et al., Space Physiology Laboratory, Life Science Division, NASA Ames Research Center, "Control of Circulatory Function in Altered Gravitational Fields" (Feb. 1992).
Wolthuis et al, Physiological Reviews, 54: 566-595, Jul. 1974, "Physiological Effects of Locally Applied Reduced Pressure in Man".
Viljanto et al., Br. J. Surg., 63: 427-430, 1976, "Local Hyperalimentation of Open Wounds".
Dillon, R. Angiology—The Journal of Vascular Diseases, pp. 47-56, Jan. 1986, "Treatment of Resistant Venous Stasis Ulcers and Dermatitis with the End-Diastolic Pneumatic Compression Boot".
Lundvall et al., Acta Physiol Scand, 136: 403-409, accepted Jan. 28, 1989, "Transmission of externally applied negative pressure to the underlying tissue. A study on the upper arm of man".
Klemp et al., The Journal of Investigative Dermatology, pp. 725-726 (1989), "Subcutaneous Blood Flow in Early Male Pattern Baldness".
A. Harle, Z. Orthop., 127: 513-517 (1989), "Schwachstellen herkommlicher Drainagen" with English Translation.
Dunlop et al., Br. J. Surg., 77: 562-563 (1990), "Vacuum drainage of groin wounds after vascular surgery: a controlled trail".
Maddin et al., International Journal of Dermatology, 29: 446-450 (1990), "The Biological Effects of a Pulsed Electrostatic Field with Specific Reference to Hair: Electrotrichogenesis".
Nakayama et al., Ann. Plast. Surg., 26:499-502 (1991), "A New Dressing Method for Free Skin Grafting in Hands".
Hargens et al., Aviation, Space and Environmental Medicine, pp. 934-937, Oct. 1991, "Lower Body Negative Pressure to Provide Load Bearing in Space".
Author unknown, Science, Sep. 1992, p. 42, "The Not-So-Bald-Truth".
Techno Takatsuki Co., Ltd., 8-16 Hatchonishimachi, Takatsuki City, Osaka, Japan, "HiBlow Air Pump".
Wells Johnson Company, 2045 N. Forbe Blvd., Suite 106, Tucson, AZ, "Suction Tips".
Industrial Equipment News, P.O. Box 1158, Skokie, IL 60076-9786, "Miscellaneous Equipment".
Letsou et al. "Stimulation of Adenylate Cyclase Activity in Cultured Endothelial Cells Subjected to Cyclic Stretch." Cardiovascular Surgery 3. Toronto. Sep. 1989. 634-639.
Bucalo et al. "Inhibition of Cell Proliferation by Chronic wound Fluid." Wound Repair and Regeneration. 181-186 Jul. 1993.
Falanga, Vincent. "Growth Factors and Chronic Wounds: The need to Understand the Microenvironment." Journal of Dermatology, Bol. 19: 667-672. 1992.
Urschel et al. "The Effect of Mechanical Stress on Soft and Hard Tissue Repair; a Review." British Journal of Plastic Surgery. 41, 182-186. 1988.
Gogia, Prem P. "The Biology of Wound Healing." Ostomy/Wound Management. Nov.-Dec. 1992. pp. 12, 14-16, 18-20, 22.
Wysocki et al. "Wound Fluid from Chronic Leg Ulcers Contains Elevated Levels of Metalloproteinases MMP-2 and MMP-9." The Society for Investigative Dermatology, Inc. Jul. 1993. 64-68.
Olenius et al. "Mitotic Activity in Expanded Human Skin." Plastic and Reconstructive Surgery. Feb. 1993. 213-216.
Mulder, G. D. et al. (eds.), *Clinicians' Pocket Guide to Chronic Wound Repair*, (Spartanburg, SC: Wound Healing Publications), 1991, pp. 54-55.
Chariker, M. E. et al. (eds), "Effective Management of Incisional and Cutaneous Fistulae with Closed Suction Wound Drainage," Contemporary Surgery, vol. 34, Jun. 1989, pp. 59-63.
Rastgeldi, S.: I. Pressure Treatment of Peripheral Vascular Diseases. II. Intermittent Pressure Treatment of Peripheral Vascular Diseases. Opuscula Medica, Suppl. XXVII, 1972.
OP-Journal Nr. 3, Jahr. Dec. 6, 1990, pp. 31-35 W. Fleischmann, M. Mentzel, L. Kinzl "BWS, Gefahren und Komplikationen der Therapie" with English Trans.
Zumtobel et al., (1991) "Wunddrainage in der Elektiveund Notfallchirurgie" Wolfgang Pabst Verlag, relevant p. 12, left column. English Translation attached.
Saechtling, Kunststoff-Taschenbuch, 24. Ausgabe 1989, S. 439, 477. English Translation attached.
Mutschler, W. Bakker D. J., "Temporarer Hautersatz", ZFA 1989, Heft 24, S. 714-720 als Sonderdruck. English Translation attached.
W. Fleischmann, U. Becker, M. Bischoff, H. Hoekstra, "Vacuum sealing: indication, technique, and results", Eur. J. Orthop & Traumato (1995) 5:37-40.
Argenta LC, Morykwas MJ. Vacuum-assisted closure: a new method for wound control and treatment: clinical experience. Ann Plast Surg 1997;38: 563-577.
Morykwas MJ, Argenta LC, Shelton-Brown EI, McGuirt W. Vacuum-assisted closure: a new method for wound control and treatment: animal studies and basic foundation. Ann Plast Surg 1997; 38:553-62.
Davydov IA, Larichev AB, Smirnov AP, Flegontov VB. Vakuum-terapiia v lechenii ostrykh gnoinykh zabolevanii miagkikh tkanei I gnoinykh ran. [Vacuum therapy of acute suppurative diseases of soft tissues and suppurative wounds]. Russian Vestnik Khirurgii Imeni I—I—Grekova 1988; 141: 43-6 with Eng.Trans.
Davydov IA, Abramov AI, Larichev AB. Vakuum-terapiia v preduprezhdenii posleoperatsionnoi ranevoi infektsii. [Vacuum therapy in the prevention of postoperative wound infection]. Russian Vestnik Khirurgii Imen I—I—Grekova 1991; 147:91-5, with English Translation.
Iankov NI. Simuliatsiia konsolidatsii perelomov nizhnei cheliusti vaktuumnoi terapiei. [Stimulation of consolidation of mandibular fractures by means of vacuum therapy] Russian. Stomatologiia 1971; 50: 86, with Eng. Trans.
Inoiatov IM, Aleksandrov VB. Lechenie promezhnostnoi rany posle amputatsii priamoi kishki vakuum-aspiratsiei. [Vacuum aspiration in the treatment of the perineal wound following extirpation of the rectum]. Russian. Khirurgiia 1971; 47: 74-8, with English Translation.

(56) References Cited

OTHER PUBLICATIONS

Kochnev VA. Primenenie vakuum-drenazhnoi sistemy dlia profilaktiki posleoperatsionnykh ranevykh oslozhnenii u bol'nykh opukholiami. [The use of a vacuum drainage system in the prevention of postoperative wound complications in tumor patients]. Russian. Voprosy Onkologii 1967; 13:102-5, w/Eng. Trans.

Mirazimov BM. Svobodnaia Kozhnaie plastika stopy s podgotovkoi ranevoi poverkhnosti vakumiravaniem [Free skin graft of the foot with vacuum preparation of the wound surface]. Russian. Orthopediia Travmatologiia I Protezirovanie 1966;27:19-22, with English Translation.

Mirazimov BM, Vasina TA, Mezhericher MI. Mikroflora dlitel'no nekazhivaiushchikh ran i effektivnost' metoda vakuumirovaniia. [Microflora of prolonged non-healing wounds and the effectiveness of the vacuum evaporative method]. Russian. Khirurgiia 1967; 43: 40-3, with English Translation.

Mirazimov BM. Vorbereitung von Wunden und Geschwuren zur Hautplastik unter Anwendung der Vakuumierung [Preparation of wounds and abcesses for dermatoplasty by means of a vacuum device]. German. Beitrage zur Orthopadie und Traumatologie 1967; 14:224-30, with Eng. Translation.

Netudykhatka O. Vliianie nizkogo dozirovannogo vakuuma na techenie reparativnogo protsessa v kostnoi tkani [Effect of low vacuum on the course of the reparative process in bone tissue]. Russian. Voprosy Kurortologii, Fizioterapii i Lechebnoi Fizicheskoi Kultury 1972; 37:411-5, w/Eng. Trans.

Volkov LA. Ispol'zovanie vakuum-drenazhnoi sistemy v khirurgicheskoi praktike. [Use of vacuum-drainage system in surgical practice]. Russian. Klinicheskaia Khirurgiia. 1973;7:54-5, with English Translation.

Teder H, Sanden G, Svedman P. Continuous Wound Irrigation in the Pig. J Invest Surg 1990;3:399-407.

Nakayama Y, Tomotari I, Soeda S. A New Method for the Dressing of Free Skin Grafts. Plast Reconstr Surg 1990;86:1216-1219.

Brock WB, Barker DE, Burns RP. Temporary Closure of open abdominal wounds: the vacuum pack. Amer Surg 1995;61:30-5.

Shein M, Saadia R, Jameson JR, Decker GAG. The "sandwich technique" in the Management of the Open Abdomen. Br J Surg 1986;73:369-70.

Broome A. Hansson L, Lundgren F, Smedberg S. Open Treatment of Abdominal Septic Catastrophies. World J. Surg 1983;7:792-6.

Vatanasapt V, Areemit S, Jeeravipoolvarn P, et al. Red rubber bulb, cheap and effective vacuum drainage. Journal of the Medical Association of Thailand 1989;72:193-7.

Brummelkamp WH, Taat CW, Slors JF. High-vacuum drainage and primary perineal wound closure in abdominoperineal excision of the rectum. Netherlands Journal of Surgery 1991;43:236-9.

Morykwas J, Argenta LC. Nonsurgical modalities to enhance healing and care of soft tissue wounds. Journal of the Southern Orthopaedic Association 1997;6:279-88.

Sames CP. Sealing of wounds with vacuum drainage [letter] Br Med J 1977;2:1123.

Greer SE, Longaker MT, Margiotta M. Preliminary Results from a Multicenter, Randomized, Controlled, Study of the Use of Subatmospheric Pressure Dressing for Pressure Ulcer Healing. Wound Repair and Regeneration 1999;7:255.

Greer SE, Longaker MT, Margiotta M, Matthews AJ, Kasabian A. The Use of Subatmospheric Pressure Dressing for the Coverage of Radial Forearm Free Flap Donor-Site Exposed Tendon Complications. Ann Plast Surg 1999;43:551-554.

Greer SE, Duthie E, Cartolano B, Koehler KM, Maydick-Youngberg D, Longaker MT. Techniques for Applying Subatmospheric Pressure Dressing to Wounds in Difficult Regions of Anatomy. JWOCN 1999;26:250-3.

Greer SE, Kasabian A, Thorne C, Borud L, Sims CD, Hsu M. The Use of Subatmospheric Pressure Dressing to Salvage a Gustilo Grade IIIB Open Tibia Fracture with Concomitant Osteomyelitis and Avert a Free Flap. Ann Plast Surg 1998;41:687.

Genecov DG, Schneider AM, Morykwas MJ, et al. A Controlled subatmospheric pressure dressing increases the rate of skin graft donor site reepithelialization. Ann Plast Surg 1998;40:219-25.

Mendez-Eastman S. Negative pressure wound therapy. Plastic Surgical Nursing 1998;18:27-9, 33-37.

Banwell P. Withey S, Holten I. The use of negative pressure to promote healing [letter; comment]. Brit J Plast Surg 1998;51:79.

Blackburn J H Boemi L, Hall WW. et al. Negative-pressure dressings as a bolster for skin grafts. Ann Plast Surg 1998;40:453-7.

Smith LA, Barker DE, Chase CW, et al. Vacuum Pack Technique of Temporary Abdominal Closure: A Four-Year Experience. Amer Surg 1997;63:1102-8.

McCulloch JM, Kemper CC. Vacuum-Compression Therapy for the Treatment of an Ischemic Ulcer. Physical Therapy 1993;73:165-9.

Mullner T, Mrkonjic L, Kwasny O, Vecsei V. The use of negative pressure to promote the healing of tissue defects: a clinical trial using the vacuum sealing technique [see comments]. Brit J Plast Surg 1997;50:194-9.

Mirazimov, B.M.: Free Skin Grafting of Wounds and Ulcers using the "Vacuum Treatment" Method. [Orthop. Travmatol. Protez., 28(1):54-58.] with English Trans. 1967.

Greer, Steven E., "Whither Subatmospheric Pressure Dressing?" The Institute of Reconstructive Plastic Surgery, The New York University Medical Center, New York, NY April Issue of Annals of Plastic Surgery 2000.

Registration No. 1982349. Owner, KCI Inc., 3440 E. Houston Street San Antonio Texas 78219. Source: United States Patent and Trademark Office official website. Filing date May 1, 1995 Registration Date Jun. 25, 1996.

Hidden Interest—A Special Report.; When Physicians Double as Entrepreneurs. The New York Times. 11pp. Nov. 30, 1999.

Defranzo, Anthony J., et al., "Vacuum-Assisted Closure for the Treatment of Degloving Injuries." Plastic and Reconstructive Surgery 104 (7) 2145-48: (1999).

Morykwas, Michael J., et al., "Use of Subatmospheric Pressure to Prevent Progression of Partial-Thickness Burns in a Swine Model". Journal of Burn Care & Rehabilitation 20 (1 Part 1): 15-21 (1999).

Morykwas, Michael J., et al., "Use of Subatmospheric Pressure to Prevent Doxorubicin Extravasation Ulcers in a Swine Model". Journal of Surgical Oncology 72:14-17 (1999).

Schneider, Andrew M., et al., "A New and Reliable Method of Securing Skin Grafts to the Difficult Recipient Bed". Plastic and Reconstructive Surgery 102(4) 1195-98 (1998).

Rosser, Charles J., et al., "A New Technique to Manage Perineal Wounds". Infections in Urology 13(2) 45-47, 56 (2000).

Philbeck, Thomas E., et al., "The Clinical and Cost Effectiveness of Externally Applied Negative Pressure Wound Therapy in the Treatment of Wounds in Home Healthcare Medicare Patients". Ostomy/Wound Management 45(11) 41-44, 46-50 (1999).

Meara, John G., et al., "Vacuum-Assisted Closure in the Treatment of Degloving Injuries". Annals of Plastic Surgery 42(6) 589-594 (1999).

Obdeijn, Miryam C., et al., "Vacuum-Assisted Closure in the Treatment of Poststernotomy Mediastinitis". Ann Thorac Surgery 68 2358-60 (1999).

Mendez-Eastman, Susan., "When wounds won't heal". RN 20-24 (1998).

Hartnett, Jacqueline M., "Use of Vacuum-Assisted Wound Closure in Three Chronic Wounds". JWOCN 25 (6) 281-290 (1998).

Mendez-Eastman, Susan., "Use of Hyperbaric Oxygen and Negative Pressure Therapy in the Multidisciplinary Care of a Patient with Nonhealing Wounds". JWOCN 26(2) 67-76 (1999).

Wooding-Scott, Margaret et al., "No-Wound is Too Big for Resourceful Nurses". RN, Dec. 1988, 22-25.

Davydov, et al., "Pathenogenic mechanism of the effect of vacuum therapy on the course of the wound process". Khirurgiia, Jun. 1990 (with English translation).

Davydov, et al., "Vacuum therapy in the treatment of suppurative lactation mastitis". Vestn. Khir., Nov. 1986 (with English translation).

Davydov, et al., "Bacteriological and cytological evaluation of the vacuum therapy of suppurative wounds". Vestn. Khir., Oct. 1988 (with English translation).

(56) References Cited

OTHER PUBLICATIONS

Davydov, et al., "Basis of the use of forced early secondary suture in the treatment of suppurative wounds by the vacuum therapy method". Vestn. Khir., Mar. 1990 (with English translation).
Borzov, et al., "Vacuum therapy of some skin diseases". Vestn. Dermatol. Venerol., Aug. 1965 (with English translation).
M.J. Morykwas and L.C. Argenta, "Techniques in Use of V.A.C. Treatment (in English)", Acta Chir. Austriaca Supplement Nr. 150, 1998, p. 3-4 of 2-28.
Garcia-Rinaldi, et al., "Improving the Efficiency of Wound Drainage Catheters", J. Surg., 1975, pp. 372-373.
Raffl, et al. "The Five Year Survival Rate for Gastric Cancer: Statistical Study from Syracuse Medical Center", Cancer, 6:756-759, Jul. 1953.
Raffi, et al., The Use of Negative Pressure Under Skin Flaps After Radical Mastectomy, Ann. Surg. 136: 1048, Dec. 1952.
Marie Knight, "A Second Skin for Patients with Large Drainage Wounds," Nursing 6(1) p. 37, 1976.
Oscar Ramirez, "Optimal Wound Healing under Op-Site Dressing" Plas. & Recon. Surg., 73(3): 474-475; 1984.
Helen Bibleheiner, "Dealing with a Wound that Drains 1.5 Liters per Day," RN Aug. 1986.
Peter Schwab, "Primary Closure of the Perineal Wound After Proctectomy" Mayo Clin. Proc., Mar. 1974, vol. 49.
International Search Report dated Feb. 20, 2009 in corresponding PCT/US2009/30581 application.
Written Opinion dated Feb. 20, 2009 in corresponding PCT/US2009/30581.
Proto, Massachusetts General Hospital Dispaches from the Frontiers of Medicine, 2 sheets, (Winter 2006).
Powell, E.T., "The role of negative pressure wound therapy with reticulated open cell foam in the treatment of war wounds," J. Orthop. Trauma, vol. 22(10) Supp.: S138-S141, (Nov./Dec. 2008).
"Negative pressure wound therapy devices," Technology assessment report; Agency for Healthcare Research and Quality, with annotations, website dated May 26, 2009, printed Jun. 26, 2009 and Jun. 28, 2009.
Thomas, S., "Atraumatic dressings," World Wide Wounds, sponsored by Molnylcke Health Care, 11 sheets, published Jan. 2003, website printout dated Jun. 29, 2009.
Orgill, D.P., et al., "The mechanisms of action of vacuum assisted closure: More to learn," Surgery, 146(1):40-51, (Jul. 2009).
Defranzo, A., et al., "4: Vacuum-assisted closure in extremity trauma," in Soft Tissue Surgery, S.L. Moran et al., p. 49-60 and additional sheet, Lippincott Williams & Wilkins (Pub. Apr. 1, 2008).
Stoeckel, W.T., et al., "30: Vacuum assisted devices for difficult wounds of the face and neck," Essential Tissue Healing of the Face and Neck, p. 399-408, and additional sheet, Hom, et al., (Pub. Jan. 28, 2009).
Marks, M.W., et al., "Principles & Applications of Vacuum Assisted Closure (VAC)" Plastic Surgery Secrets, 2nd ed., Mosby Elsevier, (2010).
Bonnamy, C., et al., "Use of the vacuum-assisted closure system for the treatment of perineal gangrene involving the abdominal wall", Ann. Chir., (English abstract on first page and 1 sheet PubMed abstract) 125(10):982-4 (Dec. 2000).
Wong, S.L., et al., "Loxoscelism and negative pressure wound therapy (Vacuum-assisted closure): a clinical case series," Am. Surg., 75:1128-1131, (Nov. 2009).
Covey, D.C. et al., "Orthopaedic war injuries: From combat casulty care to definitive treatment: A current review of clinical advances, basic science, and research opportunities," Instr. Course Lect. 57:65-86 (2008).
Pirela-Cruz, M.A., et al., "Management of large soft-tissue wounds with negative pressure therapy—lessons learned from the war zone," J. Hand Ther. 21:196-203, (2008).
Vertrees, A., et al., "Modern management of complex open abdominal wounds of war: A 5-year experience," J. Am. Coll. Surg., 207:801-809, (2008).
Geiger, S., et al., "War wounds: Lessons learned from Operation Iraqi Freedom," Plast. Reconstr. Surg., 122:146-153, (2008).
Hospenthal, D.R., et al., "Guidelines for the prevention of infection after combat-related injuries," J. Trauma, 64(3): S211-S220, (2008).
Murray, C.K., et al., "Prevention and management of infections associated with combat-related extremity injuries," J. Trauma, 64(3):S239-S251, (2008).
Campbell, P.E., et al., "Retrospective clinical evaluation of gauze-based negative pressure wound therapy," Int. Wound J., 5(2):280-286, (2008).
PCT/US08/50584—Written Opinion and International Search Report P04164WO0-ISR (Jul. 25, 2008).
Argenta, A., et al., "Deformation of superficial and deep abdominal tissues with application of a controlled vacuum", European Tissue Repair Society, Focus group meeting Topical Negative Pressure (TNP) Therapy, London UK ( Dec. 4-6, 2003).
Vacuum Assisted Closure (V.A.C.(R)) Therapy: an overview of scientific, clinical, and cost effectiveness evidence, (19 sheets) KCI Licensing, Inc., 2009.
Merriam-Webster Online, "reepithelialization," printout of webpage dated Apr. 17, 2009.
Oxford English Dictionary Online, "deformable," "deform," and "flexible," printout of webpages dated Apr. 17, 2009.
Murphey, G.C., et al., "Depth of penetration of negative pressure wound therapy into underlying tissues," Wound Repair and Regeneration, 17:113-117 (2009).
Jargin, S.V., "Limited access to foreign medical literature in Russia," Chartered Institute of Library and Information Professionals Health Libraries Group Newsletter, 25(4):7-10, (Dec. 2008).
Website printout "Chemical of the week" polymers, 5 sheets, printout dated Apr. 17, 2009.
Chariker, M.E., et al., "An algorithmic approach to the use of gauze-based negative-pressure wound therapy as a bridge to closure in pediatric extremity trauma," Plast. Reconstr. Surg., 123:1510-1520, (2009).
Cornelius, M., "Care in the air: Bringing the wounded closer to home," Plast. Surg. Nurs., 29(3):165-168, (Jul.-Sep. 2009).
Kumar, A.R., et al., "Lessons from Operation Iraqi Freedom: Successful subacute reconstruction of complex lower extremity battle injuries," Plast. Reconstr. Surg., 123:218-229, (2009).
Morykwas, M.J., "Use of sub-atmospheric pressure to prevent adriamycin extravasation ulcers in a pig model", first presented at the 44th Annual Meeting of Plastic Surgery Research Council, Pittsburg, PA, (May 22-26, 1999).
"The Remington Report: Business and clinical strategies for home care executives", containing articles by J.A. Molnar, D.G. Armstrong, et al., and S. Mendez-Eastman; (Nov./Dec. 2004).
Molnar, J.A., "V.A.C. and burn care", presentation.
Slides regarding use of V.A.C.
Egnell Minor, Instruction Book, First Edition allegedly dated Feb. 1987, 34 pages of English translation.
Addition to the "Users Manual Concerning Overflow Protection—Concerns all Egnell Pumps", dated Feb. 3, 1983, 2 pages of English translation.
Ulaschik, V.S., "Barotherapy", in Physical Therapy, Universal Medical Encyclopedia; pp. 85-86 and cover sheet (3 sheets in English, 3 sheets in Russian), (2008, allegedly gone to print Oct. 1, 2007).
Opposition to EP 2 392 302—Communication of Opponent Hartmann dated Nov. 12, 2013 and European Patent Office's Communication of a notice of opposition (and translation) dated Nov. 19, 2013.
Opposition to EP 2 392 302—Communication of Opponent KSNH dated Nov. 12, 2013 and European Patent Office's Communication of a notice of opposition dated Nov. 18, 2013.
Lindstedt, S., et al., "A compare between myocardial topical negative pressure levels of -25 mmHg and -50 mmHg in a porcine model", BMC Cardiovascular Disorders 2008 8:14, BioMed Central, pp. 1-7.
Lindstedt, S., et al., "Blood Flow Changes in Normal and Ischemic Myocardium During Topically Applied Negative Pressure", Ann Thorac Surgery 2007;84:568-73.

\* cited by examiner

DEVICE AND METHOD FOR TREATING CENTRAL NERVOUS SYSTEM PATHOLOGY

RELATED APPLICATIONS

This application is a continuation of U.S. application Ser. No. 12/351,331, filed Jan. 9, 2009, now U.S. Pat. No. 8,267,960, which claims the benefit of priority of U.S. Provisional Application 61/019,968, filed on Jan. 9, 2008, and U.S. Provisional Application No. 61/081,997, filed on Jul. 18, 2008, the entire contents of which are incorporated herein by reference.

FIELD OF THE INVENTION

The present invention relates generally to a device and method for treating tissues of the central nervous system using sub-atmospheric pressure and more particularly, but not exclusively, to a device and method for treating the brain tissue using sub-atmospheric pressure.

BACKGROUND OF THE INVENTION

The anatomy, physiology, and pathologic processes that involve the central nervous system (CNS) make CNS tissue unique. The preservation of both the three-dimensional structural anatomy and the microanatomical relationships of neurons (whose function depends specifically on spatial relationships with other neurons and other supporting cells), as well as the maintenance of properly oxygenated blood flow and the homogeneous ground substance matrix in which the neurons survive, are vital to the survival and function of the central nervous system tissues. Moreover, the inability of central nervous system cells to regenerate emphasizes the need to maximize survival of every possible neuron. For reasons such as these, treatment of both open and closed space pathology in the central nervous system is unique.

Among the clinical problems that threaten survival of CNS tissues, the control of central nervous system edema, infection, and blood supply are central. The brain responds to trauma and injury by collecting a significant amount of interstitial edema. Because the brain is enclosed in a closed space (the dura and skull), edema results in compression and compromise of the blood flood and nutritional performance of the CNS, which greatly impairs physiological recovery of the central nervous system and often of itself results in progression of compromise and death of the CNS parenchyma. Currently available treatments for reducing edema include agents to decrease vascular permeability (glucocorticoids: Dexamethasone, Prednisone, Methyl Prednisolone), diuretics, mechanical ventricular drainage, resection of the brain parenchyma, and extensive craniectomy. However, disadvantages to these treatments include poor results, complications from the drugs, and inconsistent results.

The need for rapid and effective treatment is also vital due to the disastrous consequences and high likelihood of rapid propagation of infection and edema in the CNS. At present there are few successful methods available to treat pathologies affecting the intracranial and intraspinal space, CNS parenchyma, and the surrounding structures. Where elsewhere tissues can be treated with dressing changes, the CNS is not amenable to this type of treatment because of its inaccessibility, precarious structure, propensity for infection, and progression of injury. There is evidence that inflammation and immunological response to central nervous system trauma and other pathology are of equal or greater long term consequences than the initial trauma or insult. The response of the CNS to decreased blood flow secondary to edema results in hypoxia and ischemia/reperfusion-mediated injury. These injuries contribute to the neuropathological sequella, which greatly contribute to the adverse outcome of head injury.

In addition, the brain requires a continuous supply of oxygenated blood to function and survive. Within three minutes of complete interruption of blood flow to the brain, irreversible brain damage results, though the brain can however remain viable and recover from reduced blood flow for more prolonged periods. There is evidence that focal areas of the brain can remain ischemic and relatively functionless for days and still recover. This finding has led to the concept of an ischemic zone, termed the penumbra or halo zone, that surrounds an area of irreversible injury. A secondary phenomena is the release of excitotoxins that are released locally by injured neurons, alterations in focal blood flow, and edema.

Cerebrovascular disease may be a result of: inadequate blood flow to the brain cells from decreased perfusion pressure, rupture of a blood vessel resulting in direct injury to the local brain area and by compression of adjacent tissue. Intrinsic disease of the brain blood vessels such as atherosclerosis, aneurysm, inflammation, etc. or a remote thrombus that lodges in the brain blood vessels from elsewhere such as the heart can produce cerebrovascular disease. A stroke is a term that defines a neurological injury that occurs as a result of some of these pathologic processes. Five percent of the population over 65 are affected by cerebrovascular diseases which are the third leading cause of death in the developed world. In addition, lifelong debility, inability to work and function in society and the family, and the frequent need for nursing home treatment often result. People affected by strokes usually have significant impairments for the rest of their lives.

A stroke in evolution, or progressive stroke, refers to a neurological deficit that progresses or fluctuates after the initial event. It is thought that this occurs because of progressive spasm or narrowing of the involved artery, development of cerebral edema around the initial injury, thrombus propagation as a result of decreased blood flow or release of local cytokines from injured brain cells. Fortunately there are some communications between vessels in the brain called collateral circulation. Supplying blood from these collateral vessels may prevent death of brain cells in the ischemic zone.

In cases of intracranial hemorrhage, the hemorrhage usually begins as a small mass that grows in volume by pressure dissection and results in displacement and compression of adjacent brain tissue. Edema in the adjacent compressed tissue around the hemorrhage may lead to a mass effect and a worsening of the clinical condition by damaging a larger area of brain tissue. Edema in the adjacent brain may cause progressive deterioration usually seen over 12 to 72 hours. The occurrence of edema in the week following the intracerebral hemorrhage often worsens the prognosis, particularly in the elderly. The tissue surrounding the hematoma is displaced and compressed but is not necessarily fatally compromised. Improvement can result as the hematoma is resorbed and the involved tissue regains function.

Treatment of these conditions has been disappointing. Surgical decompression of hemorrhage can be helpful in some cases to prevent irreversible compression. Agents such as mannitol and some other osmotic agents can reduce intracranial pressure caused by edema. Steroids are of uncertain value in these cases, and recently hyperbaric oxygen has been proposed.

Thus, though the application negative (or sub-atmospheric) pressure therapy to wounded cutaneous and subcutaneous tissue demonstrates an increased rate of healing compared to traditional methods (as set forth in U.S. Pat. Nos. 5,645,081 and 5,636,643, 7,198,046, and 7,216,651 as well as US Published Application Nos. 2003/0225347, 2004/0039391, and 2004/0122434, the contents of which are incorporated herein by reference), there remains a need for devices and methods specifically suited for use with the unique tissues of the central nervous system.

SUMMARY OF THE INVENTION

The present invention relates generally to a device and method for treating tissues of the central nervous system using sub-atmospheric pressure and more particularly, but not exclusively, to a device and method for treating brain tissue using sub-atmospheric pressure. According to one exemplary procedure the present invention provides a method for treating damaged central nervous system tissue using sub-atmospheric pressure comprising locating a porous material proximate the damaged central nervous system tissue to provide gaseous communication between one or more pores of the porous material and the damaged central nervous system tissue. In some cases the porous material may be located directly over the damaged central nervous system tissue. The porous material may be sealed in situ proximate the damaged central nervous system tissue to provide a region about the damaged central nervous system tissue for maintaining sub-atmospheric pressure at the damaged central nervous system tissue. A vacuum system may then be operably connected with the porous material and the vacuum system activated to provide sub-atmospheric pressure at the damaged central nervous system tissue. The sub-atmospheric pressure may be maintained at the damaged tissue for a time sufficient to decrease edema at the central nervous system.

In another of its aspects the present invention provides an apparatus for treating damaged central nervous system tissue. The apparatus may include a porous bioabsorbable material, such as an open-cell collagen, having pore structure configured to permit gaseous communication between one or more pores of the porous material and the central nervous system tissue to be treated. The bioabsorbable nature of the porous material can obviate the need for a second procedure to remove the porous material. The apparatus also includes a vacuum source for producing sub-atmospheric pressure; the vacuum source may be disposed in gaseous communication with the porous material for distributing the sub-atmospheric pressure to the central nervous system tissue. The porous material may have, at least at a selected surface of the porous material, pores sufficiently small to prevent the growth of tissue therein. In addition, the porous material may have, at least at a selected surface of the porous material, a pore size smaller than the size of fibroblasts and central nervous system cells, and may have a pore size at a location other than the selected surface that is larger than that of fibroblasts and central nervous system cells. The pore size of the porous material may be large enough to allow movement of proteins the size of albumin therethrough. Also, the porous bioabsorbable material may include at least one surface that is sealed to prevent the transmission of sub-atmospheric pressure therethrough. The apparatus may also include a cover configured to cover the damaged central nervous system tissue to maintain sub-atmospheric pressure under the cover at the damaged central nervous system tissue.

In use, the present invention can provide a pressure gradient to remove edema from the central nervous system, thus preserving neurologic function and increasing the probability of recovery and survival in a more physiologically preserved state. Decrease in central nervous system edema in turn can lead to a decrease in intracranial pressure, minimizing the risk of central nervous system compromise and herniation. In addition to the removal of edema, the present invention can remove mediators, degradation products, and toxins that enhance the inflammatory and neuropathological response of tissues in the central nervous system to injury.

The present invention can protect the central nervous system from exogenous infection and contamination, and facilitates and maximizes healing of the intracranial and adjacent structures when tissues are contaminated by central nervous system abscesses, meningitis, ventriculitis, and brain tissue infection. The central nervous system tissue may also be protected from adjacent infection, such as infection which exists subclinically in the sinuses, oral cavity, and other potentially infected spaces that exist in the normal human state, either by increased blood flow and directly decreasing bacterial load. Moreover, the device and method of the present invention can prepare central nervous system tissue to achieve a stage of healing and diminution of bacterial counts such that acceptance of secondary treatments (e.g., flaps, bone grafts) can be successful.

The present invention can also facilitate closure of pathologic openings communicating between the central nervous system and the extradural space, e.g. between the extradural space and the subdural/epidural, and/or subarachnoid space. Likewise, the progression of pathologic processes, disruption of physiological central nervous system integrity, the interference with central nervous system blood flow and nutrition can be minimized.

The devices and methods of the present invention can be used to treat the following conditions: exposure of the central nervous system as a result of trauma, surgery, infection, or any other pathologic process; treatment of any of the spaces and tissues surrounding the central nervous system, including the subdural/epidural and intraventricular spaces; treatment of edema of the central nervous system parenchyma secondary to any cause, including hemorrhage, trauma, tumor, infection or any other pathologic state; treatment of elevated intracranial and intraspinal pressure due to the any of the aforementioned causes; and treatment of cerebrospinal fluid pathology in which the spinal fluid is pathologically in communication with any non-anatomical and non-physiologic spaces. In addition, the present invention can be used to promote formation of granulation tissue in areas where central nervous system disruption has occurred, and to control cerebrospinal fluid leaks. Further, the modified present material can be used for control or closure of defects existing between the central nervous system, the cutaneous space, intranasal space, and intrasinus space.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
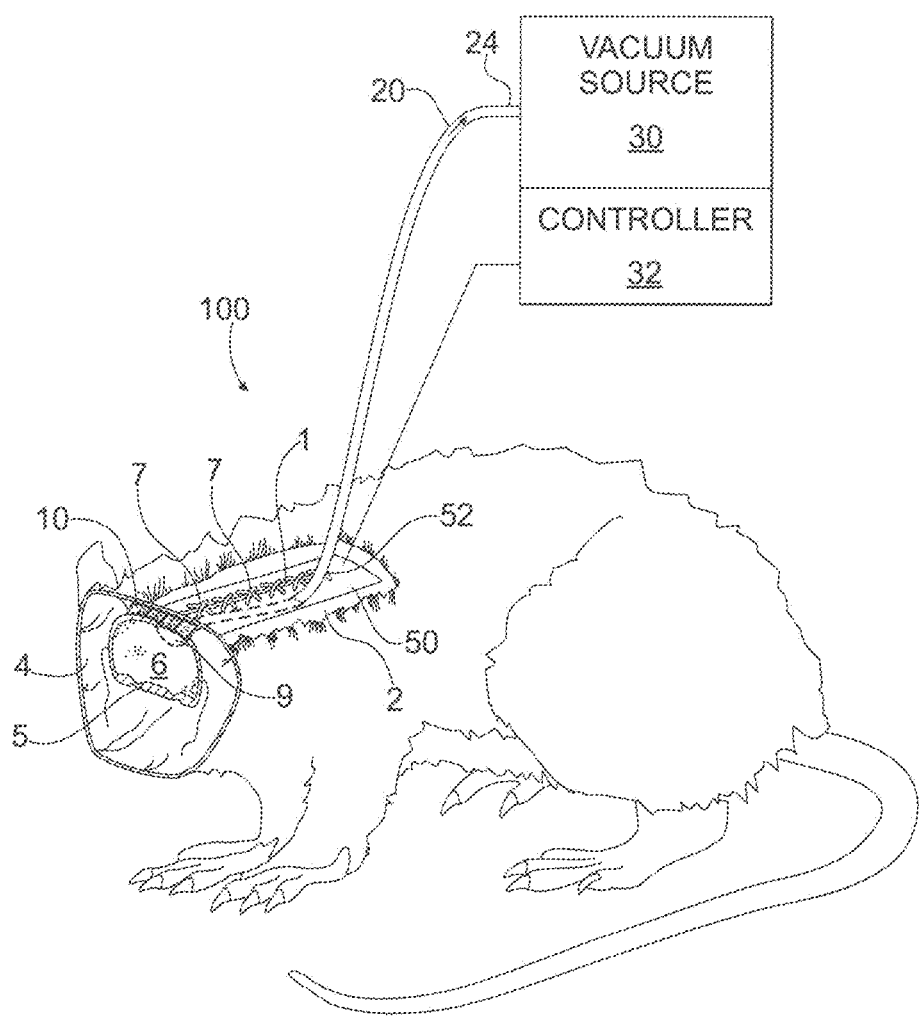
FIG. 1 schematically illustrates a perspective view in partial cross-section of an exemplary apparatus of the present invention in situ showing treatment of an injury to the brain.
Figure 2:
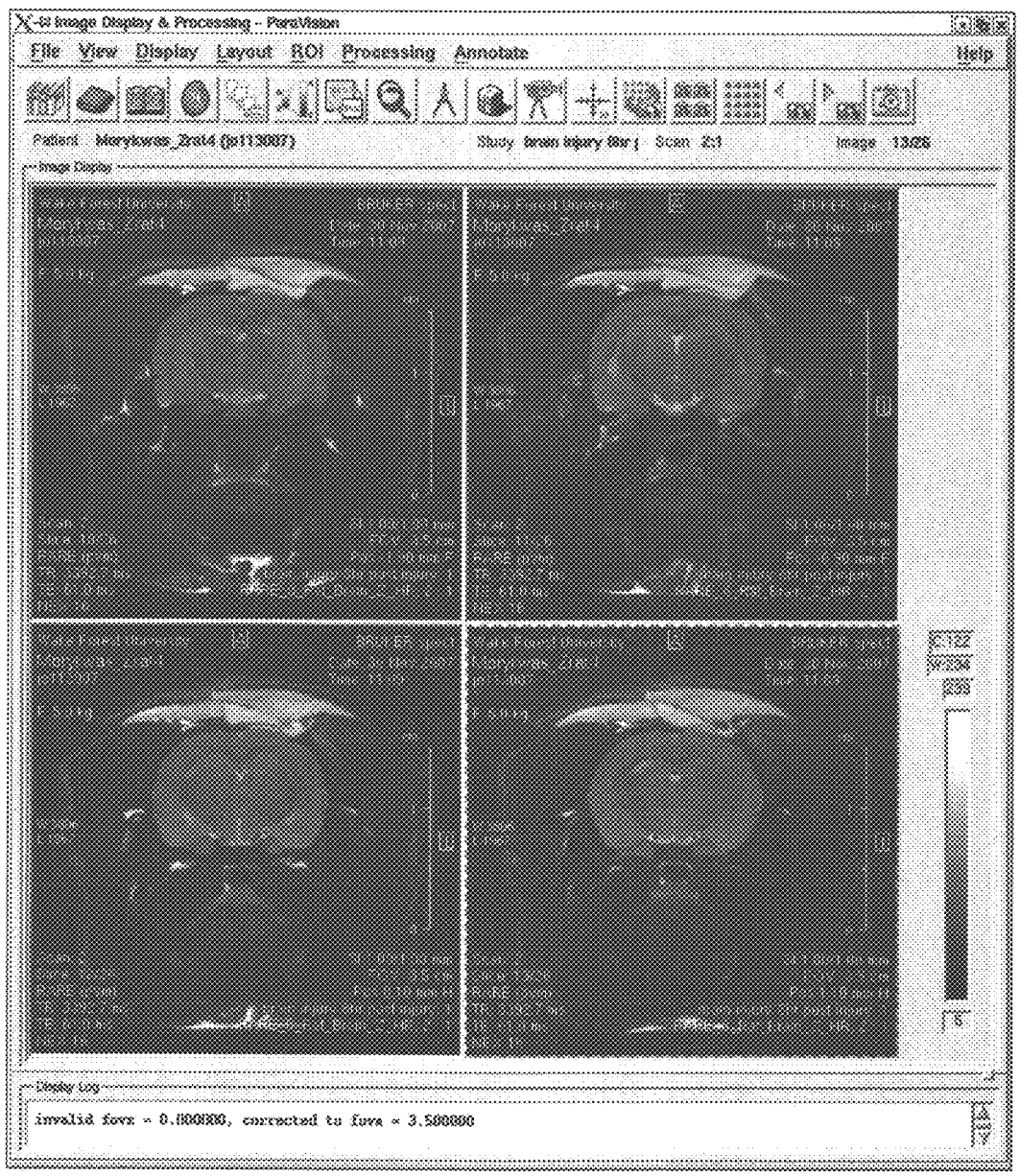
FIGS. 2 and 3 illustrate MRI scans of control animals having brain injuries that were not treated with sub-atmospheric pressure.
Figure 3:
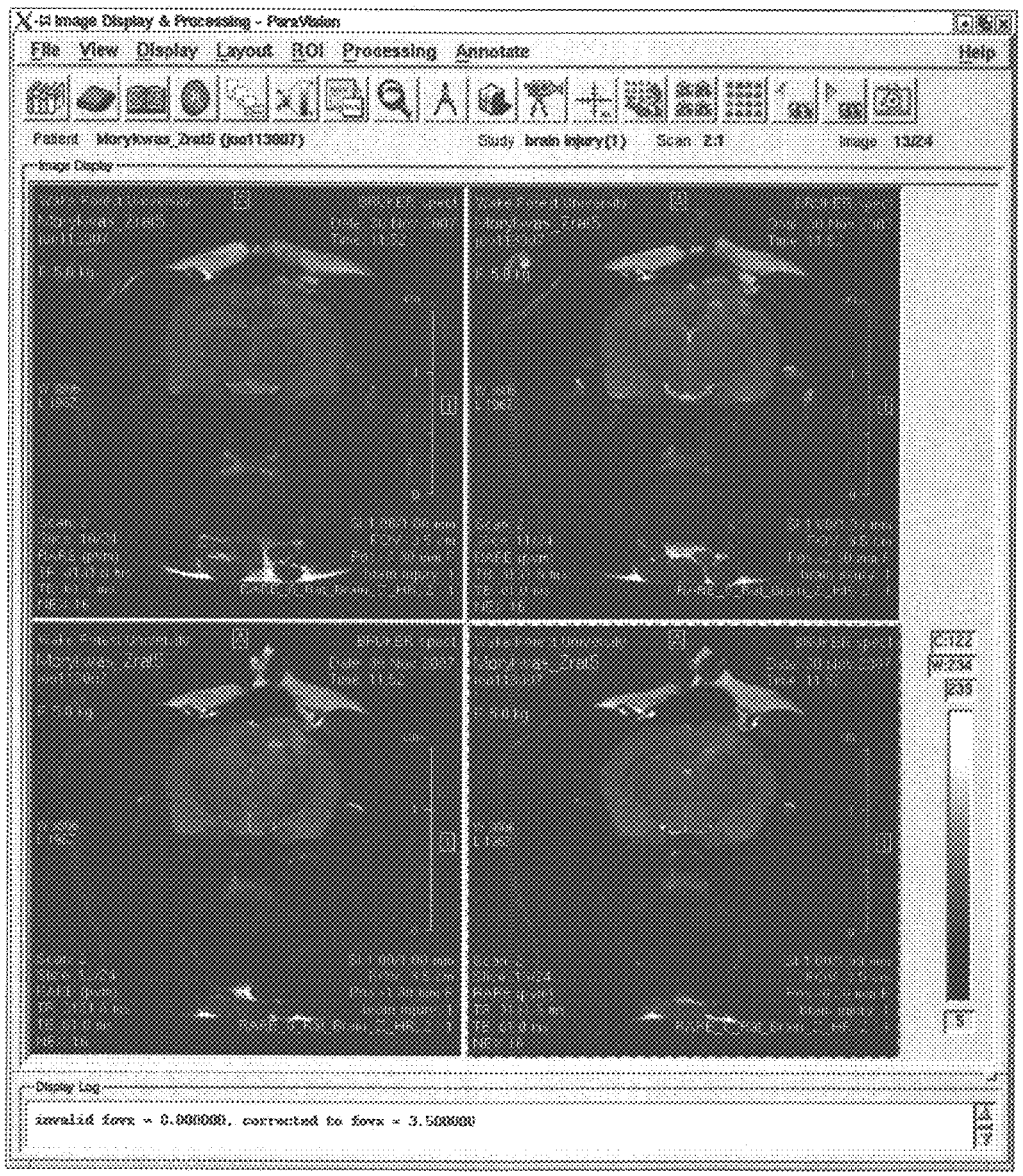
Figure 4:
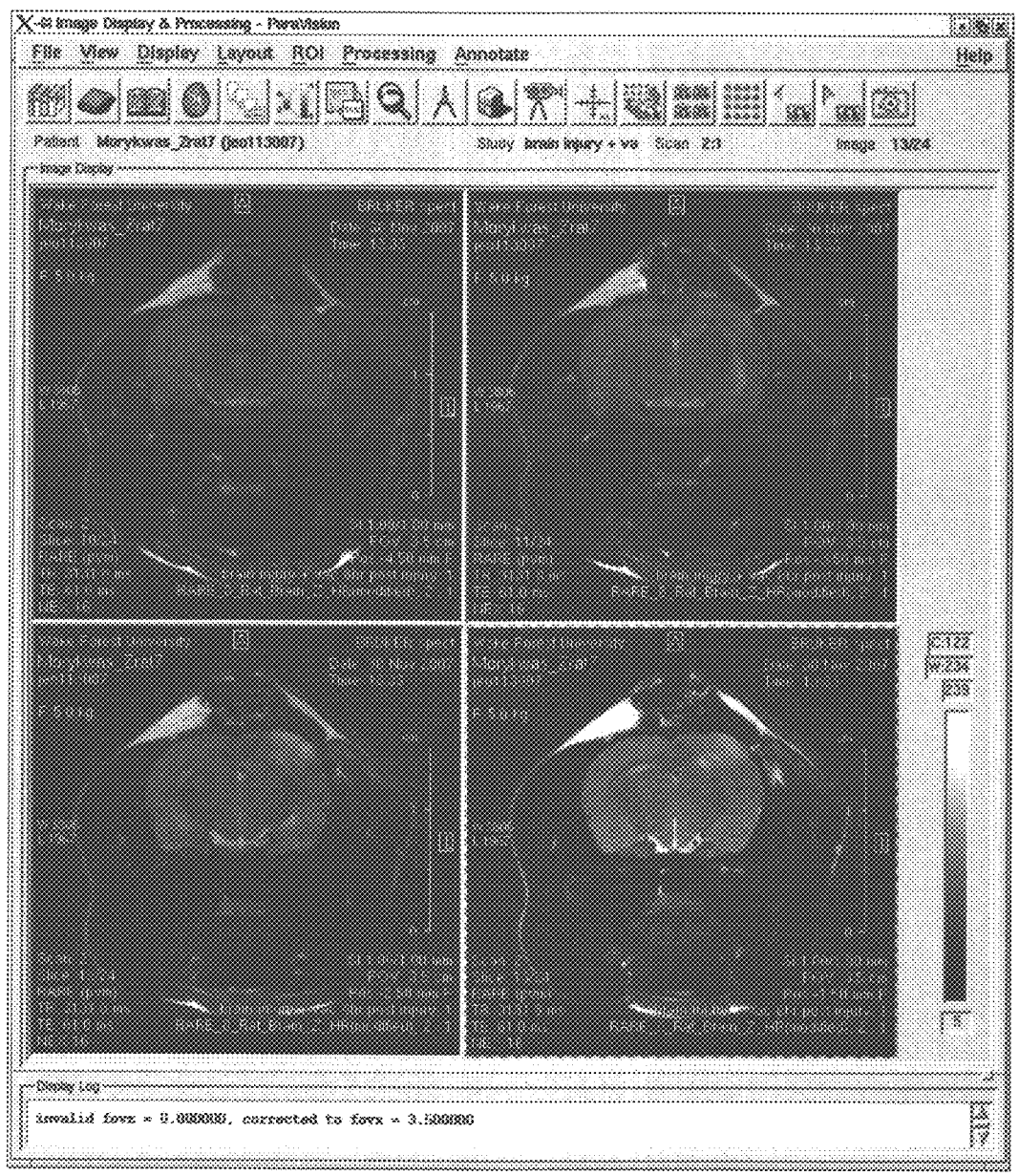
FIG. 4 illustrates an MRI scan of an animal having a brain injury that was treated for 8 hours with sub-atmospheric pressure.
Figure 5:
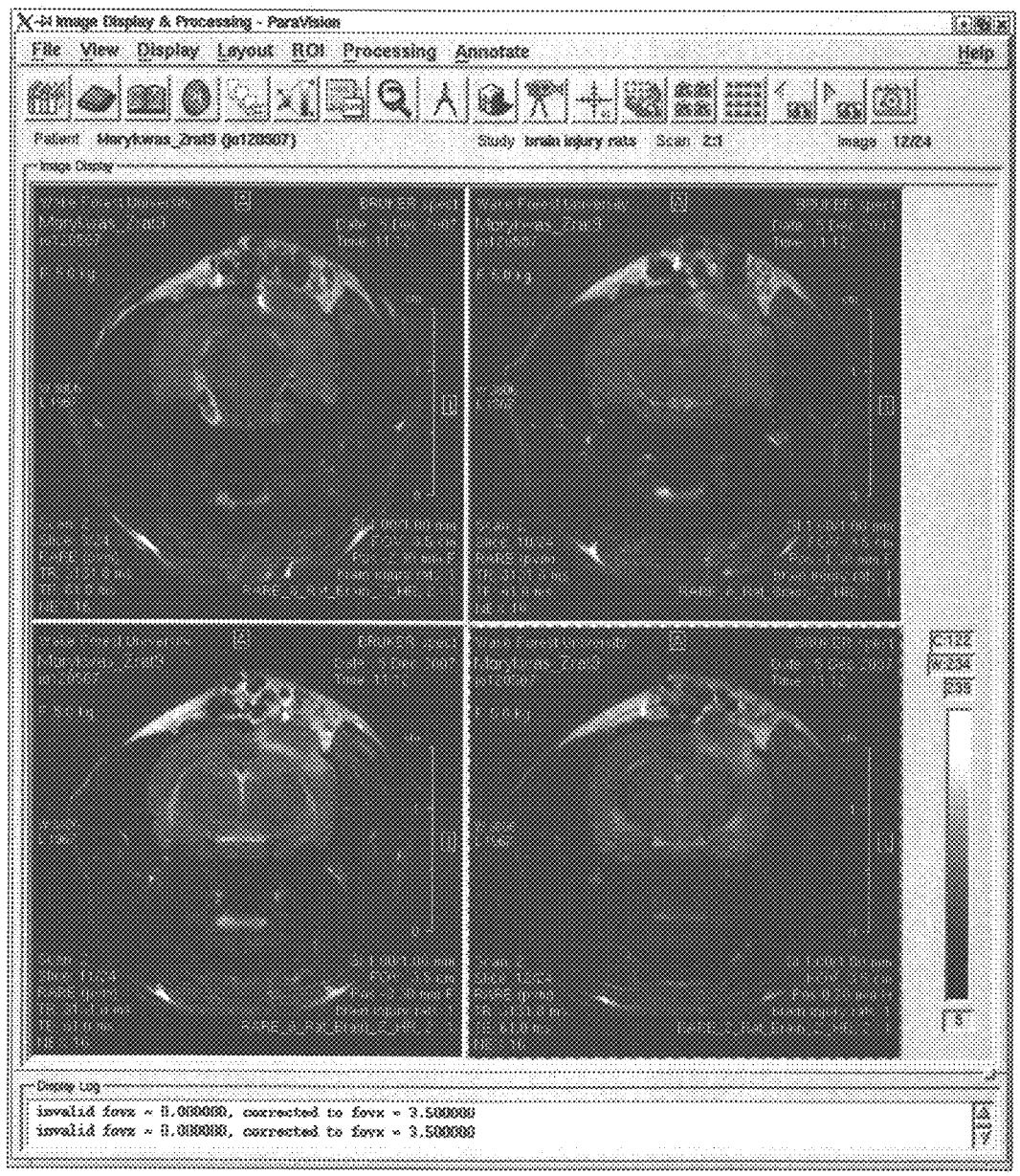
FIG. 5 illustrates an MRI scan of a control animal having a brain injury that was not treated with sub-atmospheric pressure.
Figure 6:
FIGS. 6 and 7 illustrate MRI scans of animals having brain injuries that were treated for 24 hours with sub-atmospheric pressure.
Figure 7:
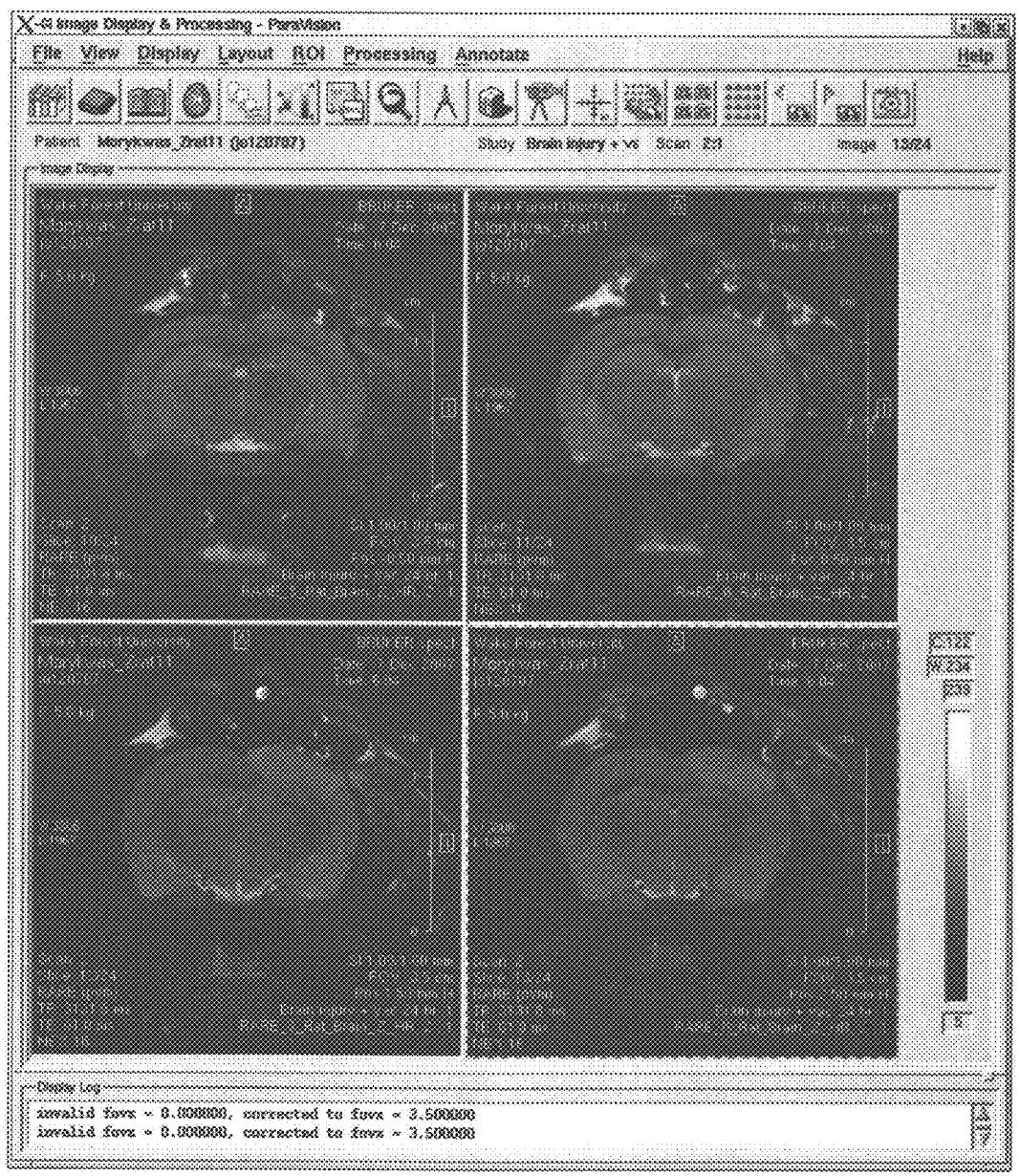
Figure 8:
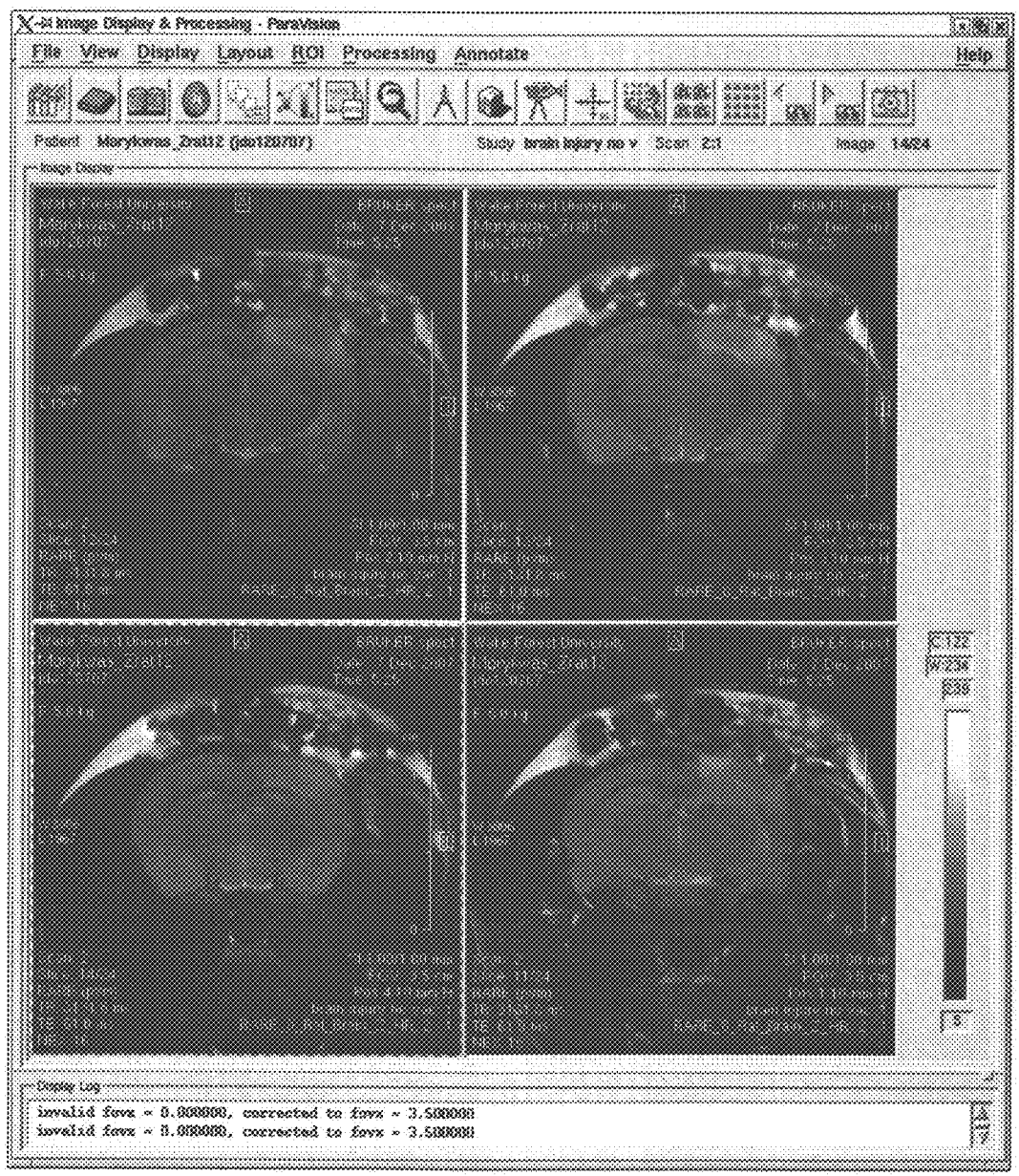
FIG. 8 illustrates an MRI scan of a control animal having a brain injury that was not treated with sub-atmospheric pressure.

Referring now to the figures, wherein like elements are numbered alike throughout, the present invention relates to devices and methods that use sub-atmospheric (or negative) pressure for treating damaged central nervous system tissue. As used herein "damaged" tissue is defined to include tissue that is injured, compromised, or in any other way impaired, such as damage due to trauma, disease, infection, surgical complication, or other pathologic process, for example. Referring specifically to FIG. 1, an exemplary configuration of a sub-atmospheric central nervous system treatment device 100 of the present invention is illustrated. The sub-atmospheric central nervous system treatment device 100 may comprise a porous material 10 disposed proximate the damaged central nervous system tissue, such as brain tissue 9 for example, for delivering and distributing sub-atmospheric pressure to the damaged brain tissue 9. The sub-atmospheric central nervous system treatment device 100 may further include a vacuum source 30 in gaseous communication with the porous material 10 via a tube 20 to provide sub-atmospheric pressure to the damaged brain tissue 9.

Turning to FIG. 1 in greater detail, an exemplary configuration of a sub-atmospheric central nervous system treatment device 100 of the present invention is illustrated in situ in an animal with surrounding tissues shown in partial cross-section. The tissues illustrated include the skin 2, muscle tissue 4, skull bone 5, and the damaged brain tissue 9, above which a portion of the skull bone 5 is missing to provide treatment access to the damaged brain tissue 9. The porous material 10 may be placed in the space proximate the brain tissue 9 to provide sub-atmospheric pressure treatment to the damaged brain tissue 9. The treatment may include reducing intracranial pressure, decreasing edema, removing harmful fluids or undesirable compounds, and so forth, for example.

The porous material 10 may have pores large enough to allow undesirable compounds to be removed from the brain tissue 9 and the surrounding space/tissue(s) and pores small enough to deter or prevent the ingrowth of brain tissue into the porous material 10. In this regard, the pore size may be large enough to permit transport of material such as cytokines, toxic substances, or other mediators away from the brain tissue 9 to reduce such materials to a clinically desirable level. For example, the pore size may be large enough to permit albumin to pass through the porous material 10. In addition, the pores may be small enough (at least where the porous material 10 contacts the brain tissue 9) to deter or prevent the growth of tissue into the porous material 10 so that the porous material 10 does not adhere to and cause damage to the brain tissue 9 when removed. For example, to minimize ingrowth and to avoid the excessive production of granulation tissue which may interfere with the physiologic function of the brain, the pore size may be smaller than the that of fibroblasts and brain cells.

Figure 14:
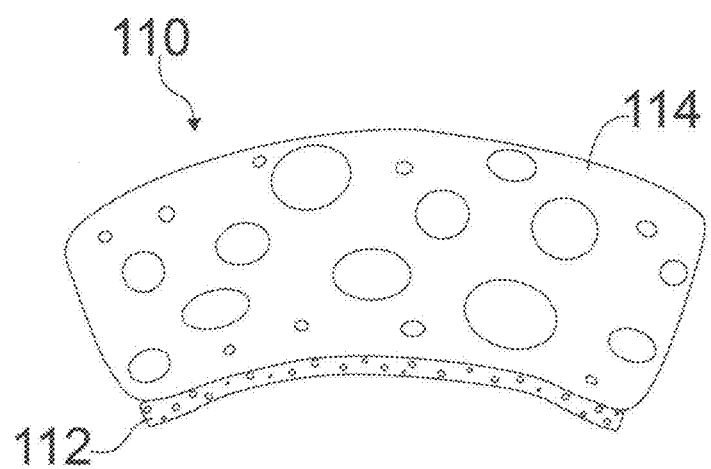
FIG. 14 schematically illustrates a multi-layer porous material of the present invention.

The porous material 10 may be homogeneous in composition and/or morphology or may have a relatively larger pore size interior to the porous material 10 or at any location where the porous material 10 does not contact the brain tissue 9. For example, the porous material 110 may include a non-ingrowth layer 112 with a sufficiently small pore size to prevent the growth of tissue therein for placement in contact with the brain, and may have an additional layer 114 of a different material that has a relatively larger pore size (e.g., larger than that of fibroblasts and brain cells) in contact with the non-ingrowth layer 112 but not in contact with the brain, FIG. 14. For instance, the porous material 10 may have a pore size sufficiently large to promote the formation of granulation tissue at other tissues in the spaces surrounding the damaged brain tissue 9. Additionally, the porous material 10 may include one or more sides or surfaces of the porous material 10 which are sealed to prevent the transmission of sub-atmospheric pressure therethrough, while at the same time having at least one surface through which sub-atmospheric pressure may be transmitted. Such a configuration of the porous material 10 can provide preferential treatment of tissue on one side of the porous material 10 while not treating tissues at the sealed sides. For instance, such a porous material 10 may be used when it is placed on brain parenchyma at its interface with the ventricular space. The parenchyma could be treated with through a surface on one side of the porous material 10; at the same time the sealed surface(s) of the porous material 10 would not drain the ventricular space so the fluid in the ventricular space would not be removed. Similarly, a porous material 10 that varies in its permeability along its length would allow sub-atmospheric pressure to be applied to the brain parenchyma while not promoting subatmospheric pressure in the cerebrospinal fluid (CSF) spaces such as the sulci, the ventricles, and the subarachnoid space and, therefore, not preferentially remove CSF from those spaces.

The porous material 10 may comprise a material is bioabsorbable or degrades harmlessly over time, such as collagen, or a material that needs to be removed after sub-atmospheric therapy is given. The porous material 10 may be one that readily conforms to the surface of brain or cavity walls easily without excessive packing and may do so without excessive trimming and shaping. For example, the porous material 10 may be provided in the form of a ribbon, or string that could be placed on or in the brain/cranium. The ribbon or string may have adequate strength so that it may be pulled out of the head without breaking or leaving residue. For instance, a ribbon or string of porous material 10 may be gradually and progressively removed as the cavity into which it is placed fills in. Thus, the porous material 10 may be in the form of a ribbon or tape or string (e.g., 5×5×200 mm) with enough resilience such that it can be pulled out thought a small hole in the skull 5 after treatment without need for second surgery. The porous material 10 may be a flexible sheet which can be folded and modified to fit in specific areas of the central nervous system such as directly in the brain parenchyma or the ventricular system following trauma.

In addition, the porous material 10 may be sufficiently compliant that so it does not press against the damaged brain to a degree that interferes with brain function. Yet, the porous material 10 may be sufficiently firm so that the porous material 10 does not collapse so much as to pull or distort the brain to a degree that might interfere with brain function. Exemplary materials that may be used in the porous material 10 may include an open-cell collagen material, polyglycolic and/or polylactic acid material, a synthetic polymer, a flexible sheet-like mesh, an open-cell polymer foam, a foam section, a porous sheet, a polyvinyl alcohol foam, a polyethylene and/or polyester material, elastin, hyaluronic acid, alginates, polydiolcitrates, polyhyrdoxybutyrate, polyhyrdoxyfumarate, polytrimethylene-carbonate, polyglycerolsebecate, aliphatic/aromatic polyanhydride, or other suitable materials, and combinations of the foregoing any of which may be fabricated by electrospinning, casting, or printing, for example. Such materials include a solution of chitosan (1.33% weight/volume in 2% acetic acid, 20 ml total volume) which may be poured into an appropriately sized mold. The solution is then frozen for 2 hours at −70° C., and then transferred to the lyophilizer with a vacuum applied for 24 hours. The material may be cross-linked by 2.5%-5% glutaraldehyde vapor for 12-24 hours (or by ultraviolet radiation for 8 hours) to provide a cast porous material 10.

Additionally, the porous material 10 may be made by casting polycapro-lactone (PCL). Polycaprolactone may be mixed with sodium chloride (1 part caprolactone to 10 parts sodium chloride) and placed in a sufficient volume of chloroform to dissolve the components. For example, 8 ml of the solution may be poured into an appropriately sized and shaped contained and allowed to dry for twelve hours. The sodium chloride may then be leached out in water for 24 hours.

It is also possible to use electrospun materials for the porous material 10. One exemplary of a formulation and method for making an electrospun porous material 10 was made using a combination of collagen Type I:chondroitin-6-sulfate (CS): poly 1,8-octanediol citrate (POC) in a ratio of 76%:4%:20%: by weight. Two solvents were utilized for the collagen/CS/POC. The CS was dissolved in water and the collagen and POC were dissolved in 2,2,2-trifluoroethanol (TFE). A 20% water/80% TFE solution (volume/volume) solution was then used. For electrospinning, the solution containing the collagen:CS:POC mixture was placed in a 3 ml syringe fitted to an 18 Ga needle. A syringe pump (New Era Pump Systems, Wantaugh, N.Y.) was used to feed the solution into the needle tip at a rate of 2.0 ml/hr. A voltage of 10-20 kV was provided by a high voltage power supply (HV Power Supply, Gamma High Voltage Research, Ormond Beach. FL) and was applied between the needle (anode) and the grounded collector (cathode) with a distance of 15-25 cm. The material was then cross-linked with glutaraldehyde (Grade II, 25% solution) and heat polymerized (80° C.) for 48 hours. It is also possible to electrospin collagen Type I porous materials 10 starting with an initial concentration of 80 mg/ml of collagen in 1,1,1,3,3,3-hexafluoro-2-propanol (HFP), then use the same electrospinning conditions as the collagen:CS:POC combination.

An additional method for creating porous materials 10 is to use thermal inkjet printing technologies. Bioabsorbable materials such as collagen, elastic, hyaluronic acid, alginates, and polylactic/polyglycolic acid co-polymers may be printed. As examples, Type I collagen (Elastin Products Co., Owensville, Mo.) dissolved in 0.05% acetic acid, then diluted to 1 mg/ml in water can be printed, as can sodium alginate (Dharma Trading Co., San Raphael, Calif.) 1 mg/ml in water. A mixture of Type I collagen (2.86 mg/ml in 0.05% acetic acid) and polylactic/polyglycolic acid (PURAC America, Blair, Nebr.) (14.29 mg/ml in tetraglycol (Sigma Aldrich, St. Louis Mo.)) can also be printed. Hardware from a Hewlett Packard 660c printer, including the stepper motors and carriage for the cartridges, can be mounted to a platform. The height of the hardware above the platform can then be adjusted for printing in layers. The porous material 10 may comprise an MRI-compatible material so an MRI can be performed while the porous material 10 is in place.

Turning next to the delivery of sub-atmospheric pressure to the porous material 10 and distribution to the damaged brain tissue 9, a tube 20 may be connected directly or indirectly in gaseous communication with the porous material 10 at the distal end 22 of the tube 20. For example, the distal end 22 of the tube 20 may be embedded in the porous material 10 or may be placed over the porous material 10. The distal end 22 of the tube 20 may also include one or more fenestrations to assist in delivering the sub-atmospheric pressure to the porous material 10 and the damaged brain tissue 9. The tube 20 may extend through an opening in the skin and subcutaneous tissue 2 which may be secured about the tube 20 with a suture to assist in providing a seal about the tube 20. The proximal end 24 of the tube 20 may be operably connected to a vacuum source 30, such as a vacuum pump, to provide sub-atmospheric pressure that is transmitted via the tube 20 to the porous material 10 and the damaged brain tissue 9.

The vacuum source 30 may include a controller 32 to regulate the production of sub-atmospheric pressure. For instance, the vacuum source 30 may be configured to produce sub-atmospheric pressure continuously or intermittently; e.g. the vacuum source 30 may cycle on and off to provide alternating periods of production and non-production of sub-atmospheric pressure. The duty cycle between production and non-production may be between 1 to 10 (on/off) and 10 to 1 (on/off). In addition, intermittent sub-atmospheric pressure may be applied by a periodic or cyclical waveform, such as a sine wave. The vacuum source 30 may be cycled after initial treatment to mimic a more physiologic state, such as several times per minute. The sub-atmospheric pressure may be cycled on-off as-needed as determined by monitoring of the pressure in the damaged brain tissue 9. In general, the vacuum source 30 may be configured to deliver sub-atmospheric pressure between atmospheric pressure and 75 mm Hg below atmospheric pressure (such as ~20 mm Hg, for example) to minimize the chance that the sub-atmospheric pressure may be deleterious to the brain parenchyma. (Excessive negative pressure may result in bleeding into the parenchyma). The application of such a sub-atmospheric pressure can operate to remove edema from the damaged brain tissue 9, thus preserving neurologic function to increase the probability of recovery and survival in a more physiologically preserved state. In addition, the application of sub-atmospheric pressure can normalize intracranial pressure to a clinically desirable level, normalize tissue volume and density to a clinically desirable level, and/or normalize at least one of blood pressure and heart rate to a clinically desirable level. For example, the application of sub-atmospheric pressure can normalize intracranial pressure to a substantially normal, pre-damage physiological state, normalize tissue volume and density to a substantially normal, pre-damage physiological state, and/or normalize at least one of blood pressure and heart rate to a substantially normal, pre-damage physiological state.

Figure 11:
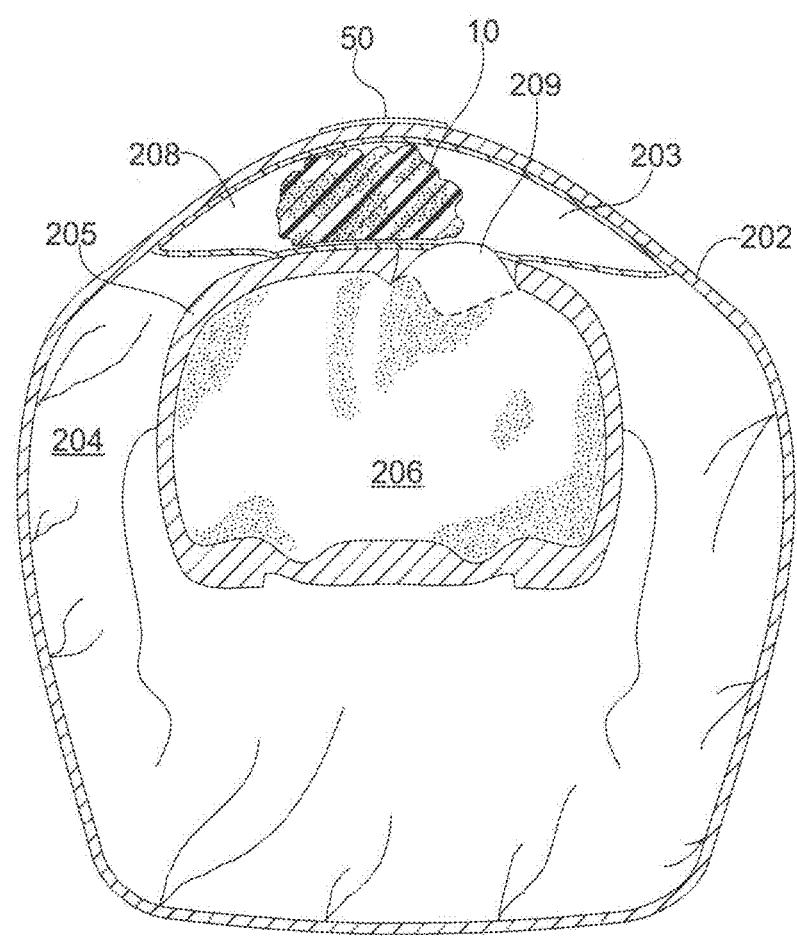
FIG. 11 schematically illustrates in partial cross-section slice 12/24 of the animal of FIG. 4, showing the area of impaction with porous material and drape in place.
Figure 12:
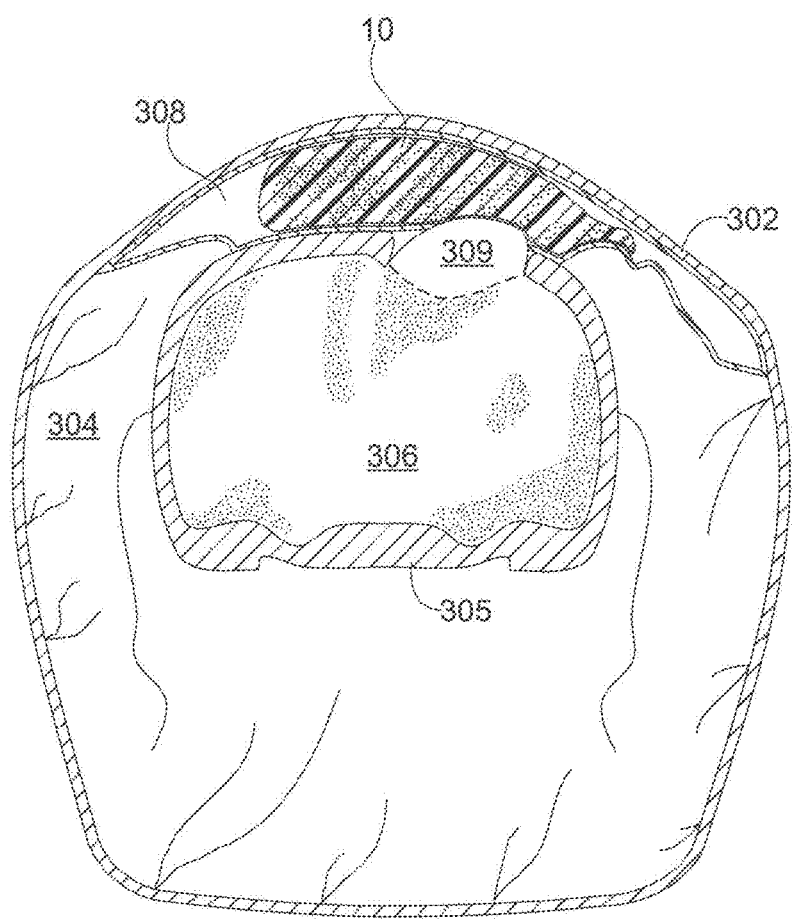
FIG. 12 schematically illustrates in partial cross-section slice 12/24 of the animal of FIG. 5, showing the area of impaction with porous material in place.
Figure 13:
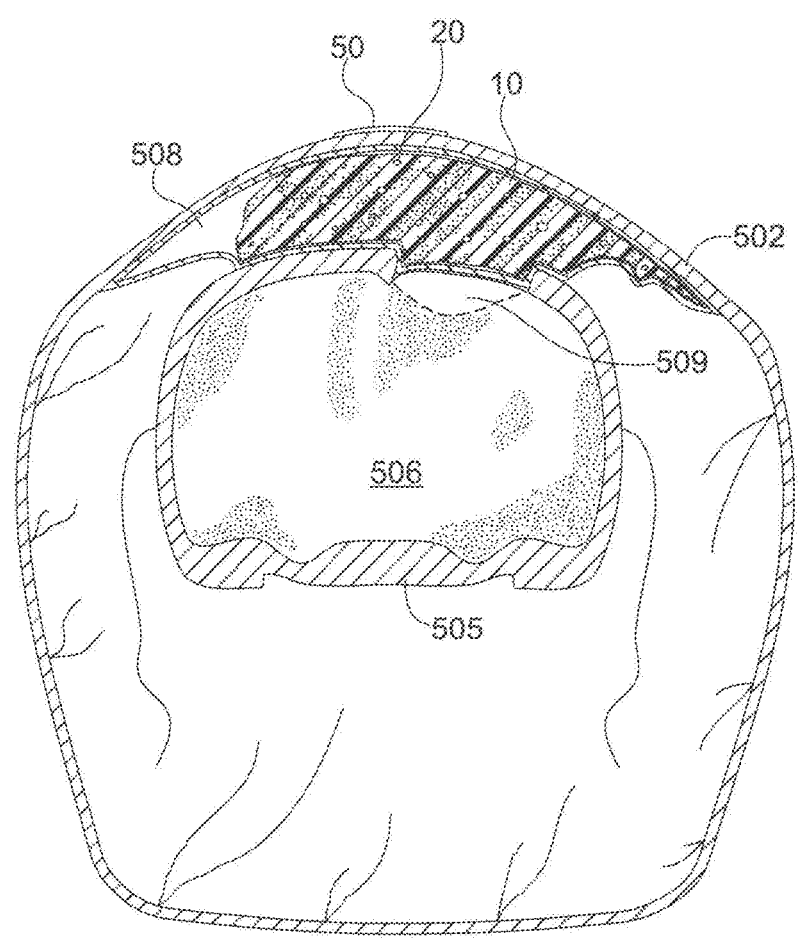
FIG. 13 schematically illustrates in partial cross-section slice 12/24 of the animal of FIG. 6, showing the area of impaction with porous material and drape in place.

To assist in maintaining the sub-atmospheric pressure at the damaged brain tissue 9, a flexible cover/sheet 50 or rigid (or semi-rigid) cover may be provided proximate the damaged brain tissue 9 to provide a region about the damaged brain tissue 9 where sub-atmospheric pressure may be maintained. Specifically, with reference to FIGS. 1, 11, 13, a cover 50 may be provided over the damaged brain tissue 9 and porous material 10 by adhering the cover 50 to tissues such as skin 2, 202, 502 proximate the damaged brain tissue 9 to define an enclosed region about the damaged brain tissue 9 and porous material 10. For instance, the cover 50 may be glued to the skin 2, 202, 502 and/or other appropriate tissues using an adhesive, such as a fibrin glue. The adhesive may comprise an auto-polymerizing glue and/or may desirably include a filler to provide the adhesive with sufficient bulk to permit the adhesive to conform to the shapes of the potentially irregular surfaces which the adhesive contacts. The adhesive may be provided as a separate component or as a portion of the cover 50 to provide a self-adhesive cover 50. For instance, the cover 50 may comprise a flexible self-adhesive sheet which includes a suitable adhesive on one or more of its surfaces.

Sub-atmospheric pressure may be delivered under the cover 50 by cooperation between the cover 50 and the tube 20. Specifically, the cover 50 may include a vacuum port to which the distal end 22 of the tube 20 connects to provide gaseous communication between the tube 20 and the space under the cover 40 over the damaged brain tissue 9. Alternatively, the cover 50 may include a pass-through 52 through which the tube 20 passes so that the distal end 22 of the tube 20 is disposed interior to, and in gaseous communication with, the space under the cover 50 over the damaged brain tissue 9, FIG. 1. In addition the cover 50 may further protect the damaged brain tissue 9 from exogenous infection and contamination beyond the protection already afforded by the porous material 10 and sutured skin 2. Likewise, the cover 50 may further protect surrounding tissues from the spread of infection from the damaged brain tissue 9 such as brain abscesses, meningitis, and spinal tissue infection. As an alternative, a cover 50 need not be used and the skin 2 and/or dura may sutured, stapled, or clipped closed to provide a region about the damaged brain tissue 9 at which sub-atmospheric pressure may be provided.

In another of its aspects, the present invention also provides a method for treating damaged brain tissue using sub-atmospheric pressure. In particular, the method may comprise locating a porous material 10 proximate the damaged brain tissue 9 to provide gaseous communication between one or more pores of the porous material 10 and the damaged brain tissue 9. The porous material 10 may be sealed in situ proximate the damaged brain tissue 9 to provide a region about the damaged brain tissue 9 for maintaining sub-atmospheric pressure at the damaged brain tissue 9. A tube 20 may be connected to the porous material 10 at a distal end 22 of the tube 20, and the porous material 10 may be sealed in situ by sutures 7 in the skin 2 and subcutaneous tissues to provide a region about the damaged brain tissue 9 for maintaining sub-atmospheric pressure. A further airtight dressing or cover 50 may optionally be placed over the suture site to promote an airtight seal. The method may also include the step of adhesively sealing and adhering the cover 50 to tissue, e.g., skin 2, surrounding the damaged brain tissue 9. The cover 50 may be provided in the form of a self-adhesive sheet 50 which may be located over the damaged brain tissue 9. In such a case, the step of sealing the cover 50 may include adhesively sealing and adhering the self-adhesive sheet 50 to tissue surrounding the damaged brain tissue 9 to form a seal between the sheet 50 and tissue surrounding the damaged brain tissue 9. In addition, the step of operably connecting a vacuum system 30 in gaseous communication with the porous material 10 may comprise connecting the vacuum system 30 with the vacuum port of the cover 40.

The proximal end 24 of the tube 20 may be attached to a vacuum source 30 to supply sub-atmospheric pressure to the damaged brain tissue 9 upon activation of the vacuum system 30. For example, the sub-atmospheric pressure may be maintained at about 20 to 75 mm Hg below atmospheric pressure. The sub-atmospheric pressure may be maintained at the damaged brain tissue 9 for a time sufficient to: 1) normalize intracranial pressure to a substantially normal, pre-damage physiological state; 2) normalize tissue volume and density to a substantially normal, pre-damage physiological state; 3) normalize at least one of blood pressure and heart rate to a substantially normal, pre-damage physiological state; 4) decrease cytokines, toxic substances, or other mediators to a clinically desirable level; and/or 5) improve cognition, consciousness, motor or sensory function of the patient, which may be indicated by the Glasgow score. In addition, the sub-atmospheric pressure may be maintained at the damaged brain tissue 9 for a time sufficient to prepare the brain tissue 9 to achieve a stage of healing and diminution of bacterial counts such that acceptance of secondary treatments (e.g., flaps) can be successful.

The method may be used for at least three hours, or can be used for many days. At the end of the vacuum treatment, the sutures 7 may be removed and the skin 2 re-opened. The porous material 10 may then be removed and the skin 2 is re-sutured closed.

EXAMPLES

Rat Brain Injuries and Sub-atmospheric Pressure Exposure

Experiment 1

An experiment was conducted to develop a model of brain contusion and vacuum treatment of the contused brain. Twelve (12) 300 gram Sprague Dawley rats were procured and allowed to acclimated to the housing conditions. For two of the animals, a MRI scan (Bruker Biospin Horizontal Bore 7 Tesla small animal scanner, Ettlingen, Germany) of the brain was obtained before any other procedures were performed. The animals were sedated with isoflurane (2% inhalation) and the scan of the brain obtained. The animals were allowed to recover from anesthesia and returned to their cages. For creation of the injury, on the day of surgery the animals were sedated with isoflurane (2-2.5% inhalation). The top of the head was shaved and the hair removed with a depilatory agent. A midline incision 1 was made down to the bone 5, FIG. 1. The right side of the skull was removed exposing the right half of the brain; the dura was left intact. The animal was placed into the stereotaxic holder on the impactor device (Pneumatic (Cortical) Impact Device; AmScien Instruments, Richmond Va.). The right forebrain of each animal was then impacted. For the first animal, a 3 mm diameter rod was impacted to a depth of 2.0 mm (Table 1, rat no. 1). This injury was not deemed to be significant enough. An attempt was made in animal 2 to increase the severity of the injury. The second animal had a 6 mm diameter rod impacted to a depth of 2.5 mm into the brain. (Table 1, rat no. 2). This injury was deemed to be too severe. For the remaining animals, a 6 mm diameter rod was impacted to a depth of 2.0 mm into the right forebrain. (Table 1, rat nos. 3-12). For the two animals in which a MRI scan had been performed prior to surgery, both animals died within 5 minutes post impaction. (Table 1, rat nos. 3 and 8.).

Two non-treatment, control animals were successfully impacted and allowed to recover from anesthesia in heated cages. (Table 1, rat nos. 4 and 5). Eight hours later the animals were re-anesthetized and a MRI scan was obtained to visualize the degree of swelling and presence of water (T2 weighted MRI image). Two vacuum treatment animals were then successfully impacted and a small piece of polyvinyl alcohol vacuum dressing (VersaFoam, Kinetic Concepts, Inc., San Antonio, Tex.) the size of the removed bone was placed over the brain. (Table 1, rat nos. 6 and 7). A small bore evacuation tube was placed on top of the dressing and below the skin. The end of the tube was cut at an angle and positioned so that the opening at the end of the tube abutted against the dressing. A side port was also cut into the side of the evacuation tube positioned so that the port was in contact with the foam dressing. The tube exited the incision site and the incision was sutured closed. A piece of thin film dressing (Ioban, 3M, St. Paul, Minn.) was placed over the incision to ensure an airtight seal. The animals were allowed to recover from anesthesia and placed into heated cages. The small bore evacuation tube was connected with a vacuum source. A low level vacuum, 25 mm Hg, i.e. 25 mm Hg below atmospheric pressure, was applied to the injured area for 8 hours for these two animals. The animals were then re-anesthetized with isoflurane (2% inhalation) and a MRI scan was performed. For one animal, the injured site was compressed when placing the animal into the MRI scanner, inducing an additional but un-quantified injury to the brain. (Table 1, rat no. 6). The scan of this animal showed that brain tissue was extruded around one edge of the vacuum dressing.

Figure 9:
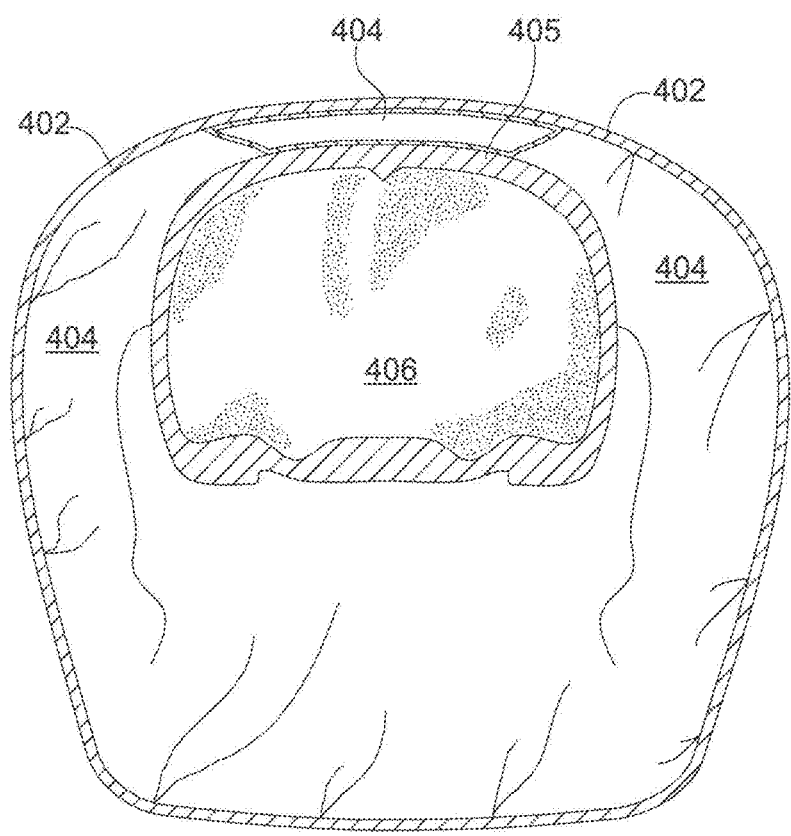
FIG. 9 schematically illustrates in partial cross-section the normal anatomy of the rat skull including the brain and surrounding muscle, bone, and other tissues.
Figure 10:
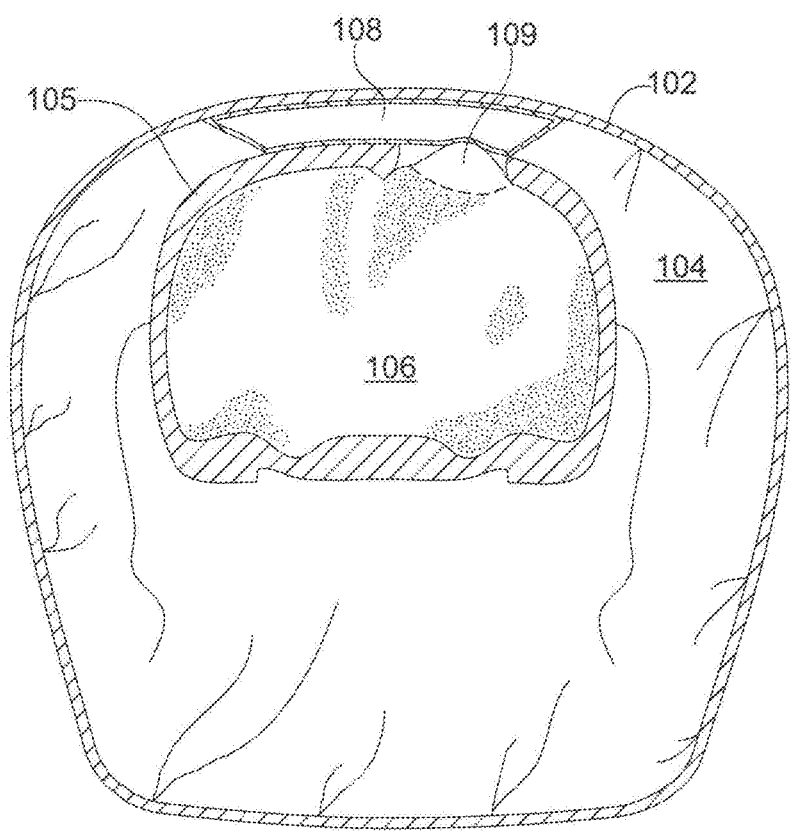
FIG. 10 schematically illustrates in partial cross-section slice 12/26 of the animal of FIG. 2, showing the area of impaction and accumulation of blood or fluid.

Two additional control animals were successfully impacted and a piece of the polyvinyl alcohol vacuum dressing was placed over the removed bone. (Table 1, rat nos. 9 and 12). The vacuum dressing was larger in area than that of the removed bone, and extended slightly (1-2 mm) outside the periphery of the hole that was created to expose the brain. The skin was then sutured closed and the animals were allowed to recover from anesthesia in heated cages. The animals were then re-anesthetized 24 hours later and a MRI scan was obtained. Two additional vacuum treatment animals were successfully impacted, and a larger vacuum dressing, which extended slightly (1-2 mm) outside the periphery of the hole that was created to expose the brain, was placed. A small bore evacuation tube exited the incision site and the incision was sutured closed. The evacuation tube exited the incision site parallel to the uninjured skin in the direction of the tail. A suture 7 was placed in the skin 2 of the neck and the evacuation tube 20 was secured to the skin 2 by this suture 7 to prevent the evacuation tube 20 from being displaced while the animal was ambulating. (Table 1, rat nos. 10 and 11). A small piece of the thin film dressing 50 was again placed to ensure an airtight seal. Low level vacuum, 25 mm Hg, was applied for 24 hours. The animals were then re-anesthetized and a MRI scan was obtained. At this time it was discovered that the evacuation tubing for one of these animals was blocked by a blood clot, and it was not discernible whether the vacuum was actually applied to the injured area. (Table 1, rat no. 11). FIGS. 2-8 illustrate MRI images of the rats as indicated in column 5 of Table 1, and FIGS. 10-13 schematically illustrate in partial cross-section of a selected slice from the MRI images, where reference numerals ending in "2" (i.e., 102, 202, 302, 502) refer to skin, numerals ending in "3" (e.g., 203) refer to an air pocket, numerals ending in "4" refer to muscle, numerals ending in "5" refer to skull bone, numerals ending in "6" refer to the brain, numerals ending in "8" refer to blood or other liquid, and numerals ending in "9" refer to the area of brain impaction. FIG. 9 schematically illustrates in partial cross-section the same view as FIGS. 10-13 using the same numbering conventions (i.e., skin 402, muscle 404, skull bone 405, brain 406), but in an animal prior to undergoing any of the procedures used in these experiments.

Figure 15A:
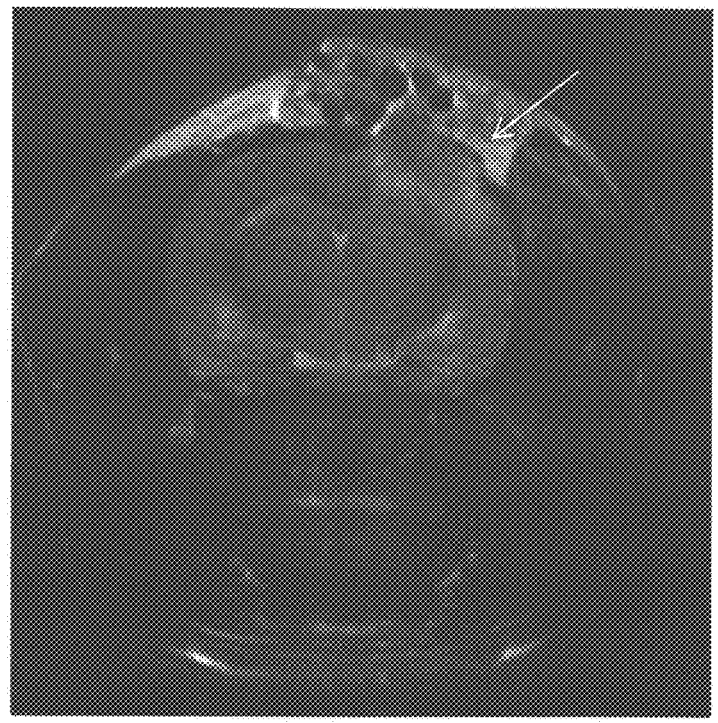
FIGS. 15A and 15B illustrate the lower right panel of the MRI scan of FIGS. 5 and 6, respectively, enlarged to show the relatively greater fluid content in the impacted brain of the non-treated animal.
Figure 15B:

The results of the animal study showed that the control animals exhibited significant swelling with excess water in the injured tissue 109, 309 at both 8 and 24 hours post impaction. (Table 1, rat nos. 4, 5, 9, and 12, FIGS. 2, 10, 3, 5, 12, 8). The vacuum treated animals showed much less swelling and much less excess water in the injured area 209, 509 at both 8 and 24 hours post impaction (8 hours and 24 hours of vacuum treatment). (Table 1, rat nos. 7 and 10, FIGS. 4, 11, 6, 13. Also rat no. 9, FIG. 15A, versus rat 10, FIG. 15B). Based on these results it was concluded that impaction of rat brain with 6 mm diameter rod to a depth of 2.0 mm produced a significant degree of swelling post impaction which was more significant at 24 hours than 8 hours. Application of 25 mm Hg vacuum to the brain dramatically reduced swelling of the brain, particularly dramatic at 24 hours post impaction with 24 hours vacuum application.

TABLE 1

| Rat No. | Rod diameter (mm) | Depth (mm) | Group | Figure No. | Complications | MRI* |
|---|---|---|---|---|---|---|
| 1 | 3 | 2.0 | Control | | None | None |
| 2 | 6 | 2.5 | Control | | None | 8 hours post-impaction |
| 3 | 6 | 2.0 | | | Died within 5 minutes post impaction | Pre-impaction |
| 4 | 6 | 2.0 | Control | 2, 10 | None | 8 hours post-impaction |
| 5 | 6 | 2.0 | Control | 3 | None | 8 hours post-impaction |
| 6 | 6 | 2.0 | Vacuum - Small sponge | | Bleeding - compression on injured site when inserted into MRI machine | 8 hours post-impaction |
| 7 | 6 | 2 | Vacuum - Small sponge | 4, 11 | None | 8 hours post-impaction |

TABLE 1-continued

| Rat No. | Rod diameter (mm) | Depth (mm) | Group | Figure No. | Complications | MRI* |
|---|---|---|---|---|---|---|
| 8 | 6 | 2.0 | | | Died within 5 minutes post impaction | Pre-impaction |
| 9 | 6 | 2 | Control - large sponge | 5, 12 | None | 24 hours post-impaction |
| 10 | 6 | 2.0 | Vacuum - large sponge | 6, 13 | None | 24 hours post-impaction |
| 11 | 6 | 2.0 | Vacuum - large sponge | 7 | Vacuum tubing occluded with blood clot | 24 hours post-impaction |
| 12 | 6 | 2 | Control - large sponge | 8 | None | 24 hours post-impaction |

*MRI scans are T2 weighted images in which water appears white.

Comments:

Rat 1—animal to develop model, small diameter rod (3 mm) used for impaction—not included in results.

Rat 2—animal to develop model, 6 mm diameter plunger at 2.5 mm produced large injury, decreased depth to 2 mm for rest of animals—not included in results.

Rat 3—pre-impaction MRI scan performed for comparison with post impaction scan, but animal died within minutes of impaction.

Rat 4—control animal with MRI scan 8 hours post impaction showing swelling and protrusion of brain at area of impaction.

Rat 5—control animal with MRI scan 8 hours post impaction showing swelling and protrusion of brain at area of impaction.

Rat 6—vacuum treated animal with continual bleeding until vacuum applied. Small piece of polyvinyl alcohol dressing placed into hole in skull. MRI scan 8 hours post impaction/treatment. MRI technician pressed on/compressed brain when placing animal in MRI scanner with additional trauma to brain—not included in results because of human error.

Rat 7—vacuum treated animal with small piece of polyvinyl alcohol dressing placed into hole in skull. MRI scan 8 hours post impaction/treatment.

Rat 8—pre-impaction MRI scan performed for comparison with post-impaction scan, but animal died within minutes of impaction.

Rat 9—control animal with larger diameter sponge placed over defect in skull, extending beyond edges of defect. Skin sutured over sponge. Sponge placed to determine if sponge under sutured skin would be a mechanical impediment to swelling. MRI scan 24 hours post impaction.

Rat 10—vacuum treated animal with larger diameter sponge placed over defect in skull, extending beyond edges of defect. Skin sutured over sponge. Vacuum applied immediately after impaction for 24 hours, then MRI scan.

Rat 11—vacuum treated animal with larger diameter sponge placed over defect in skull, extending beyond edges of defect. Skin sutured over sponge. Vacuum applied immediately after impaction for 24 hours, then MRI scan. Tubing was clogged with blood clot and not able to determine when tube was clogged and if vacuum was actually applied to brain. Not included in results.

Rat 12—control animal with larger diameter sponge placed over defect in skull, extending beyond edges of defect. Skin sutured over sponge. Sponge placed to determine if sponge under sutured skin would be a mechanical impediment to swelling. MRI scan 24 hours post impaction.

Experiment 2

Cell death following traumatic brain injury is biphasic, with initial death due to the trauma itself, then an ongoing death as sequella to the release of excitatory amino acids, buildup of lactate, etc. The release of excitatory amino acids (glutamate, aspartate) cause a disturbance in ion homeostasis via agonist opened channel, thus increasing energy demand and increasing lactate production. Elevated levels of glutamate have been shown to be correlated with increased levels of lactate. This increase in lactate is reflective of increased energy demand during periods of impaired supply (ischemia), and is inversely related to patient outcome. Lactate production leads to apoptotic neuronal cell death.

In this preliminary study, anesthetized rats underwent an 8 mm diameter craniectomy between the bregma and lambda, 1 mm lateral to the midline. A controlled cortical impact injury with intact dura was created using the apparatus of Example 1. The impactor tip was 6 mm in diameter and the impact depth was 2 mm. The sham group had only the craniectomy; the non-treated control was impacted; and, the treated group was impacted and had 25 mm Hg sub-atmospheric pressure applied for either 48 or 72 hours.

Twenty-four hours after brain injury, the rats were anesthetized with isoflurane and placed inside a Litz-cage volume coil (38 mm inside diameter). All MRI and MRS experiments were performed using a horizontal 7T magnet (the Bruker Biospin apparatus of Example 1). A Rapid Acquisition with Relaxation Enhancement (RARE) pulse sequence with a RARE factor of 8 was used to acquire T2-weighted images. The Repetition Time (TR) was 1500 ms, the Echo Time (TE) was 41 ms, Number of Excitations (NEX) was 1, Field of View (FOV) was 4, and matrix size was 128×128.

Point Resolved Spectroscopy Sequence (PRESS) was used with a repetition time (TR) of 2500 ms, Echo Time (TE) of 20 ms, Number of Excitations (NEX) of 256, and a cubic voxel with a side length of 4 mm Variable Power Radio frequency with Optimized Relaxation Delays (VAPOR) water suppression was used during acquisition of the metabolite spectrum.

The tissue volume and integrated density of the injury (impacted) areas were calculated from the MRI scans 24 hours post impaction, with the dorsal third ventricle used as a reference for measurements. The results are shown in Table 2, with tissue volume and integrated density of injury areas in T2 weighed MRI. The tissue volume and density for the non-treated, impacted areas of the brain were significantly larger ($p<0.01$) than for the sham and treated areas. The tissue volume and integrated density for the sham and treated areas were not significantly different. An additional measure of edema is water content. Table 3 shows the water content (wet weight-dry weight/wet weight %) of the brain tissues with/without 48 hours after surgery/impaction. Water content of the treated areas is significantly lower than for the non-treated animals, $p<0.05$.

Tissue Volume and Integrated Density

TABLE 2

| Animal number | Volume (mm$^3$) | Volume-contralateral | Density | Density-contralateral |
|---|---|---|---|---|
| Sham | | | | |
| 18 | 122.21 | 121.405 | 1143068 | 1151479 |
| 21 | 103.237 | 101.946 | 1074570 | 1047381 |
| 22 | 108.095 | 108.003 | 987301 | 1010355 |
| 31 | 90.507 | 90.51 | 904097 | 851562 |
| 30 | 100.637 | 100.881 | 903032 | 887497 |
| 34 | 111.872 | 111.536 | 1085521 | 1068646 |
| 49 | 94.021 | 93.423 | 866348 | 876732 |
| Mean ± SD | 104.37 ± 10.8 | 103.96 ± 10.67 | 994848 ± 107843 | 984807 ± 114222 |

TABLE 2-continued

| Animal number | Volume (mm³) | Volume-contralateral | Density | Density-contralateral |
|---|---|---|---|---|
| Injured-no treatment | | | | |
| 27 | 129.981 | 104.6 | 1320469 | 953856 |
| 23 | 126.563 | 94.97 | 1183706 | 595285 |
| 20 | 119.852 | 101.367 | 1366772 | 957840 |
| 16 | 130.564 | 110.152 | 1359632 | 1062747 |
| 14 | 115.909 | 85.272 | 1380052 | 819699 |
| 12 | 127.77 | 103.124 | 1273593 | 851296 |
| 9 | 137.219 | 105.834 | 1470416 | 952034 |
| 29 | 137.872 | 111.114 | 1450040 | 990626 |
| 33 | 132.602 | 95.105 | 1511471 | 801290 |
| 37 | 141.124 | 93.779 | 1658429 | 871572 |
| 40 | 127.162 | 93.535 | 1338592 | 866975 |
| 41 | 127.162 | 95.367 | 1365380 | 873275 |
| 42 | 138.04 | 103.255 | 1342099 | 841890 |
| Mean ± SD | 130.14 ± 7.3 | 99.80 ± 7.48 | 1386203 ± 117167 | 879875 ± 113947 |
| Injured-treated | | | | |
| 10 | 129.389 | 122.974 | 1196508 | 1065277 |
| 11 | 135.218 | 130.77 | 1393198 | 1207696 |
| 13 | 128.34 | 119.66 | 1295263 | 1098217 |
| 19 | 117.629 | 114.788 | 1246274 | 1079762 |
| 26 | 104.581 | 97.797 | 1039937 | 853611 |
| 28 | 119.836 | 119.221 | 1290085 | 1209136 |
| 35 | 116.039 | 111.61 | 1197579 | 986314 |
| 39 | 99.535 | 95.815 | 971668 | 881767 |
| 45 | 93.255 | 83.329 | 884885 | 767881 |
| 48 | 86.414 | 84.189 | 1005306 | 780081 |
| Mean ± SD | 113.02 ± 16.4 | 108.01 ± 16.64 | 1152070 ± 166219 | 992974 ± 164820 |

Water Content % (Animal # in Parenthesis)

TABLE 3

| | Sham | Injured-no treatment | Injured-treated |
|---|---|---|---|
| | 78.90 (51 right side) | 83.36 (9) | 80.07 (10) |
| | 79.79 (51 left side) | 83.97 (14) | 80.02 (52) |
| | 78.91 (53 right side) | 83.72 (55) | 80.20 (54) |
| | 79.06 (53 left side) | | |
| Mean ± SD | 79.17 ± 0.42 | 83.68 ± 0.31 | 80.10 ± 0.09 |

Figure 16:
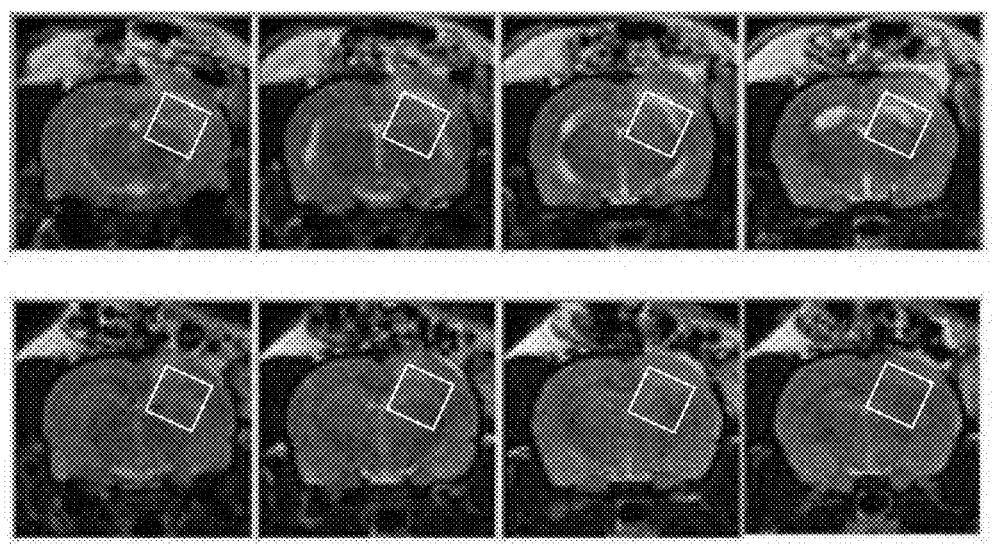
FIG. 16 illustrates T2-weighted MR images from axial planes illustrating the localization of MR spectra voxels acquired from rat brain in vivo.
Figure 17:
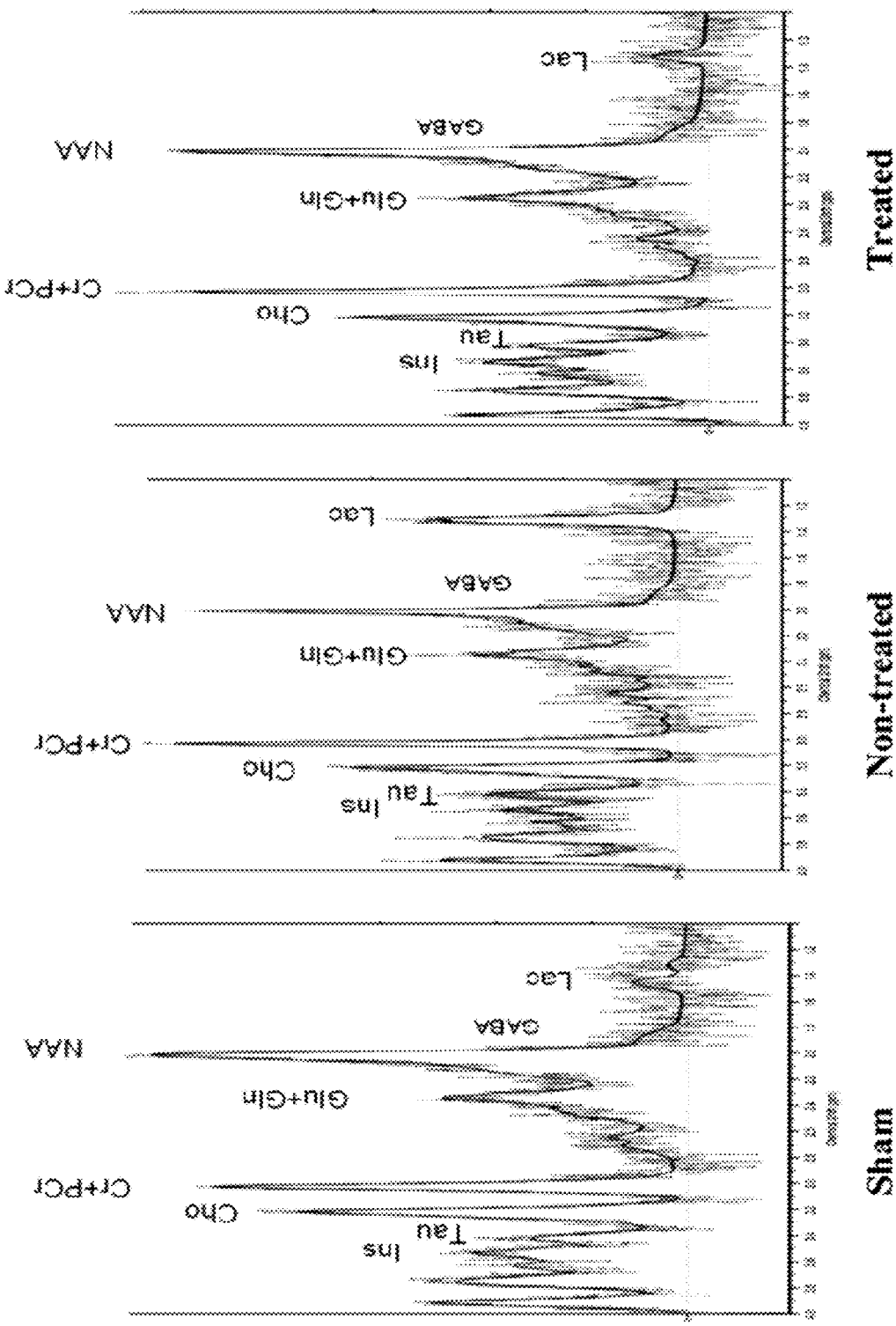
FIG. 17 illustrates single-voxel MR spectra obtained from brains of sham surgery, brain injured and brain injured plus treatment. The metabolites are labeled as Ins (myoinositol), Tau (taurine), Cho (choline-containing compounds), Cr+PCr (creatine and phosphorus creatine), Glu+Gln (glutamate and glutamine), NAA (N-acetyl aspartate), GABA ($\gamma$-aminobutyric acid) and Lac (lactate)

The T2-weighted MR images from axial planes illustrating the localization of MR spectral voxels are shown in FIG. 16, with the spectral voxel outlined by the white box. FIG. 17 shows an example of a Single-Voxel MR spectra obtained from either a sham animal (left), a non-treated animal (center), or a treated animal (right). The spectra show low levels of lactate for the sham animal (arrow), high levels for the non-treated animal, and low levels for the treated animal. All metabolites measured are shown in Table 4. Lactate levels in sham areas were significantly lower than in non-treated animals. Lactate levels between sham animals and treated animals were not significantly different. Lactate levels in treated animals showed a trend to be lower than in non-treated animals. The remaining metabolites which were significantly different (with p values) are identified in Table 5, where the treated animals are shown not to be significantly different than the sham.

TABLE 4

| Animal Number | GABA | Gln | Glu | Ins | Lac | NAA | Tau | Cr + PCr |
|---|---|---|---|---|---|---|---|---|
| Sham | | | | | | | | |
| 18 | 6.384 | 11.224 | 21.531 | 13.061 | 0 | 16.224 | 8.553 | 14.286 |
| 21 | 5.065 | 9.764 | 18.673 | 10.918 | 5.875 | 11.837 | 8.763 | 13.776 |
| 22 | — | 8.721 | 12.143 | 10.306 | — | 9.238 | 5.174 | 10.112 |
| 30 | — | 9.962 | 17.449 | 10.612 | — | 10.816 | 5.08 | 11.122 |
| 31 | — | 9.846 | 15.612 | 10.612 | — | 9.864 | 4.835 | 11.633 |
| 34 | 4.67 | 9.798 | 17.55 | 10.612 | — | 11.122 | 7.416 | 12.551 |
| 49 | 8.581 | 9.938 | 21.939 | 14.184 | 1.939 | 15.816 | 8.105 | 14.184 |
| 47 | 4.69 | 6.691 | 17.755 | 11.122 | 0.516 | 11.838 | 5.817 | 12.449 |
| Mean ± SD | 5.88 ± 1.67 | 9.49 ± 1.32 | 17.83 ± 3.13 | 11.42 ± 1.41 | 2.08 ± 2.66 | 12.09 ± 2.58 | 6.72 ± 1.66 | 12.51 ± 1.51 |
| Injured - non-treated | | | | | | | | |
| 14 | — | 5.712 | 11.122 | 6.042 | 8.481 | 6.498 | 2.885 | 9.686 |
| 16 | — | 7.244 | 12.653 | 7.699 | 5.49 | 8.828 | 7.909 | 11.735 |
| 27 | — | 7.401 | 10.034 | 7.984 | — | 6.094 | 4.416 | 8.159 |
| 29 | — | 10.918 | 14.082 | 9.408 | 4.997 | 7.879 | 7.26 | 10.408 |
| 20 | 3.515 | 10.408 | 12.041 | 9.467 | — | 8.264 | 5.933 | 10.019 |
| 23 | 2.654 | 9.405 | 11.224 | 7.18 | 8.702 | 6.811 | 5.359 | 8.686 |
| 33 | — | 9.551 | 12.857 | 10.408 | 6.916 | 8.354 | 8.832 | 11.633 |
| 37 | — | 7.053 | 13.776 | 7.673 | 10.306 | 8.714 | 7.45 | 10.51 |
| 40 | 6.426 | 10.188 | 17.755 | 11.551 | 6.761 | 12.653 | 8.866 | 13.571 |
| 41 | 4.58 | 7.846 | 13.878 | 9.179 | 3.193 | 9.727 | 6.208 | 10.141 |
| 42 | — | 9.17 | 15.816 | 11.112 | 10.204 | 10.51 | 8.925 | 13.163 |
| Mean ± SD | 4.84 ± 1.47 | 8.63 ± 1.66 | 13.20 ± 2.22 | 8.89 ± 1.74 | 7.23 ± 2.41 | 8.58 ± 1.89 | 6.73 ± 1.97 | 10.70 ± 1.69 |
| Injured - treated | | | | | | | | |
| 13 | — | 4.863 | 12.143 | 8.045 | 2.848 | 7.989 | 5.753 | 10.155 |
| 15 | 4.635 | 9.331 | 16.837 | 9.862 | 6.743 | 10.51 | 8.244 | 11.939 |
| 17 | 5.198 | 10.918 | 18.163 | 12.959 | 2.859 | 12.959 | 10.061 | 15.408 |
| 26 | 6.481 | 9.124 | 18.367 | 11.735 | — | 11.327 | 7.186 | 11.735 |
| 28 | 3.615 | 8.346 | 10.714 | 8.404 | — | 6.425 | 5.859 | 9.199 |
| 19 | 4.266 | 8.612 | 14.082 | 10.816 | — | 9.328 | 8.201 | 11.837 |
| 35 | 5.976 | 9.278 | 14.184 | 11.633 | 5.961 | 12.245 | 8.263 | 13.163 |
| 36 | 4.743 | 9.458 | 14.694 | 10.063 | 8.833 | 9.594 | 8.42 | 11.429 |

TABLE 4-continued

| Animal Number | GABA | Gln | Glu | Ins | Lac | NAA | Tau | Cr + PCr |
|---|---|---|---|---|---|---|---|---|
| 39 | 5.447 | 8.855 | 15.714 | 12.245 | 2.687 | 11.531 | 8.563 | 12.755 |
| 45 | 5.809 | 10.204 | 21.429 | 16.224 | 2.394 | 14.796 | 9.993 | 15.204 |
| 48 | 4.271 | 9.515 | 20. | 12.041 | 2.542 | 12.041 | 8.13 | 13.571 |
| Mean ± SD | 5.04 ± 0.89 | 8.95 ± 1.53 | 16.03 ± 3.29 | 11.28 ± 2.27 | 4.36 ± 2.47 | 10.79 ± 2.36 | 8.06 ± 1.38 | 12.39 ± 1.90 |

TABLE 5

| Groups | Glu | Inos | NAA | Total Cr |
|---|---|---|---|---|
| Non-treat vs sham | 0.002 | 0.006 | 0.002 | 0.029 |
| Non-treat vs treat | 0.030 | 0.007 | 0.03 | 0.033 |
| Sham vs treat | 0.191 | 0.862 | 0.228 | 0.888 |

Figure 18A:
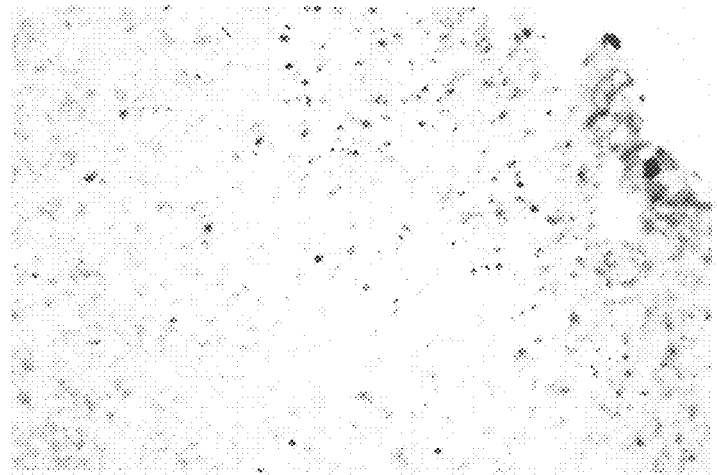
FIGS. 18A and 18B illustrate immunohistochemical analysis of neuronal degradation and death performed by staining for nitrotyrosine on brain samples harvested 72 hours after impaction with the treated group exposed to sub-atmospheric pressure for the entire 72 hours; dark brown spots are dead and dying cells.
Figure 18B:
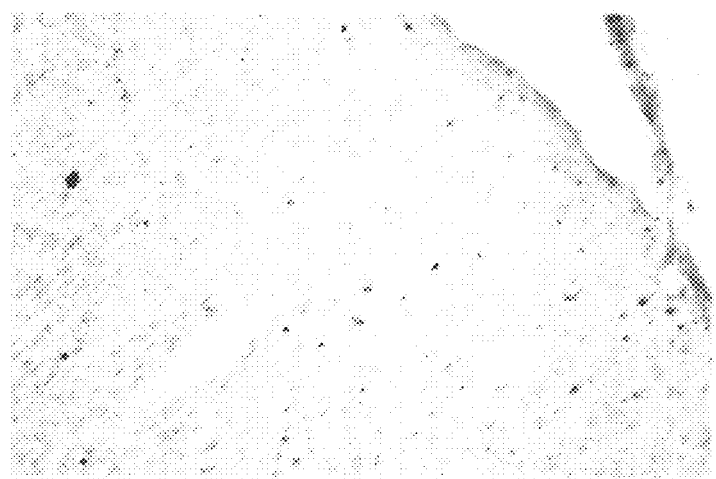

Nitrotyrosine is a marker for cell degradation and death. Analysis for neuronal degradation and death was accomplished by immunohistochemical staining for nitrotyrosine on brain samples harvested 72 hours after surgery/impaction. The treated animals were exposed to sub-atmospheric pressure for the entire 72 hours. FIG. 18A shows histological sections of a non-treated brain section, and FIG. 18B shows a treated brain section. The black dots represent cells that are undergoing degradation and death. There are many more degrading and dying cells in the non-treated section than in the treated section, showing the benefit of treatment.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An apparatus for administering sub-atmospheric pressure to damaged central nervous system tissue comprising:
    a. a porous electrospun bioabsorbable material for placement proximate the damaged central nervous system tissue, the porous electrospun bioabsorbable material having a pore structure configured to communicate sub-atmospheric pressure therethrough for transmission to the damaged central nervous system tissue, and having a selected surface for placement proximate the damaged central nervous system tissue configured to prevent the growth of central nervous system tissue into the porous electrospun bioabsorbable material; and
    b. a cover for enclosing the damaged central nervous system tissue and the electrospun bioabsorbable material, the cover configured to maintain sub-atmospheric pressure at the electrospun bioabsorbable material and damaged central nervous system tissue.

2. The apparatus according to claim 1, comprising a source of sub-atmospheric pressure in gaseous communication with the porous material for distributing the sub-atmospheric pressure to the central nervous system tissue to be treated.

3. The apparatus according to claim 1, wherein the bioabsorbable material comprises a granulating surface configured to promote the formation of granulation tissue thereat.

4. The apparatus according to claim 1, wherein the cover comprises a self-adhesive sheet.

5. An apparatus for administering sub-atmospheric pressure to damaged central nervous system tissue comprising:
    a. a porous cast bioabsorbable material for placement proximate the damaged central nervous system tissue and having a pore structure configured to communicate sub-atmospheric pressure therethrough for transmission to the damaged central nervous system tissue, and having a selected surface for placement proximate the damaged central nervous system tissue configured to prevent the growth of central nervous system tissue into the porous cast bioabsorbable material; and
    b. a cover for enclosing the damaged central nervous system tissue and the cast bioabsorbable material, the cover configured to maintain sub-atmospheric pressure at the cast bioabsorbable material and damaged central nervous system tissue.

6. The apparatus according to claim 5, comprising a source of sub-atmospheric pressure in gaseous communication with the porous material for distributing the sub-atmospheric pressure to the central nervous system tissue to be treated.

7. The apparatus according to claim 5, wherein the bioabsorbable material comprises a granulating surface configured to promote the formation of granulation tissue thereat.

8. The apparatus according to claims 5, wherein the cover comprises a self-adhesive sheet.

9. An apparatus for administering sub-atmospheric pressure to damaged central nervous system tissue comprising:
    a. a porous printed bioabsorbable material for placement proximate the damaged central nervous system tissue and having a pore structure configured to communicate sub-atmospheric pressure therethrough for transmission to the damaged central nervous system tissue, and having a selected surface for placement proximate the damaged central nervous system tissue configured to prevent the growth of central nervous system tissue into the porous printed bioabsorbable material; and
    b. a cover for enclosing the damaged central nervous system tissue and the printed bioabsorbable material, the cover configured to maintain sub-atmospheric pressure at the printed bioabsorbable material and damaged central nervous system tissue.

10. The apparatus according to claim 9, comprising a source of sub-atmospheric pressure in gaseous communication with the porous material for distributing the sub-atmospheric pressure to the central nervous system tissue to be treated.

11. The apparatus according to claim 9, wherein the bioabsorbable material comprises a granulating surface configured to promote the formation of granulation tissue thereat.

12. The apparatus according to claim 9, wherein the cover comprises a self-adhesive sheet.

13. The apparatus according to any one of claims 1-3, 4-7, 8-11, and 12, wherein the bioabsorbable material comprises a porous open-cell material.

14. The apparatus according to claim 13, wherein the open-cell material comprises collagen.

15. The apparatus according to any one of claim 1, 5, or 9, wherein the bioabsorbable material comprises polydiolcitrate, polyglycolic acid, polylactic acid, elastin, hyaluronic acid, chitosan, alginates, polyvinyl alcohol, polyethylene, polyester, polyhydroxybutyrate, polyhydroxyfumarate, polytrimethylene-carbonate, polyglycerolsebecate, aliphatic polyanhydride, aromatic polyanhydride, polycaprolactone, or combinations thereof.

16. The apparatus according to any one of claim 1, 5, or 9, wherein the bioabsorbable material comprises a ribbon or string of porous material.

17. The apparatus according to any one of claim 1, 5, or 9, wherein the bioabsorbable material comprises one or more of a synthetic polymer, a flexible sheet, and a porous sheet.

18. The apparatus according to any one of claim 1, 5, or 9, wherein the bioabsorbable material comprises a sealed surface that is sealed to prevent the transmission of sub-atmospheric pressure therethrough.

19. The apparatus according to any one of claims 1, 5 and 9, wherein the pore structure comprises a pore size smaller than the size of fibroblasts and central nervous system cells.

20. The apparatus according to any one of claims 1, 5 and 9, wherein the pore structure comprises a pore size of the open-cell material that is larger than that of fibroblasts.

21. The apparatus according to any one of claims 1, 5 and 9, wherein the pore structure comprises a pore size large enough to allow movement of proteins the size of albumin therethrough.

22. The apparatus according to any one of claims 1, 5 and 9, wherein the pore structure comprises a pore size gradient, wherein pore size varies along a selected direction through the bioabsorbable material.

23. The apparatus according to any one of claims 2, 6 and 10, wherein the source of sub-atmospheric pressure comprises a vacuum pump.

24. The apparatus according to any one of claims 2, 6 and 10, wherein the source of sub-atmospheric pressure is configured to supply a sub-atmospheric pressure of about 25 mm Hg.

25. The apparatus according to any one of claims 2, 6 and 10, wherein the source of sub-atmospheric pressure is configured to supply a sub-atmospheric of up to about 75 mm Hg.

* * * * *